(12) United States Patent
Kingsmore et al.

(10) Patent No.: US 9,940,434 B2
(45) Date of Patent: Apr. 10, 2018

(54) SYSTEM FOR GENOME ANALYSIS AND GENETIC DISEASE DIAGNOSIS

(71) Applicant: THE CHILDREN'S MERCY HOSPITAL, Kansas City, MO (US)

(72) Inventors: Stephen Kingsmore, Leawood, KS (US); Neil Miller, Santa Fe, NM (US); Carol Saunders, Kansas City, MO (US); Sarah Soden, Kansas City, MO (US); Emily G. Farrow, Kansas City, MO (US)

(73) Assignee: THE CHILDREN'S MERCY HOSPITAL, Kansas City, MO (US)

( * ) Notice: Subject to any disclaimer, the term of this patent is extended or adjusted under 35 U.S.C. 154(b) by 367 days.

(21) Appl. No.: 14/431,702

(22) PCT Filed: Sep. 27, 2013

(86) PCT No.: PCT/US2013/062432
§ 371 (c)(1),
(2) Date: Mar. 26, 2015

(87) PCT Pub. No.: WO2014/052909
PCT Pub. Date: Apr. 3, 2014

(65) Prior Publication Data
US 2015/0310163 A1    Oct. 29, 2015

Related U.S. Application Data

(60) Provisional application No. 61/706,646, filed on Sep. 27, 2012, provisional application No. 61/794,980, filed on Mar. 15, 2013.

(51) Int. Cl.
*C40B 60/10* (2006.01)
*G06F 19/18* (2011.01)

(52) U.S. Cl.
CPC ................................. *G06F 19/18* (2013.01)

(58) Field of Classification Search
CPC .................................................. C40B 60/10
See application file for complete search history.

(56) References Cited

U.S. PATENT DOCUMENTS

| | | |
|---|---|---|
| 2002/0029157 A1 | 3/2002 | Marchosky |
| 2006/0036619 A1 | 2/2006 | Fuerst et al. |

(Continued)

OTHER PUBLICATIONS

Solomon et al., Applying Genomic Analysis to Newborn Screening, Molecular Syndromology, Jul. 25, 2012, pp. 59-67, vol. 3, S. Karger AG, Basel.

(Continued)

*Primary Examiner* — Jyoti Nagpaul
(74) *Attorney, Agent, or Firm* — Husch Blackwell LLP

(57) ABSTRACT

The method for genome analysis translates the clinical findings in the patient into a comprehensive test order for genes that can be causative of the patient's illness, delimits analysis of variants identified in the patient's genome to those that are "on target" for the patient's illness, and provides clinical annotation of the likely causative variants for inclusion in a variant warehouse that is updated as a result of each sample that is analyzed and that, in turn, provides a source of additional annotation for variants. The method uses a genome sequence having the steps of entering at least one clinical feature of a patient by an end-user, assigning a weighted value to the term based on the probability of the presence of the term, mapping the term to at least one disease by accessing a knowledge base containing a plurality of data sets, wherein the data sets are made up of associations between (i) clinical features and diseases, (ii) diseases and genes, (iii) genes and genetic variants, and (iv) diseases and gene variants, assigning a truth value to each of the mapped terms based on the associated data sets and the (Continued)

weighted value, to provide a list of results of possible diagnoses prioritized based on the truth values, with continuous adjustment of the weightings of associations in the knowledge base based on updating of each discovered diagnosis and attendant clinical features, genes and gene variants. This method can be performed in fifty hours or twenty-four hours or less.

40 Claims, 10 Drawing Sheets

(56) References Cited

U.S. PATENT DOCUMENTS

2009/0171697 A1    7/2009   Glauser et al.
2011/0098193 A1    4/2011   Kingsmore et al.

OTHER PUBLICATIONS

Sanchari Pradhan et al., Indian genetic disease database, Nucleic Acids Research, 2011, pp. D933-D938, vol. 39, Oxford University Press.
Matthew D. Mailman et al., The NCBI dbGaP database of genotypes and phenotypes, Nature Genetics, Oct. 2007, pp. 1181-1186, vol. 39, No. 10, The Nature Publishing Group.

Iterative Human-Computer Interaction

SYSTEM FOR GENOME ANALYSIS AND GENETIC DISEASE DIAGNOSIS

BACKGROUND ART

Monogenic diseases are frequent causes of neonatal morbidity and mortality, and disease presentations are often undifferentiated at birth. More than 3,500 monogenic diseases have been characterized, but clinical testing is available for only some of them and many feature clinical and genetic heterogeneity. As such, an immense unmet need exists for improved molecular diagnosis in infants. Because disease progression is extremely rapid, albeit heterogeneous, in newborns, molecular diagnoses must occur quickly to be relevant for clinical decision-making.

Neonatal intensive care units (NICUs) are especially suitable for early adoption of diagnostic whole genome shotgun analysis (WGS), because many of the 3,528 monogenic diseases of known cause present during the first 28 days of life. In the United States, more than 20% of infant deaths are caused by congenital malformations, deformations, and chromosomal abnormalities that cause genetic diseases. Although this proportion has remained unchanged for the past 20 years, the prevalence of monogenic diseases in NICUs is not known because ascertainment rates are low. Serial gene sequencing is too slow to be clinically useful for NICU diagnosis. Newborn screens, while rapid, identify only a few genetic disorders for which inexpensive tests and cost-effective treatments exist. Further complicating diagnosis is the fact that the full clinical phenotype can not be manifest in newborn infants (neonates), and genetic heterogeneity can be immense. Thus, acutely ill neonates with genetic diseases are often discharged or deceased before a diagnosis is made. As a result, NICU treatment of genetic diseases is usually empirical, can lack efficacy, be inappropriate, or cause adverse effects.

NICUs are also suitable for early adoption of genomic medicine because extraordinary interventional efforts are customary and innovation is encouraged. Indeed, NICU treatment is among the most cost-effective of high-cost health care, and the long-term outcomes of most NICU subpopulations are excellent. In genetic diseases for which treatments exist, rapid diagnosis is critical for timely delivery of neonatal interventions that lessen morbidity and mortality. For neonatal genetic diseases without effective therapeutic interventions, of which there are many, timely diagnosis avoids futile intensive care and is critical for research to develop management guidelines that optimize outcomes. In addition to influencing treatment, neonatal diagnosis of genetic disorders and genetic counseling can spare parents diagnostic odysseys that instill inappropriate hope or perpetuate needless guilt.

Two recent reports exemplify the diagnostic and therapeutic uses of next generation sequencing (NGS) in the context of childhood genetic diseases. WGS of fraternal twins concordant for dopa-responsive dystonia revealed known mutations in the sepiapterin reductase (SPR) gene. In contrast to other forms of dystonia, treatment with 5-hydroxytryptamine and serotonin reuptake inhibitors is beneficial in patients with SPR defects. Application of this therapy in appropriate cases resulted in clinical improvement. Likewise, extensive testing failed to provide a molecular diagnosis for a child with fulminant pancolitis (extensive inflammation of the colon), in whom standard treatments for presumed Crohn's disease, an inflammatory bowel disease, were ineffective. NGS of the patient's exome, together with confirmatory studies, revealed X-linked inhibitor of apoptosis (XIAP) deficiency. This diagnosis had not been entertained by the treating physicians because XIAP mutations had not previously been associated with colitis. Hemopoietic progenitor cell transplant was performed, as indicated for XIAP deficiency, with complete resolution of colitis. Lastly, for about 3700 genetic illnesses for which a molecular basis has not yet been established, WGS can suggest candidate genes for functional and inheritance-based confirmatory research.

The current cost of research-grade WGS is $7,666, which is similar to the current cost of commercial diagnostic dideoxy sequencing of two or three disease genes. Within the context of the average cost per day and per stay in a NICU in the United States, WGS in carefully selected cases is acceptable and even potentially cost-saving. However, the turnaround time for interpreted WGS results, like that of dideoxy sequencing, is too slow to be of practical utility for NICU diagnoses or clinical guidance (typically about 4 to 6 weeks). The method of the present invention provides WGS and bioinformatic analysis (largely automated) of suspected genetic disorders within 50 hours or 24 hours, which is a time frame that is unique to the system disclosed herein. There are also a promising timing for emergency use in level III and IV NICUs.

As the cost and turnaround time of WGS continue to decrease rapidly, there will be increasing opportunity to utilize WGS to guide the diagnosis, prognosis and treatment (pharmacogenomics) of inherited diseases. However, there are more than 7,500 genetic diseases, of which more than 3,500 monogenic diseases have been characterized at the gene level. Many of these diseases are rare or extremely rare. Further, many of these diseases feature extensive clinical and genetic heterogeneity. Clinical heterogeneity refers to the phenomenon that a genetic disease, caused by defects in a single gene, can be associated with different phenotypes in different affected individuals. Genetic heterogeneity refers to the phenomenon that a genetic disease, associated with a distinct clinical phenotype, can result from mutations in multiple different genes. Together these characteristics make it exceptionally difficult for a physician to know which genetic disease might be causative in an individual patient. Most physicians will never have learned about most genetic diseases. Thus, while it is feasible to decode the entire genome in individual patients, there is no general method whereby a physician can comprehensively select the diseases or genes that should be examined for causality in that patient. Dependent upon the level of specialization in clinical genetics, a physician can be familiar with as many as one hundred diseases that correspond to a particular presentation in an individual patient, or only to one or two diseases.

In practice, however, and as described below, there can be hundreds of diseases that match clinical presentations. Thus, in practice, the diagnosis of most genetic disorders is limited to approximately only 2,000 clinical geneticists in the United States. A diagnosis typically requires referral from a family physician or pediatrician to a subspecialist and then to a clinical geneticist in order for the appropriate tests to be ordered. For broad or optimal physician ordering of genome analysis that is relevant to individual patients of the system of the present invention maps individual abnormal signs, symptoms and laboratory values to the genetic diseases and genes that can feature these diseases. Such a system enables generalist physicians to order specific genomic regions to be interrogated, analyzed and interpreted in a manner that is tailored precisely to the presentations in individual patients. Additionally, such a system greatly facilitates in the interpretation of which genetic variations are likely to be causative in individual patients. As described below, an average genome sequence contains about 4.1 million genetic variations. An average exome (the sum of all of the exons of protein coding genes in the genome) harbors about 150,000 genetic variations. The system of the present invention for comprehensive mapping of clinical features to potentially causative genes allows, as described below, the analysis and interpretation of those variants to be limited by a factor of 100-fold to 10,000-fold. This greatly decreases the time and effort in interpreting genetic variations that are clinically relevant in WGS. Currently, this is a substantial impediment to broad use of WGS in disease diagnosis, prognosis and tailored treatment decisions (pharmacogenomics).

Physicians can use a web based portal to access the system or that is comminucably coupled to the system and enter the symptoms and other patient information. After the information is processed by the system, the system can display the results and/or possible list of diseases in the web based portal.

Currently available mappings of associations of clinical features to diseases to genes to mutations have numerous weaknesses. Firstly, these associations are not probabilistic (weighted by the likelihood of truth (or falsehood) of each association). Secondly, these associations are incomplete (they are a sparse subset of all associations of clinical features, genes, diseases and nucleotide variants, given incomplete knowledge or curation of that knowledge. Thirdly, these associations are not weighted in terms of determinism or causality. Fourthly, the associations contain errors. Fifthly, the associations are largely one-to-one associations as opposed to many-to-many associations. Sixthly, the associations are largely unintegrated and unconsolidated, meaning that clinical feature to disease associations are largely not integrated with, for example, gene to mutation mappings. Seventhly, they do not all use standardized vocabularies. Physicians currently attempt to reach a timely singular diagnosis in an individual patient on the basis of their accumulated knowledge and experience, assisted by one or more diagnostic tests (which are usually single categorical or continuous results), nomograms, clinical severity scores, and lists or applications (apps) of subsets of the known associations. However, these methods are largely subjective, incomplete, and subject to human frailty and finiteness with regard to intelligence and memory and ascertainment and bias and experiences. This is especially true for genetic diseases, many of which are uncommon and of which there are more than 7,360. Diagnostic testing is typically performed as a series of steps, rather than multiplexed testing in parallel. As a result, time to diagnosis is often excessive (months to years) and cost of diagnosis is correspondingly high. This is especially true for genetic diseases, for many of which molecular tests are not available, and existing tests are expensive and have long time-to-result (typically 12 weeks). Furthermore, the time available for a typical physician—patient encounter, in which clinical features are ascertained, is very brief. Delays in definitive disease diagnosis result in interim empirical therapies for patients, and disease progression and poor outcomes should those therapies be inappropriate or not the current optimal regimen for treatment of the specific underlying disease.

The ability to determine genome sequences of individual patients has created a new and strong need to integrate the millions of variants in a given patient with their clinical picture in order to arrive at a molecular diagnosis of disease. Conventional approaches to the interpretation of genomic variant information, have focused first (ad hoc) on the interpretation of genomic variant information, followed by (post hoc) the fitting of that interpreted genomic variant information to the patient's clinical features. These conventional methods examine the potential disease significance of all variants in a genome, greatly slowing analysis. These methods suffer from the drawback that many genomic variants are of unknown functional significance (VUS) and therefore do not point toward or disclose a disease diagnosis. This results in under-interpretation of VUS with regard to disease causality. These methods also suffer from the drawback that the analysis of variant relevance to disease is largely undertaken without estimation of the prior probability of a given disease entity in that patient. In other words, variant interpretation is largely performed aside from knowledge of the clinical features present or a weighting of the probability of each potential genetic disease by the clinical features present in a given patient. In addition, variant interpretation is often performed without analysis of the allele frequency of variants. These lead both to under- and over-interpretation of the causality of genetic variants in particular patients. Likewise, conventional approaches to genetic disease diagnosis based on a single-gene-at-a-time approach results in the over-interpretation of the causality of genetic variants in that single gene in particular patients.

Physicians will greatly benefit from assistance by somewhat similar computational systems that possess the capability to apply all known mappings to the overwhelming complexity of human phenotypes, human diseases and human nucleotide variations for use in the most efficient diagnosis and treatment individual patients within a probabilistic framework. This is becoming profoundly relevant as whole genome sequencing becomes applied to human disease diagnosis. Given current incomplete, erroneous or partially complete reference associations, it would be beneficial to have a system that is not only comprehensive but is also continuously updated by data sets drawn from each patient experience. In addition, it would be beneficial to have a system that uses some form of logical operators and training sets to assist the system in make probabilistic associations, as opposed to binary associations.

In addition, currently no method exists that can identify many or most disease causing mutations that involve large nucleotide inversions, large deletions, insertions, large triplet repeat expansions, gene conversions and complex rearrangements. For each known mutation a specific assay must be developed. One example of a known disease-causing mutation that involves a large inversion, that is clinically important and very difficult to diagnose by comprehensive sequencing methods, such as whole genome sequencing, is the intron 22 inversion (Inv22), in the factor VIII gene (F8), a duplicon-mediated rearrangement, found in about one half of patients with severe hemophilia A worldwide.

Another example of a common disease not readily diagnosed by comprehensive sequencing is Duchenne or Becker muscular dystrophy, for which ⅔ of cases are due to large deletions in the DMD gene. As such, the first line of current testing for DMD is gene specific deletion/duplication testing to identify mutations not readily detectable by sequence analysis. This can be performed by a variety of gene-specific methods: quantitative PCR, long-range PCR, multiplex ligation-dependent probe amplification (MLPA), and DMD-specific chromosomal microarray (CMA). However, these methods are inextensible to whole genome analysis, and DMD testing is not possible by comprehensive genomic approaches. An example of a gene for which the analysis is complicated by both large deletions, and gene conversions is SMN1. Deletions in the SMN1 gene cause spinal muscular atrophy, the most common genetic cause of infant death. 95%-98% of individuals with a clinical diagnosis of SMA are homozygous for a deletion of SMN1. 2%-5% of individuals with a clinical diagnosis of SMA are compound heterozygotes for deletion of at least SMN1 exon 7 and an intragenic inactivating mutation of SMN1. Thus, SMN1 cannot be tested for disease causality by comprehensive genomic approaches at present.

Currently, the scientific community is focused on the use of third generation DNA sequencing technologies and haplotyping using second and third generation sequencing technologies for various purposes, but not for the individual diagnosis of a specific genetic disorder in a particular patient with clinical features that suggest a gene defect for which many or most cases of disease-causing mutations involve large nucleotide inversions, large deletions, insertions, large triplet repeat expansions, gene conversions and complex rearrangements. Rather, these sequencing technologies are being used for genome-wide analyses to detect and analyze all genomic events of these types. Therefore, it would be beneficial to have a system that is a general method for molecular diagnosis of previously described disease-causing mutations that involve large nucleotide inversions, large deletions, insertions, large triplet repeat expansions, gene conversions and complex rearrangements that are clinically important and currently undetectable by next-generation sequencing. The use of third generation DNA sequencing technologies, or a combination of second and third generation sequencing technologies, or second generation sequencing technologies with haplotype estimation (either by assembly or imputation) would allow comprehensive genomic analysis for most genetic diseases to include examination of large nucleotide inversions, large deletions, insertions, large triplet repeat expansions, gene conversions and complex rearrangements that are clinically important and currently undetectable by next-generation sequencing. An alternative approach is to supplement a comprehensive genome sequencing technology with whole transcriptome (RNA) sequencing. RNA sequencing allows the quantity of expression of each gene to be determined. Thus, RNA sequencing can allow indirect detection of the effects of large nucleotide inversions, large deletions, insertions, large triplet repeat expansions, gene conversions and complex rearrangements that are clinically important and currently undetectable by next-generation sequencing by examination of the effect on transcription of that gene or genes. Furthermore, RNA sequencing, when performed together with DNA sequencing, allows examination of allelic expression bias. Allelic expression bias is exquisitely sensitive for detection of the effects of genomic variations that act in cis. Allelic expression bias can only be performed at expressed genomic locations that contain a heterozygous variant. Thus, at a heterozygous site, the proportion of expression from each allele (or chromosome) should be 50%. Deviations from 50% indicated that the variant, or a linked variant, are changing the expression of that locus. Thus, RNA sequencing with calculation of allelic expression bias can allow indirect detection of the effects of large nucleotide inversions, large deletions, insertions, large triplet repeat expansions, gene conversions and complex rearrangements that are clinically important and currently undetectable by next-generation sequencing by examination of the effect on transcription of that gene or genes on maternally and paternally derived chromosomes.

The systems and methods disclosed by the present invention, as described further herein, differ from current approaches to the interpretation of genomic variant information, which have focused first (ad hoc) on the interpretation of genomic variant information, followed by (post hoc) fitting of that interpreted genomic variant information to the patient's clinical features. Instead, these systems described herein utilize the clinical features present in a given patient to define the likelihood of each genetic disease in that patient prior to the interpretation of genomic variant information. This has the advantage that the many genomic variants of unknown functional significance (VUS) can be ranked by likelihood of disease in that patient, and therefore with appropriate weighting for interpretation with regard to disease causality. If variants are analyzed first in the absence of patient information, VUS are likely to be underinterpreted with regard to causality. It also benefits from the advantage that the analysis of variant relevance to disease is largely undertaken in the setting of a calculation of the prior probability of a given disease entity in that patient. This probability is informed by many sources, such as the disease frequency, frequency in various populations, effects of consanguinity, as well as the clinical features in a given patient. Variant interpretation is performed in reference to weighted probabilities of each potential genetic disease based on the clinical features present in a given patient. This leads to tailored appropriate interpretation of the causality of genetic variants in the context of particular patients as well as that of incidental findings.

DISCLOSURE OF INVENTION

A system for phenotype assisted genome analysis in an individual comprising the steps of obtaining a blood sample from an individual, analyzing the sample, performing delimiting variant analysis, interpreting the variants, and reporting a likely causative relationship between the phenotype and the variant(s). The system of the present invention can be performed in fifty or twenty-four hours or less.

A system for identifying genetic variant(s) in an individual comprising the steps of gathering an individual's phenotypic information, comparing the phenotypic information with a gene database to create a gene data set, comparing the phenotypic information with a disease database to create a disease data set, creating a data superset of relevant diseases and genes to analyze by mapping the gene data set and disease data set, wherein the data superset is prioritized based on the application of one or more Boolean operator(s) to the individual phenotypes, and prioritizing candidate genes for testing for a genetic variant based on said data superset.

A system for dynamic, computer-prompted, rapid, objective and largely automated ascertainment of clinical symptoms and signs, the weighting of those features, fitting those features to all or most genetic disease to gene to mutation mappings simultaneously, and integration with all or most of the variants in the patient's genome sequence, together with integration of all of these inputs, in order to arrive at a best singular or sparse list of weighted clinical diagnoses (Dx) for a patient being evaluated by a physician for diagnosis and treatment of a potentially genetic disease. This system uses the patient's symptoms, signs and/or laboratory values (Sx), and/or suspected mode of inheritance, obtained by a physician or other healthcare provider (such as a nurse or genetic counselor) and the patient's genomic variations as data inputs, with or without dynamic prompts by the system, which concomitantly performs comprehensive, multinomial, probabilistic classification, assisted by comprehensive databases of known mappings of genome sequence variations and known associated genes and known associated genetic diseases and known associated symptoms to provide an integrated, computer-assisted probabilistic classification (or interpretation) of the clinical picture and the corresponding genomic variants in order to reach a Dx that is the likely cause of the patient's symptoms and signs and genetic disease. This system has the advantages of being more comprehensive, rapid, objective and accurate (better fit to the patient's particular disease features) than current systems and methods.

In addition, a patient or parent can also enter their symptoms and signs with the use of prompts from a computer program or interface, in addition to or in place of a healthcare provider, and these symptoms and signs are then used in a parallel approach to aid their diagnoses. Thereby, independent inputs of clinical features are derived that have quite different biases—those of the affected individual or their parents, and those of the healthcare provider. These systems are probabilistic, with weightings of the likelihood of truth (or falsehood) of every association and that accounts for a sparse set of associations, clinical features, genes, diseases and nucleotide variants, given incomplete knowledge or curation of that knowledge.

In addition, the system of the present invention can be performed in twenty-four hours (single physician shift) providing a differential diagnosis of genetic disorders by WGS with increased sensitivity for rare and novel variants. The quality and quantity of whole genome sequences from 24-hour WGS was at least as good as 50-hour WGS. A sensitivity for variant genotypes of 96% was obtained by use of two variant detection pipelines and altered variant detection parameters. In both trio and singleton whole genome sequences, the number of true positive variants was substantially improved, with modest increases in false positive variant calls. 24-hour whole genome sequencing with the use of two variant calling pipelines is suggested as the current gold standard for use in emergency diagnosis of genetic disorders.

In addition, the system of the present invention can provide rapid testing and interpretation of genetic diseases that involve large nucleotide inversions, large deletions, insertions, large triplet repeat expansions, gene conversions and complex rearrangements. Other and further objects of the invention, together with the features of novelty appurtenant thereto, will appear in the course of the following description.

BRIEF DESCRIPTION OF FIGURES AND TABLES

In the accompanying figures and tables form a part of the specification and are to be read in conjunction therewith.

BEST MODE FOR CARRYING OUT THE INVENTION

Figure 1:
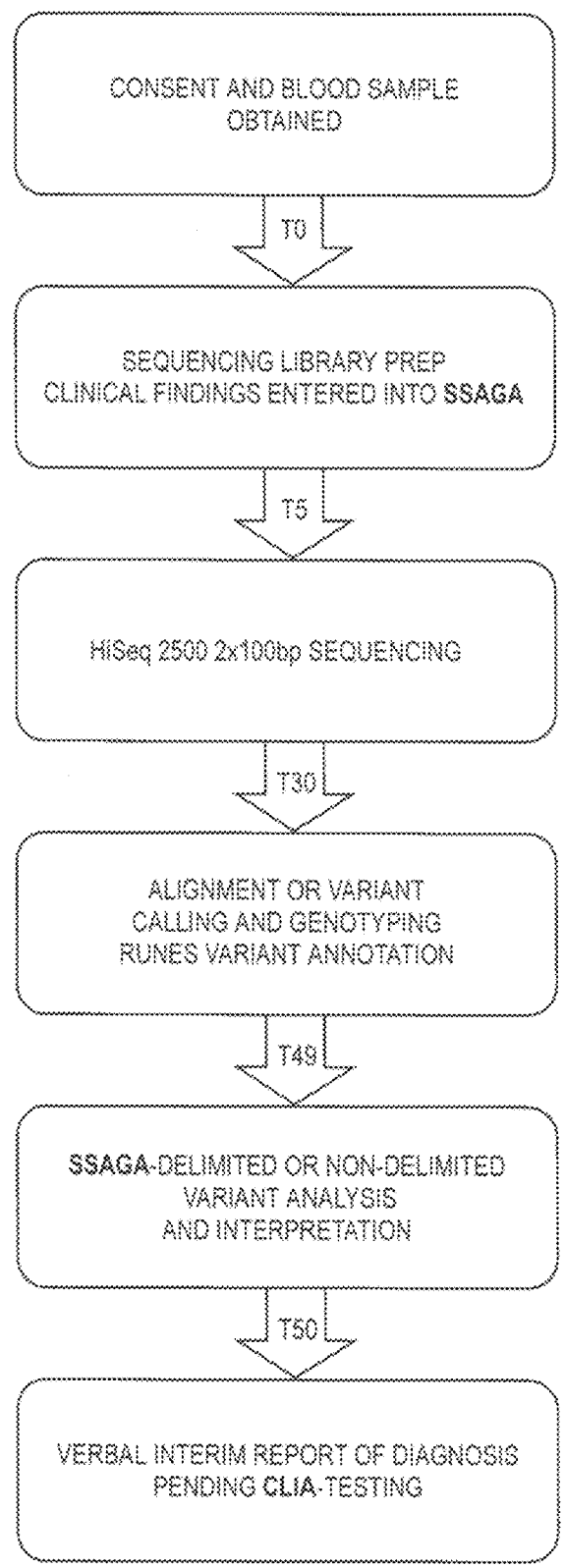
FIG. 1 is an illustration of the steps and timing of the system and method of the present invention for genome analysis and genetic disease diagnosis, where t is hours.

Genomic medicine is a new, structured approach to disease diagnosis and management that prominently features genome sequence information. Whole-genome sequencing ("WGS") by next-generation sequencing ("NGS") technologies has the potential for simultaneous, comprehensive, differential-diagnostic testing of likely monogenic illnesses, which accelerates molecular diagnoses and minimizes the duration of empirical treatment and time to genetic counseling. Indeed, in some cases, WGS or exome sequencing provides molecular diagnoses that could not have been ascertained by conventional single-gene sequencing approaches because of pleiotropic clinical presentation or the lack of an appropriate molecular test.

In the present system, a 50-hour differential diagnosis of genetic disorders is disclosed by WGS that features automated bioinformatic analysis and can used in neonatal intensive care units. Retrospective 50-hour WGS identified known molecular diagnoses in two children. Prospective WGS disclosed a diagnosis of BRAT1-related lethal neonatal rigidity and multifocal seizure syndrome in one infant, identified BCL9L as a novel, recessive visceral heterotaxy gene (HTX6) in a pedigree, and ruled out known candidate genes in two infants. Sequencing of parents or affected siblings expedited the identification of disease gene in prospective cases. Thus rapid WGS can potentially broaden and foreshorten differential diagnosis, resulting in fewer empirical treatments and faster progression to genetic and prognostic counseling.

Symptom- and sign-assisted genome analysis ("SSAGA") is a new clinico-pathological correlation tool that maps the clinical features of 591 well-established, recessive genetic diseases with pediatric presentations (See Table S1 herein below) to corresponding phenotypes and genes known to cause the symptoms. SSAGA was developed for comprehensive automated performance of two tasks: (i) WGS analyses restricted to a superset of gene-associated regions of the genome that are relevant to individual clinical presentations in patients with an illness, in accord with published guidelines for genetic testing in children, and (ii) prioritization of clinical information and of genes identified as having genetic variations in an individual to assist in the interpretation of the WGS results and allow identification of the disease gene variants that are most likely to be causative of that illness. In turn, as noted above, SSAGA enables generalist physicians to order specific genomic regions in WGS to be interrogated, analyzed and interpreted in a manner that is tailored precisely to the presentations in individual patients. Additionally, such a system greatly facilitates in the interpretation of which genetic variations are likely to be causative in individual patients. SSAGA can limit the proportion of variants that must be analyzed and interpreted by a factor of 100-fold to 10,000-fold. This greatly decreases the time and effort in interpreting genetic variations that are clinically relevant in WGS. Currently this is a substantial impediment to broad use of WGS in disease diagnosis, prognosis and tailored treatment decisions (pharmacogenomics). It should be noted that it is possible to increase or decrease the number of clinical terms that are applied to selection of genomic regions in a dynamic manner, allowing flexibility at time of variant interpretation in the number of variations that are nominated for interpretation. In addition, Boolean or other operators can be used in combining the clinical terms in order to rank order the genomic regions containing variations that are nominated for interpretation. Variables such as age, sex or the presence or absence of related family members with similar clinical features can also be added to SSAGA to allow specific patterns of inheritance to be prioritized at time of interpretation, such as dominant or recessive inheritance, or autosomal or sex-linked inheritance.

Figure 3:
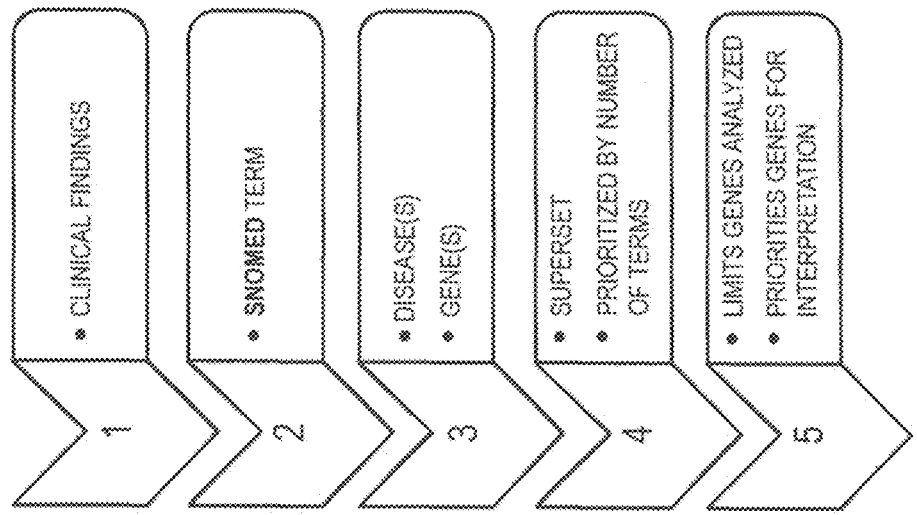
FIG. 3 is an illustration of candidate gene selection by SSAGA (Symptom and Sign Assisted Genome Analysis) for automated variant characterization and interpretation guidance fo the present system.

As shown in FIG. 3, SSAGA has a menu of 227 clinical terms arranged in 9 symptom categories. Standardized clinical terms have been mapped to 591 genetic diseases on the basis of authoritative databases and expert physician reviews. Each disease gene is represented by an average of 8 terms and at most eleven terms (minimum, 1 term, 15 disease genes; maximum, 11 terms, 3 disease genes). A standardized, controlled vocabulary allows clinical and phenotypic information to be described in an unambiguous fashion in medical publications and databases. The use of a standardized vocabulary or ontology to describe or capture individual phenotypic information allows the use of computational algorithms that exploit semantic similarity between related phenotypic abnormalities to define phenotypic similarity metrics, which can be used to perform database searches for clinical diagnostics or as a basis for incorporating individual patient characteristics into large-scale computational analysis, for example, of genome-wide genetic variants or gene expression patterns or other cellular phenomena associated with human disease. For interoperability with various other medical and research methods and software, and to allow the use of semantic and other computational algorithms, SSAGA was designed to utilize standardized vocabularies of terms. For example, clinical signs and symptoms and laboratory findings were described using SNOMED-CT, a widely used, standardized vocabulary. Other standardized vocabularies could be substituted. In particular, use of a standardized vocabulary allows future extensibility of SSAGA to additional clinical terms and to facile translation into other languages. Likewise, disease terms used the standardized vocabulary and nomenclature of Online Mendelian Inheritance in Man (OMIM). Likewise, gene names used the standardized vocabulary and nomenclature of the NCBI Entrez Gene.

In order to validate the feasibility of automated matching of clinical terms to diseases and genes, the presenting features of 533 children who have received a molecular diagnosis at a specific institution within the last 10 years were entered retrospectively into SSAGA. Sensitivity was 99.3% (529), as determined by correct disease and affected gene nominations. Failures included a patient with glucose 6-phosphate dehydrogenase deficiency who presented with muscle weakness (which is not a feature mentioned in authoritative databases, a patient with Janus kinase 3 mutations who had the term "respiratory infection" in his medical records, rather than "increased susceptibility of infections", which is the description in authoritative databases, and a patient with cystic fibrosis who had the term "recurrent infections" in his medical records rather than "respiratory infections," which is the description in authoritative databases. SSAGA nominated an average of 194 genes per patient (maximum 430, minimum 5). Thus, SSAGA displayed sufficient sensitivity for the initial selection of known, recessive candidate genes in children with specific clinical presentations.

In its present embodiment, SSAGA has a menu of 227 clinical terms arranged in 9 symptom categories, and mappings to 591 genetic diseases. More than 3,500 monogenic diseases have been characterized to date and the total number of genetic diseases is believed to be over 7500. Thus, for broadest utility, SSAGA should be extended to all genetic diseases, disease genes and clinical phenotypes (symptoms, signs and other laboratory test values). A key component of an extension of SSAGA to additional diseases is that it retains the current features of using standardized nomenclatures and vocabularies. One such database of standardized clinical phenotypes is the Human Phenotype Ontology (HPO, http://compbio.charite.de/phenexplorer/). This dataset has 9,940 clinical features (with standardized HPO clinical terms), 5,040 OMIM disease terms and 1,825 Entrez genes (Clin Genet. 2010 June; 77(6):525-34. The human phenotype ontology. Robinson P N, Mundlos S. The HPO is freely available at http://www.human-phenotype-ontology.org. Another database of clinical terms is the London Dysmorphology Database (LDDB). This has been a resource used by many clinical geneticists to help in the differential diagnosis of genetic diseases. At present, LDDB does not use a controlled vocabulary and cannot be extended to SSAGA. However, the categories of the LDDB have been mapped to HPO terms, which allows SSAGA to convert phenotypic data encoded with LDDB categories into HPO terms. The mapping is available at http://compbio.charite.de/svn/hpo/trunk/src/mappings/.

Rapid WGS is used in order to recapitulate known results and perform rapid WGS retrospectively on DNA samples from two infants with molecular diagnoses that had previously been identified by clinical testing. Then, to assess the potential diagnostic utility of rapid WGS, prospective WGS was performed in five undiagnosed newborns with clinical presentations that strongly suggested a genetic disorders as well as their siblings.

As illustrated by the flowchart in FIG. 1, a system of automation of the five main components of WGS as well as bioinformatics-based gene-variant characterization and clinical interpretation, all in an integrated workflow, made possible about 50-hour time-to-differential molecular diagnosis of genetic disorders.

Figure 2:
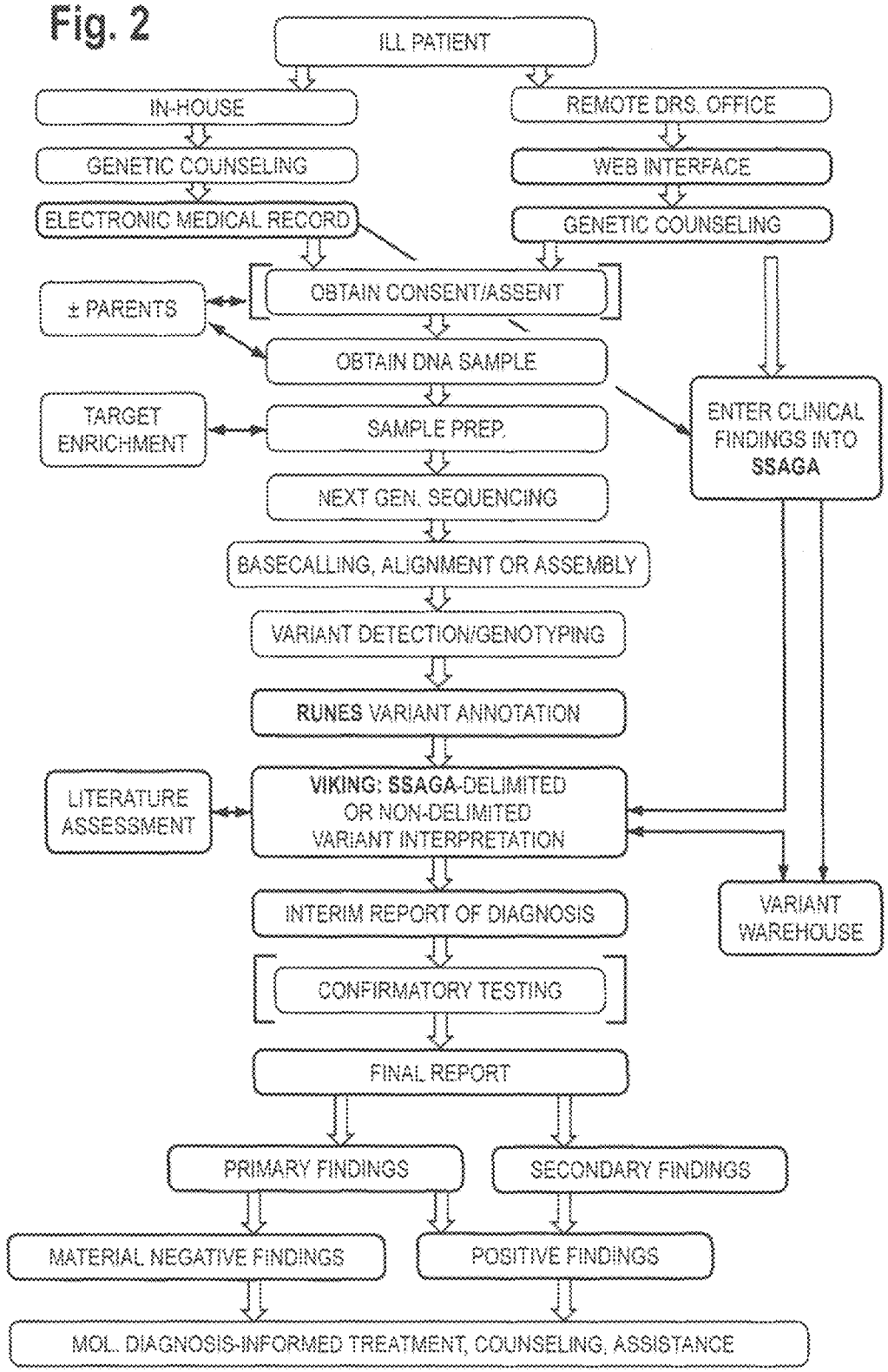
FIG. 2 is an illustration of an overview of molecular diagnostic testing of the present system of an ill patient by sequencing showing the utility of RUNES for annotation of variants (in order to assist in the interpretation of their clinical significance) and of SSAGA.

Referring to FIG. 2, an overview of the method for genome analysis and genetic disease diagnosis is illustrated showing the molecular diagnostic testing of an ill patient by next-generation sequencing showing the utility of RUNES for annotation of variants (in order to assist in the interpretation of their clinical significance) and of SSAGA. The utility of SSAGA is three-fold: (1) to translate the clinical findings in the patient into a comprehensive test order for genes that may be causative of the patient's illness; (2) to delimit analysis of variants identified in the patient's genome to those that are "on target" for the patient's illness; and (3) to provide clinical annotation of the likely causative variants for inclusion in a variant warehouse that is updated as a result of each sample that is analyzed and that, in turn, provides a source of additional annotation for variants.

Specifically, sample preparation for WGS was shortened from 16 to 4.5 hours, while a physician simultaneously entered into SSAGA clinical terms that described the neonates' illnesses as shown in FIG. 3. For each sample, rapid WGS [2×100 base-pair (bp) reads, including on-board cluster generation and paired-end sequencing] was performed in a single run on the Illumina HiSeq2500 and took about 26 hours. Base calling, genomic sequence alignment, and gene-variant calling took about 15 hours. The HiSeq 2500 runs yielded 121 to 139 GB of aligned sequences (34- to 41-fold aligned genome coverage; Table 1). Eighty-eight to 91 percent of bases had >99.9% likelihood of being correct (quality score ≥30, using Illumina software equivalent to Phred). We detected 4.00±0.20 million nucleotides that differed from the reference genome sequence (variants) (mean±SD) in nine samples, one from each of nine infants (See Table 1 below). Table 1 shows the sequencing, alignment, and variant statistics of nine samples analyzed by rapid WGS. ACMG: American College of Medical Genetics; Cat.: Category; Cand.: Candidate; VUS: Variant of uncertain significance. ACMG Category 1-4 variants are a subset of gene associated variants.

TABLE 1

| Sample | Run Time (hours) | Sequence (giga-bases) | High Quality Reads (%) | Mito-chondrial Genome Variants | Nuclear Genome Variants | Gene Associated Variants | ACMG Cat. 1-4 Variants | ACMG Cat. 1-4 Allele Frequency <1% | ACMG Cat. 1-3 Allele Frequency <1% | Candidate Genes | Cand. Gene Cat. 1 Variants | Cand. Gene VUS |
|---|---|---|---|---|---|---|---|---|---|---|---|---|
| UDT002 | 25.5 | 133 | 91% | 33 | 4,014,761 | 1,888,650 | 10,733 | 1,989 | 1,330 | 352 (9) | 2 | 0 |
| UDT173 | 25.5 | 139 | 89% | 40 | 3,977,062 | 1,859,095 | 10,501 | 2,190 | 1,296 | 347 (3) | 0 | 1 |
| CMH064 | 26.6 | 121 | 88% | 41 | 3,985,929 | 1,869,515 | 10,701 | 1,884 | 1,348 | 34 | 0 | 1 |
| CMH076 | 25.7 | 134 | 88% | 34 | 4,498,146 | 2,098,886 | 11,891 | 2,552 | 1,351 | 89 | 0 | 1 |
| CMH172 | 26.5 | 113 | 91% | 39 | 3,759,165 | 1,749,868 | 10,135 | 1,456 | 982 | 174 | 0 | 1 |
| CMH184 | 26.5 | 137 | 90% | 37 | 3,921,135 | 1,840,738 | 10,883 | 1,168 | 833 | 12 | 0 | 0 |
| CMH185 | 40 | 117 | 93% | 37 | 3,922,736 | 1,831,997 | 10,810 | 1,164 | 840 | 14 | 0 | 0 |
| CMH186 | 25.5 | 113 | 93% | 37 | 3,933,062 | 1,827,499 | 10,713 | 1,202 | 868 | 14 | . | . |
| CMH202 | 40 | 116 | 93% | 39 | 3,947,053 | 1,849,647 | 10,805 | 1,283 | 901 | . | . | . |

The following analytic metrics were reported. In three samples, genome variants identified by 50-hour WGS were compared with those identified by deep targeted sequencing of either exons and 20 intron-exon boundary nucleotides of a panel of 525 recessive disease genes (panel 1, CMH-Dx1) or the exome. The CMH-Dx1 panel comprised 8,813 exonic and intronic targets, totaling 2.1 million nucleotides, see Table S1 below.

TABLE S1

| OMIM ID | Disease | Disease Symbol | Gene Symbol |
|---|---|---|---|
| 231550 | ACHALASIA-ADDISONIANISM-ALACRIMA SYNDROME | AAA | AAAS |
| 242500 | ICHTHYOSIS CONGENITA, HARLEQUIN FETUS TYPE | | ABCA12 |
| 610921 | SURFACTANT METABOLISM DYSFUNCTION, PULMONARY, 3 | SMDP3 | ABCA3 |
| 601847 | CHOLESTASIS, PROGRESSIVE FAMILIAL INTRAHEPATIC 2 | PFIC2 | ABCB11 |
| 602347 | CHOLESTASIS, PROGRESSIVE FAMILIAL INTRAHEPATIC | PFIC3 | ABCB4 |
| 256450 | HYPERINSULINEMIC HYPOGLYCEMIA, FAMILIAL, 1 | HHF1 | ABCC8 |
| 300100 | ADRENOLEUKODYSTROPHY | ALD | ABCD1 |
| 611126 | DEFICIENCY OF ACYL-CoA DEHYDROGENASE FAMILY MEMBER 9 | | ACAD9 |
| 201475 | ACYL-CoA DEHYDROGENASE, LONG-CHAIN, DEFICIENCY OF | | ACADL |
| 201450 | ACYL-CoA DEHYDROGENASE, MEDIUM-CHAIN, DEFICIENCY OF | MCAD | ACADM |
| 201475 | ACYL-CoA DEHYDROGENASE, VERY LONG-CHAIN, DEFICIENCY OF | | ACADVL |
| 203750 | ALPHA-METHYLACETOACETIC ACIDURIA | | ACAT1 |
| 264470 | PEROXISOMAL ACYL-CoA OXIDASE DEFICIENCY | ALD | ACOX1 |
| 300387 | MENTAL RETARDATION, X-LINKED 68 | MRX68 | ACSL4 |
| 102700 | SEVERE COMBINED IMMUNODEFICIENCY, AUT REC, T CELL-NEGATIVE, | | ADA |
| 274150 | THROMBOTIC THROMBOCYTOPENIC PURPURA, CONGENITAL | TTP | ADAMTS13 |
| 231050 | GELEOPHYSIC DYSPLASIA | | ADAMTSL2 |
| 309548 | MENTAL RETARDATION X-LINKED ASSOCIATED WITH FRAGILE SITE | FRAXE | AFF2 |
| 232400 | GLYCOGEN STORAGE DISEASE III | | AGL |
| 600121 | RHIZOMELIC CHONDRODYSPLASIA PUNCTATA, TYPE 3 | RCDP3 | AGPS |
| 300034 | MENTAL RETARDATION X-LINKED 88 | MRX88 | AGTR2 |
| 608629 | JOUBERT SYNDROME 3 | JBTS3 | AHI1 |
| 240300 | AUTOIMMUNE POLYENDOCRINE SYNDROME TYPE I | APS1 | AIRE |
| 270200 | SJOGREN-LARSSON SYNDROME | SLS | ALDH3A2 |
| 271980 | SUCCINIC SEMIALDEHYDE DEHYDROGENASE DEFICIENCY | | ALDH5A1 |
| 266100 | EPILEPSY, PYRIDOXINE-DEPENDENT; EPD | | ALDH7A1 |
| 229600 | FRUCTOSE INTOLERANCE, HEREDITARY | | ALDOB |
| 608540 | CONGENITAL DISORDER OF GLYCOSYLATION, TYPE Ik | CDG1K | ALG1 |
| 607143 | CONGENITAL DISORDER OF GLYCOSYLATION TYPE Ig | CDG1G | ALG12 |
| 607906 | CONGENITAL DISORDER OF GLYCOSYLATION TYPE Ii | CDG1I | ALG2 |
| 601110 | CONGENITAL DISORDER OF GLYCOSYLATION, TYPE Id; CDG1D | ALG3 | ALG3 |
| 603147 | CONGENITAL DISORDER OF GLYCOSYLATION TYPE Ic | CDG1C | ALG6 |
| 608104 | CONGENITAL DISORDER OF GLYCOSYLATION, TYPE Ih | CDG1H | ALG8 |
| 608776 | CONGENITAL DISORDER OF GLYCOSYLATION, TYPE Il | CDG1L | ALG9 |
| 203800 | ALSTROM SYNDROME | ALMS | ALMS1 |
| 241510 | HYPOPHOSPHATASIA, CHILDHOOD | | ALPL |
| 205100 | JUVENILE AMYOTROPHIC LATERAL SCLEROSIS 2 | ALS2 | ALS2 |
| 606353 | PRIMARY LATERAL SCLEROSIS, JUVENILE | PLSJ | ALS2 |
| 214950 | BILE ACID SYNTHESIS DEFECT, CONGENITAL, 4 | | AMACR |
| 605899 | GLYCINE ENCEPHALOPATHY | GCE | AMT |
| 228600 | FIBROMATOSIS, JUVENILE HYALINE | | ANTXR2 |
| 236490 | HYALINOSIS, INFANTILE SYSTEMIC | | ANTXR2 |
| 300630 | MENTAL RETARDATION, X-LINKED 59 | MRX59 | AP1S2 |
| 608233 | HERMANSKY-PUDLAK SYNDROME 2 | HPS2 | AP3B1 |

TABLE S1-continued

| OMIM ID | Disease | Disease Symbol | Gene Symbol |
|---|---|---|---|
| 208920 | ATAXIA, EARLY-ONSET, WITH oculomotor apraxia AND HYPOALBUMINEMIA | | APTX |
| 607426 | COENZYME Q10 DEFICIENCY | | APTX |
| 308370 | INFERTILE MALE SYNDROME | | AR |
| 300436 | MENTAL RETARDATION, X-LINKED 46 | MRX46 | ARHGEF6 |
| 300607 | HYPEREKPLEXIA AND EPILEPSY | | ARHGEF9 |
| 250100 | METACHROMATIC LEUKODYSTROPHY | | ARSA |
| 253200 | MUCOPOLYSACCHARIDOSIS TYPE VI MAROTEAUX-LAMY | | ARSB |
| 302950 | CHONDRODYSPLASIA PUNCTATA 1, X-LINKED RECESSIVE | CDPX1 | ARSE |
| 300004 | CORPUS CALLOSUM, AGENESIS OF, WITH ABNORMAL GENITALIA | | ARX |
| 300215 | LISSENCEPHALY, X-LINKED, 2 | LISX2 | ARX |
| 308350 | EPILEPTIC ENCEPHALOPATHY, EARLY INFANTILE, 1 | | ARX |
| 207900 | ARGININOSUCCINIC ACIDURIA | | ASL |
| 271900 | CANAVAN DISEASE | | ASPA |
| 215700 | CITRULLINEMIA, CLASSIC | | ASS1 |
| 208900 | ATAXIA-TELANGIECTASIA | AT | ATM |
| 219200 | CUTIS LAXA, AUTOSOMAL RECESSIVE, TYPE II | | ATP6V0A2 |
| 309400 | MENKES DISEASE | | ATP7A |
| 277900 | WILSON DISEASE | | ATP7B |
| 211600 | CHOLESTASIS, PROGRESSIVE FAMILIAL INTRAHEPATIC 1 | PFIC1 | ATP8B1 |
| 210600 | SECKEL SYNDROME 1 | | ATR |
| 301040 | α-THALASSEMIA/MENTAL RETARDATION SYNDROME, NONDELETION TYPE, X-LINKED | ATRX | ATRX |
| 250950 | 3-METHYLGLUTACONIC ACIDURIA, TYPE I | | AUH |
| 607091 | CONGENITAL DISORDER OF GLYCOSYLATION TYPE IId | CDG2D | B4GALT1 |
| 248600 | MAPLE SYRUP URINE DISEASE Type Ia | | BCKDHA |
| 248611 | BRANCHED-CHAIN KETO ACID DEHYDROGENASE E1, BETA POLYPEPTIDE | BCKDHB | BCKDHB |
| 300166 | MICROPHTHALMIA, SYNDROMIC | | BCOR |
| 124000 | MITOCHONDRIAL COMPLEX III DEFICIENCY | | BCS1L |
| 603358 | GRACILE SYNDROME | | BCS1L |
| 210900 | BLOOM SYNDROME | BLM | BLM |
| 300659 | MENTAL RETARDATION, X-LINKED 93 | MRX93 | BRWD3 |
| 253260 | BIOTINIDASE DEFICIENCY | | BTD |
| 300755 | AGAMMAGLOBULINEMIA, X-LINKED XLA | | BTK |
| 251880 | MITOCHONDRIAL DNA DEPLETION SYNDROME, HEPATOCEREBRAL FORM | | C10ORF2 |
| 271245 | INFANTILE-ONSET SPINOCEREBELLAR ATAXIA | IOSCA | C10ORF2 |
| 259730 | OSTEOPETROSIS, AUTOSOMAL RECESSIVE 3 | OPTB3 | CA2 |
| 607426 | COENZYME Q10 DEFICIENCY | | CABC1 |
| 300749 | MENTAL RETARDATION AND MICROCEPHALY WITH PONTINE AND CEREBELLAR HYPOPLASIA | CASK | CASK |
| 236200 | HOMOCYSTINURIA | | CBS |
| 613493 | IMMUNODEFICIENCY, COMMON VARIABLE, 3 | CVID3 | CD19 |
| 186790 | SCID, AUT REC, T CELL-NEGATIVE, B CELL+, NK CELL+ | CD3D | CD3D |
| 186830 | IMMUNODEFICIENCY DUE TO DEFECT IN CD3-EPSILON | CD3E | CD3E |
| 186740 | IMMUNODEFICIENCY DUE TO DEFECT IN CD3-GAMMA | CD3G | CD3G |
| 186780 | IMMUNODEFICIENCY DUE TO DEFECT IN CD3-ZETA | CD3Z | CD3Z |
| 308230 | IMMUNODEFICIENCY WITH HYPER-IgM, TYPE 1 | HIGM1 | CD40LG |
| 601067 | USHER SYNDROME, TYPE ID | USH1D | CDH23 |
| 610188 | JOUBERT SYNDROME 5 | JBTS5 | CEP290 |
| 312060 | PROPERDIN DEFICIENCY, X-LINKED | | CFP |
| 219700 | CYSTIC FIBROSIS | CF | CFTR |
| 253290 | MULTIPLE PTERYGIUM SYNDROME, LETHAL TYPE | | CHRNA1 |
| 253290 | MULTIPLE PTERYGIUM SYNDROME, LETHAL TYPE | | CHRND |
| 253290 | MULTIPLE PTERYGIUM SYNDROME, LETHAL TYPE | | CHRNG |
| 265000 | MULTIPLE PTERYGIUM SYNDROME, ESCOBAR VARIANT | | CHRNG |
| 300009 | DENT DISEASE 1 | CLCN5 | CLCN5 |
| 611490 | OSTEOPETROSIS, AUTOSOMAL RECESSIVE 4 | OPTB4 | CLCN7 |
| 607626 | ICHTHYOSIS, LEUKOCYTE VACUOLES, ALOPECIA, AND SCLEROSING CHOLANGITIS | | CLDN1 |
| 248190 | HYPOMAGNESEMIA, RENAL, WITH OCULAR INVOLVEMENT | | CLDN19 |
| 204200 | NEURONAL CEROID LIPOFUSCINOSIS 3 | CLN3 | CLN3 |
| 256731 | NEURONAL CEROID LIPOFUSCINOSIS 5 | CLN5 | CLN5 |
| 601780 | CEROID LIPOFUSCINOSIS, NEURONAL, 6 | CLN6 | CLN6 |
| 600143 | CEROID LIPOFUSCINOSIS, NEURONAL, 8 | CLN8 | CLN8 |
| 610003 | CEROID LIPOFUSCINOSIS, NEURONAL, 8, NORTHERN EPILEPSY VARIANT | | CLN8 |
| 276902 | Usher syndrome type 3A | CLRN1 | CLRN1 |
| 611209 | CONGENITAL DISORDER OF GLYCOSYLATION TYPE IIg | CDG2G | COG1 |
| 608779 | CONGENITAL DISORDER OF GLYCOSYLATION, TYPE IIe | CDG2E | COG7 |
| 611182 | CONGENITAL DISORDER OF GLYCOSYLATION TYPE IIh | CDG2H | COG8 |
| 226650 | EPIDERMOLYSIS BULLOSA, JUNCTIONAL, NON-HERLITZ TYPE | | COL17A1 |
| 203780 | ALPORT SYNDROME, AUTOSOMAL RECESSIVE | | COL4A3 |
| 203780 | ALPORT SYNDROME, AUTOSOMAL RECESSIVE | | COL4A4 |

TABLE S1-continued

| OMIM ID | Disease | Disease Symbol | Gene Symbol |
|---|---|---|---|
| 301050 | ALPORT SYNDROME, X-LINKED | ATS | Col4A5 |
| 226600 | EPIDERMOLYSIS BULLOSA DYSTROPHICA, AUTOSOMAL RECESSIVE | RDEB | COL7A1 |
| 607426 | COENZYME Q10 DEFICIENCY | | COQ2 |
| 607426 | COENZYME Q10 DEFICIENCY | | COQ9 |
| 220110 | Complex IV deficiency | | COX10 |
| 220110 | Complex IV deficiency | | COX15 |
| 220110 | Complex IV deficiency | | COX6B1 |
| 237300 | CARBAMOYL PHOSPHATE SYNTHETASE I DEFICIENCY, HYPERAMMONEMIA DUE TO | | CPS1 |
| 255120 | CARNITINE PALMITOYLTRANSFERASE I DEFICIENCY | | CPT1A |
| 255110 | CARNITINE PALMITOYLTRANSFERASE II DEFICIENCY, LATE-ONSET | | CPT2 |
| 600649 | CARNITINE PALMITOYLTRANSFERASE II DEFICIENCY, INFANTILE | | CPT2 |
| 608836 | CARNITPNE PALMITOYLTRANSFERASE II DEFICIENCY, LETHAL NEONATAL | | CPT2 |
| 601378 | CRISPONI SYNDROME | | CRLF1 |
| 610854 | OSTEOGENESIS IMPERFECTA, TYPE IIB | | CRTAP |
| 254800 | MYOCLONIC EPILEPSY OF UNVERRICHT AND LUNDBORG | | CSTB |
| 219750 | CYSTINOSIS, ADULT NONNEPHROPATHIC | | CTNS |
| 219800 | CYSTINOSIS, NEPHROPATHIC | CTNS | CTNS |
| 219900 | CYSTINOSIS, LATE-ONSET JUVENILE OR ADOLESCENT NEPHROPATHIC TYPE | | CTNS |
| 610127 | CEROID LIPOFUSCINOSIS, NEURONAL, 10 | CLN10 | CTSD |
| 265800 | PYCNODYSOSTOSIS | | CTSK |
| 300639 | MENTAL RETARDATION X-LINKED WITH BRACHYDACTYLY AND MACROGLOSSIA | | CUL4B |
| 201710 | LIPOID CONGENITAL ADRENAL HYPERPLASIA | CAH | CYP11A1 |
| 202010 | CONGENITAL ADRENAL HYPERPLASIA | CAH | CYP11B1 |
| 202110 | CONGENITAL ADRENAL HYPERPLASIA | CAH | CYP17A1 |
| 201910 | ADRENAL HYPERPLASIA, CONGENITAL, DUE TO 21-HYDROXYLASE DEFICIENCY | CAH1 | CYP21A2 |
| 213700 | CEREBROTENDINOUS XANTHOMATOSIS | | CYP27A1 |
| 264700 | VITAMIN D-DEPENDENT osteopenia, TYPE I | | CYP27B1 |
| 248610 | MSUD type 2 | | DBT |
| 603554 | OMENN SYNDROME | | DCLRE1C |
| 300067 | LISSENCEPHALY, X-LINKED, 1 | LISX1 | DCX |
| 278740 | XERODERMA PIGMENTOSUM, COMPLEMENTATION GROUP E | | DDB2 |
| 608643 | AROMATIC L-AMINO ACID DECARBOXYLASE DEFICIENCY | | DDC |
| 251880 | MITOCHONDRIAL DNA DEPLETION SYNDROME, HEPATOCEREBRAL FORM | | DGUOK |
| 602398 | DESMOSTEROLOSIS | | DHCR24 |
| 270400 | SMITH-LEMLI-OPITZ SYNDROME | SLOS | DHCR7 |
| 300240 | HOYERAAL-HREIDARSSON SYNDROME | HHS | DKC1 |
| 238331 | DIHYDROLIPOAMIDE DEHYDROGENASE DEFICIENCY | MSUD3 | DLD |
| 300189 | MENTAL RETARDATION X-LINKED 90 | MRX90 | DLG3 |
| 310200 | MUSCULAR DYSTROPHY, DUCHENNE TYPE | DMD | DMD |
| 241520 | HYPOPHOSPHATEMIC osteopenia, AUTOSOMAL RECESSIVE | | DMP1 |
| 610198 | 3-METHYLGLUTACONIC ACIDURIA, TYPE V | | DNAJC19 |
| 242860 | IMMUNODEFICIENCY-CENTROMERIC INSTABILITY-FACIAL ANOMALIES SYNDROME | | DNMT3B |
| 243700 | HYPER-IgE RECURRENT INFECTION SYNDROME, AUTOSOMAL RECESSIVE | DOCK8 | DOCK8 |
| 610768 | CONGENITAL DISORDER OF GLYCOSYLATION TYPE Im | CDG1M | DOLK |
| 608093 | CONGENITAL DISORDER OF GLYCOSYLATION, TYPE Ij | CDG1J | DPAGT1 |
| 608799 | CONGENITAL DISORDER OF GLYCOSYLATION, TYPE Ie | CDG1E | DPM1 |
| 274270 | DIHYDROPYRIMIDINE DEHYDROGENASE | DPYD | DPYD |
| 607655 | SKIN FRAGILITY-WOOLLY HAIR SYNDROME | | DSP |
| 609638 | EPIDERMOLYSIS BULLOSA, LETHAL ACANTHOLYTIC | | DSP |
| 613091 | ASPHYXIATING THORACIC DYSTROPHY 3 | ATD3 | DYNC2H1 |
| 305100 | ECTODERMAL DYSPLASIA, HYPOHIDROTIC, X-LINKED | XHED | EDA |
| 277580 | WAARDENBURG-SHAH SYNDROME | | EDN3 |
| 277580 | WAARDENBURG-SHAH SYNDROME | | EDNRB |
| 600501 | ABCD SYNDROME | | EDNRB |
| 219100 | CUTIS LAXA, AUTOSOMAL RECESSIVE, TYPE I | | EFEMP2 |
| 304110 | CRANIOFRONTONASAL SYNDROME | CFNS | EFNB1 |
| 145900 | HYPERTROPHIC NEUROPATHY OF DEJERINE-SOTTAS | CMT3, CMT4F | EGR2 |
| 605253 | NEUROPATHY, CONGENITAL HYPOMYELINATING: CHARCOT-MARIE-TOOTH DISEASE, TYPE 4E | CMT4E | EGR2 |
| 226980 | EPIPHYSEAL DYSPLASIA, MULTIPLE, WITH EARLY-ONSET DIABETES MELLITUS | | EIF2AK3 |
| 208000 | ARTERIAL CALCIFICATION, GENERALIZED, OF INFANCY | GACI | ENPP1 |
| 254780 | MYOCLONIC EPILEPSY OF LAFORA | | EPM2A |
| 607598 | LETHAL CONGENITAL CONTRACTURE SYNDROME 2 | LCCS2 | ERBB3 |
| 278730 | XERODERMA PIGMENTOSUM, COMPLEMENTATION GROUP D | XPD | ERCC2 |
| 601675 | TRICHOTHIODYSTROPHY, PHOTOSENSITIVE | TTDP | ERCC2 |

TABLE S1-continued

| OMIM ID | Disease | Disease Symbol | Gene Symbol |
|---|---|---|---|
| 601675 | TRICHOTHIODYSTROPHY, PHOTOSENSITIVE | TTDP | ERCC3 |
| 610651 | XERODERMA PIGMENTOSUM, COMPLEMENTATION GROUP B | XPB | ERCC3 |
| 278760 | XERODERMA PIGMENTOSUM, COMPLEMENTATION GROUP F | XPF | ERCC4 |
| 278780 | XERODERMA PIGMENTOSUM, COMPLEMENTATION GROUP G | XPG | ERCC5 |
| 133540 | COCKAYNE SYNDROME TYPE B | CSB | ERCC6 |
| 214150 | CEREBROOCULOFACIOSKELETAL SYNDROME 1 | COFS1 | ERCC6 |
| 278800 | DE SANCTIS-CACCHIONE SYNDROME | | ERCC6 |
| 216400 | COCKAYNE SYNDROME, TYPE A | CSA | ERCC8 |
| 268300 | ROBERTS SYNDROME | RBS | ESCO2 |
| 231680 | MULTIPLE ACYL-CoA DEHYDROGENASE DEFICIENCY | MADD | ETFA |
| 231680 | MULTIPLE ACYL-CoA DEHYDROGENASE DEFICIENCY | MADD | ETFB |
| 231680 | MULTIPLE ACYL-CoA DEHYDROGENASE DEFICIENCY | MADD | ETFDH |
| 602473 | ENCEPHALOPATHY, ETHYLMALONIC | | ETHE1 |
| 225500 | ELLIS-VAN CREVELD SYNDROME; EVC | EVC | EVC |
| 607261 | ELLIS-VAN CREVELD SYNDROME | EVC2 | EVC2 |
| 306700 | HEMOPHILIA A; HEMA | F8 | F8 |
| 300746 | HEMOPHILIA B; HEMB | F9 | F9 |
| 276700 | TYROSINEMIA, TYPE I | | FAH |
| 610532 | LEUKODYSTROPHY, HYPOMYELINATING, 5 | | FAM126A |
| 259775 | RAINE SYNDROME | RNS | FAM20C |
| 227645 | Fanconi anemia type C | | FANCC |
| 220110 | Complex IV deficiency | | FASTKD2 |
| 219100 | CUTIS LAXA, AUTOSOMAL RECESSIVE, TYPE I | | FBLN5 |
| 612840 | LEUKOCYTE ADHESION DEFICIENCY TYPE III | LAD3 | FERMT3 |
| 305400 | FACIOGENITAL DYSPLASIA | FGDY | FGD1 |
| 609311 | CHARCOT-MARIE-TOOTH DISEASE, TYPE 4H | CMT4H | FGD4 |
| 606812 | FUMARASE DEFICIENCY | | FH |
| 253280 | MUSCLE-EYE-BRAIN DISEASE | MEB | FKRP |
| 606612 | MUSCULAR DYSTROPHY, CONGENITAL, 1C | MDC1C | FKRP |
| 253800 | FUKUYAMA CONGENITAL MUSCULAR DYSTROPHY | FCMD | FKTN |
| 613068 | NEURODEGENERATION DUE TO CEREBRAL FOLATE TRANSPORT DEFICIENCY | | FOLR1 |
| 601705 | T-CELL IMMUNODEFICIENCY, CONGENITAL ALOPECIA, AND NAIL DYSTROPHY | | FOXN1 |
| 304790 | IMMUNODYSREGULATION, POLYENDOCRINOPATHY, AND ENTEROPATHY, X-LINKED | IPEX | FOXP3 |
| 219000 | FRASER SYNDROME | | FRAS1 |
| 219000 | FRASER SYNDROME | | FREM2 |
| 309549 | MENTAL RETARDATION, X-LINKED 9 | MRX9 | FTSJ1 |
| 230000 | FUCOSIDOSIS | | FUCA1 |
| 232200 | GLYCOGEN STORAGE DISEASE I VON GIERKE DISEASE | GSD1 | G6PC3 |
| 305900 | GLUCOSE-6-PHOSPHATE DEHYDROGENASE | G6PD | G6PD |
| 232300 | GLYCOGEN STORAGE DISEASE II (pompe) | | GAA |
| 245200 | KRABBE DISEASE | | GALC |
| 230200 | GALACTOKINASE DEFICIENCY | | GALK1 |
| 230400 | GALACTOSEMIA | | GALT |
| 612736 | GUANIDINOACETATE METHYLTRANSFERASE DEFICIENCY | | GAMT |
| 608013 | GAUCHER DISEASE | | GBA |
| 232500 | GLYCOGEN STORAGE DISEASE IV | | GBE1 |
| 231670 | GLUTARIC ACIDEMIA I | | GCDH |
| 605899 | GLYCINE ENCEPHALOPATHY | GCE | GCSH |
| 214400 | CHARCOT-MARIE-TOOTH DISEASE TYPE 4A | CMT4A | GDAP1 |
| 309541 | MENTAL RETARDATION, X-LINKED 41, 48 | MRX41, MRX48 | GDI1 |
| 609060 | COMBINED OXIDATIVE PHOSPHORYLATION DEFICIENCY 1 | COXPD1 | GFM1 |
| 124500 | DEAFNESS, CONGENITAL, WITH KERATOPACHYDERMIA AND CONSTRICTIONS OF FINGERS AND TOES | KHM | GJB2 |
| 608804 | LEUKODYSTROPHY, HYPOMYELINATING, 2 | PMLD | GJC2 |
| 301500 | FABRY DISEASE | | GLA |
| 230500 | GM1-GANGLIOSIDOSIS, TYPE I | | GLB1 |
| 230600 | GM1-GANGLIOSIDOSIS TYPE II | | GLB1 |
| 605899 | GLYCINE ENCEPHALOPATHY | GCE | GLDC |
| 253310 | LETHAL CONGENITAL CONTRACTURE SYNDROME 1 | LCCS1 | GLE1 |
| 252500 | MUCOLIPIDOSIS II ALPHA/BETA | | GNPTAB |
| 252600 | MUCOLIPIDOSIS III ALPHA/BETA | | GNPTAB |
| 146110 | HYPOGONADOTROPIC HYPOGONADISM | IHH | GNRHR |
| 312870 | SIMPSON-GOLABI-BEHMEL SYNDROME, TYPE 1 | SGBS1 | GPC3 |
| 605472 | USHER SYNDROME, TYPE IIC | USH2C | GPR98 |
| 611092 | MENTAL RETARDATION AUTOSOMAL RECESSIVE 6 | MRT6 | GRIK2 |
| 266130 | GLUTATHIONE SYNTHETASE DEFICIENCY | | GSS |
| 601675 | TRICHOTHIODYSTROPHY, PHOTOSENSITIVE | TTDP | GTF2H5 |
| 253220 | MUCOPOLYSACCHARIDOSIS TYPE VII SLY SYNDROME | | GUSB |
| 231530 | 3-HYDROXYACYL-CoA DEHYDROGENASE DEFICIENCY | | HADH |
| 600890 | HYDROXYACYL-CoA DEHYDROGENASE/3-KETOACYL-CoA THIOLASE/ENOYL-CoA HYDRATASE, | | HADHA |
| 609015 | TRIFUNCTIONAL PROTEIN DEFICIENCY | | HADHA |
| 609015 | TRIFUNCTIONAL PROTEIN DEFICIENCY | | HADHB |
| 602390 | HEMOCHROMATOSIS, JUVENILE, TYPE 2B | HFE2B | HAMP |

TABLE S1-continued

| OMIM ID | Disease | Disease Symbol | Gene Symbol |
|---|---|---|---|
| 610738 | NEUTROPENIA, SEVERE CONGENITAL, AUTOSOMAL RECESSIVE 3 | SCN3 | HAX1 |
| 141800 | ALPHA THALASSEMIA | HBA1 | HBA1 |
| 141900 | THALASSEMIA MAJOR | HBB | HBB |
| 603903 | SICKLE CELL ANEMIA | | HBB |
| 262600 | PITUITARY DWARFISM III | | HESX1 |
| 272800 | TAY-SACHS DISEASE | TSD | HEXA |
| 268800 | SANDHOFF DISEASE | | HEXB |
| 252930 | MUCOPOLYSACCHARIDOSIS TYPE IIIC (Sanfilippo type c) | | HGSNAT |
| 250620 | BETA-HYDROXYISOBUTYRYL CoA DEACYLASE, DEFICIENCY OF | | HIBCH |
| 602390 | HEMOCHROMATOSIS, JUVENILE, TYPE 2A | HFE2A | HJV |
| 253270 | HOLOCARBOXYLASE SYNTHETASE DEFICIENCY | | HLCS |
| 246450 | 3-HYDROXY-3-METHYLGLUTARYL-CoA LYASE DEFICIENCY | | HMGCL |
| 300322 | LESCH-NYHAN SYNDROME | LNS | HPRT1 |
| 218030 | CORTISOL 11-BETA-KETOREDUCTASE DEFICIENCY | | HSD11B2 |
| 300220 | MENTAL RETARDATION, X-LINKED, SYNDROMIC 10 | MRXS10 | HSD17B10 |
| 605573 | 17-@BETA HYDROXYSTEROID DEHYDROGENASE III DEFICIENCY | | HSD17B3 |
| 261515 | D-BIFUNCTIONAL PROTEIN DEFICIENCY | | HSD17B4 |
| 201810 | 3-BETA-HYDROXYSTEROID DEHYDROGENASE DEFICIENCY TYPE II | CAH | HSD3B2 |
| 224410 | DYSSEGMENTAL DYSPLASIA, SILVERMAN-HANDMAKER TYPE | DDSH | HSPG2 |
| 300706 | MENTAL RETARDATION X-LINKED SYNDROMIC TURNER TYPE | HUWE1 | HUWE1 |
| 607594 | ANTIBODY DEFICIENCY DUE TO ICOS DEFECT | CVID1 | ICOS |
| 309900 | MUCOPOLYSACCHARIDOSIS TYPE II | | IDS |
| 607014 | HURLER SYNDROME | | IDUA |
| 209950 | ATYPICAL MYCOBACTERIOSIS, FAMILIAL | | IFNGR1 |
| 209950 | ATYPICAL MYCOBACTERIOSIS, FAMILIAL | | IFNGR2 |
| 611263 | ASPHYXIATING THORACIC DYSTROPHY 2 | ATD2 | IFT80 |
| 604320 | SPINAL MUSCULAR ATROPHY, DISTAL, AUTOSOMAL RECESSIVE, 1 | DSMA1 | IGHMBP2 |
| 223900 | NEUROPATHY, HEREDITARY SENSORY AND AUTONOMIC, TYPE III | HSAN3 | IKBKAP |
| 209950 | ATYPICAL MYCOBACTERIOSIS, FAMILIAL | | IKBKG |
| 300291 | ECTODERMAL DYSPLASIA, HYPOHIDROTIC, WITH IMMUNE DEFICIENCY | | IKBKG |
| 300301 | ECTODERMAL DYSPLASIA, ANHIDROTIC, W IMMUNODEFICIENCY, OSTEOPETROSIS & LYMPHEDEMA | OLEDAID | IKBKG |
| 209950 | ATYPICAL MYCOBACTERIOSIS, FAMILIAL | | IL12B |
| 209950 | ATYPICAL MYCOBACTERIOSIS, FAMILIAL | | IL12RB1 |
| 300143 | MENTAL RETARDATION, X-LINKED 21 | MRX21 | IL1RAPL1 |
| 612852 | Deficiency of Interleukin-1-receptor antagonist | | IL1RN |
| 300400 | SEVERE COMBINED IMMUNODEFICIENCY, X-LINKED | SCIDX1 | IL2RG |
| 312863 | COMBINED IMMUNODEFICIENCY, X-LINKED | CIDX | IL2RG |
| 246200 | DONOHUE SYNDROME | | INSR |
| 602088 | NEPHRONOPHTHISIS 2 | NPHP2 | INVS |
| 609254 | SENIOR-LOKEN SYNDROME 5 | SLSN5 | IQCB1 |
| 226730 | EPIDERMOLYSIS BULLOSA JUNCTIONALIS WITH PYLORIC ATRESIA | | ITGA6 |
| 226650 | EPIDERMOLYSIS BULLOSA, JUNCTIONAL, NON-HERLITZ TYPE | | ITGB4 |
| 226730 | EPIDERMOLYSIS BULLOSA JUNCTIONALIS WITH PYLORIC ATRESIA | | ITGB4 |
| 243500 | ISOVALERIC ACIDEMIA | IVA | IVD |
| 600802 | SEVERE COMBINED IMMUNODEFICIENCY, AUT REC, T CELL⁻, B CELL⁺, NK CELL⁻ | | JAK3 |
| 241200 | BARTTER SYNDROME, ANTENATAL, TYPE 2 | | KCNJ1 |
| 314690 | MENTAL RETARDATION, X-LINKED, SYNDROMIC | | KDM5C |
| 303350 | MASA SYNDROME | | L1CAM |
| 304100 | CORPUS CALLOSUM, PARTIAL AGENESIS OF, X-LINKED | | L1CAM |
| 307000 | HYDROCEPHALUS DUE TO CONGENITAL STENOSIS OF AQUEDUCT OF SYLVIUS | HSAS | L1CAM |
| 607855 | MUSCULAR DYSTROPHY, CONGENITAL MEROSIN-DEFICIENT, 1A | MDC1A | LAMA2 |
| 226650 | EPIDERMOLYSIS BULLOSA, JUNCTIONAL, NON-HERLITZ TYPE | | LAMA3 |
| 226700 | EPIDERMOLYSIS BULLOSA, JUNCTIONAL, HERLITZ TYPE | | LAMA3 |
| 245660 | LARYNGOONYCHOCUTANEOUS SYNDROME | LOCS | LAMA3 |
| 609049 | PIERSON SYNDROME | | LAMB2 |
| 226650 | EPIDERMOLYSIS BULLOSA, JUNCTIONAL, NON-HERLITZ TYPE | | LAMB3 |
| 226700 | EPIDERMOLYSIS BULLOSA, JUNCTIONAL, HERLITZ TYPE | | LAMB3 |
| 226650 | EPIDERMOLYSIS BULLOSA, JUNCTIONAL, NON-HERLITZ TYPE | | LAMC2 |

TABLE S1-continued

| OMIM ID | Disease | Disease Symbol | Gene Symbol |
|---|---|---|---|
| 226700 | EPIDERMOLYSIS BULLOSA, JUNCTIONAL, HERLITZ TYPE | | LAMC2 |
| 608840 | MUSCULAR DYSTROPHY, CONGENITAL, TYPE 1D | | LARGE |
| 215140 | HYDROPS-ECTOPIC CALCIFICATION-MOTH-EATEN SKELETAL DYSPLASIA | | LBR |
| 610915 | OSTEOGENESIS IMPERFECTA, TYPE VIII | | LEPRE1 |
| 176410 | PRECOCIOUS PUBERTY, MALE-LIMITED | | LHCGR |
| 221750 | PITUITARY HORMONE DEFICIENCY, COMBINED, 3; CPHD3 | | LHX3 |
| 262600 | PITUITARY DWARFISM III | | LHX3 |
| 601559 | STUVE-WIEDEMANN SYNDROME | | LIFR |
| 602450 | SEVERE COMBINED IMMUNODEFICIENCY WITH SENSITIVITY TO IONIZING RADIATION | LIG4 | LIG4 |
| 222448 | DONNAI-BARROW SYNDROME | | LRP2 |
| 220111 | LEIGH SYNDROME, FRENCH-CANADIAN TYPE | LSFC | LRPPRC |
| 214500 | CHEDIAK HIGASHI SYNDROME | CHS | LYST |
| 248500 | MANNOSIDOSIS, ALPHA B, LYSOSOMAL | | MAN2B1 |
| 308205 | ICHTHYOSIS FOLLICULARIS, ATRICHIA, AND PHOTOPHOBIA SYNDROME | | MBTPS2 |
| 252650 | MUCOLIPIDOSIS IV | | MCOLN1 |
| 312750 | RETT SYNDROME | | MECP2 |
| 309520 | LUJAN-FRYNS SYNDROME | | MED12 |
| 249100 | FAMILIAL MEDITERRANEAN FEVER | FMF | MEFV |
| 610951 | CEROID LIPOFUSCINOSIS, NEURONAL, 7 | CLN7 | MFSD8 |
| 212066 | CONGENITAL DISORDER OF GLYCOSYLATIO, TYPE IIa | CDG2A | MGAT2 |
| 300000 | OPITZ GBBB SYNDROME, X-LINKED | | MID1 |
| 249000 | MECKEL SYNDROME TYPE 1 | MKS1 | MKS1 |
| 604004 | MEGALENCEPHALIC LEUKOENCEPHALOPATHY WITH SUBCORTICAL CYSTS | MLC | MLC1 |
| 251100 | METHYLMALONIC ACIDURIA, cblA TYPE | | MMAA |
| 251110 | METHYLMALONIC ACIDURIA, cblB TYPE | | MMAB |
| 277400 | METHYLMALONIC ACIDURIA AND HOMOCYSTINURIA, cblC TYPE | | MMACHC |
| 252150 | MOLYBDENUM COFACTOR DEFICIENCY | | MOCS1 |
| 252150 | MOLYBDENUM COFACTOR DEFICIENCY | | MOCS2 |
| 606056 | CONGENITAL DISORDER OF GLYCOSYLATION TYPE IIb | CDG2B | MOGS |
| 609180 | CONGENITAL DISORDER OF GLYCOSYLATION, TYPE If | CDG1F | MPDU1 |
| 602579 | CONGENITAL DISORDER OF GLYCOSYLATION, TYPE Ib | CDG1B | MPI |
| 604498 | AMEGAKARYOCYTIC THROMBOCYTOPENIA, CONGENITAL | CAMT | MPL |
| 251880 | MITOCHONDRIAL DNA DEPLETION SYNDROME, HEPATOCEREBRAL FORM | | MPV17 |
| 256810 | NAVAJO NEUROHEPATOPATHY | NN | MPV17 |
| 145900 | HYPERTROPHIC NEUROPATHY OF DEJERINE-SOTTAS | CMT3, CMT4F | MPZ |
| 605253 | NEUROPATHY, CONGENITAL HYPOMYELINATING: CHARCOT-MARIE-TOOTH DISEASE, TYPE 4E | CMT4E | MPZ |
| 610498 | COMBINED OXIDATIVE PHOSPHORYLATION DEFICIENCY 2 | COXPD2 | MRPS16 |
| 611719 | COMBINED OXIDATIVE PHOSPHORYLATION DEFICIENCY 5 | COXPD5 | MRPS22 |
| 310400 | MYOTUBULAR MYOPATHY 1 | MTM1 | MTM1 |
| 251000 | METHYLMALONIC ACIDURIA DUE TO METHYLMALONYL-CoA MUTASE DEFICIENCY | | MUT |
| 610377 | MEVALONIC ACIDURIA | | MVK |
| 612260 | MYD88 DEFICIENCY | MYD88D | MYD88D |
| 214450 | GRISCELLI SYNDROME, TYPE 1 | GS1 | MYO5A |
| 256710 | ELEJALDE DISEASE | | MYO5A |
| 276900 | USHER SYNDROME, TYPE I | | MYO7A |
| 237310 | N-ACETYLGLUTAMATE SYNTHASE DEFICIENCY | | NAGS |
| 251260 | NIJMEGEN BREAKAGE SYNDROME | | NBN |
| 310600 | NORRIE DISEASE | ND | NDP |
| 252010 | Complex I Deficiency | NDUFA1 | NDUFA1 |
| 252010 | Complex I Deficiency | NDUFA7 | NDUFA7 |
| 252010 | Complex I Deficiency | NDUFAF2 | NDUFAF2 |
| 252010 | Complex I Deficiency | NDUFAF4 | NDUFAF4 |
| 252010 | Complex I Deficiency | NDUFS3 | NDUFS3 |
| 252010 | Complex I Deficiency | NDUFS4 | NDUFS4 |
| 252010 | Complex I Deficiency | NDUFS5 | NDUFS5 |
| 252010 | Complex I Deficiency | NDUFS6 | NDUFS6 |
| 252010 | Complex I Deficiency | NDUFS7 | NDUFS7 |
| 252010 | Complex I Deficiency | NDUFS8 | NDUFS8 |
| 252010 | Complex I Deficiency | NDUFV1 | NDUFV1 |
| 256030 | NEMALINE MYOPATHY 2 | NEM2 | NEB |
| 256550 | NEURAMINIDASE DEFICIENCY | | NEU1 |
| 610370 | DIARRHEA 4, MALABSORPTIVE, CONGENITAL | | NEUROG3 |
| 611291 | SCID W MICROCEPHALY, GROWTH RETARDATION, & SENS TO IONIZING RADIATION | NHEJ1 | NHEJ1 |
| 254780 | MYOCLONIC EPILEPSY OF LAFORA | | NHLRC1 |
| 302350 | NANCE-HORAN SYNDROME; NHS | | NHS |
| 300497 | X-linked Asperger syndrome-2 | | NLGN4 |
| 257220 | NIEMANN-PICK DISEASE, TYPE C1 | NPC1 | NPC1 |
| 607625 | NIEMANN-PICK DISEASE, TYPE C2 | | NPC2 |

TABLE S1-continued

| OMIM ID | Disease | Disease Symbol | Gene Symbol |
|---|---|---|---|
| 256100 | NEPHRONOPHTHISIS 1 | NPHP1 | NPHP1 |
| 266900 | SENIOR-LOKEN SYNDROME 1 | SLSN1 | NPHP1 |
| 609583 | JOUBERT SYNDROME 4 | JBTS4 | NPHP1 |
| 208540 | RENAL-HEPATIC-PANCREATIC DYSPLASIA | RHPD | NPHP3 |
| 606966 | NEPHRONOPHTHISIS 4 | NPHP4 | NPHP4 |
| 256300 | NEPHROSIS 1, CONGENITAL, FINNISH TYPE | NPHS1 | NPHS1 |
| 600995 | nephrotic syndrome, STEROID-RESISTANT, AUTOSOMAL RECESSIVE | SRN1 | NPHS2 |
| 300200 | CONGENITAL ADRENAL HYPOPLASIA | AHC | NR0B1 |
| 612965 | GONADAL DYSGENESIS WITH ADRENAL FAILURE | | NR5A1 |
| 610916 | Autosomal mental retardation | NSUN2 | NSUN2 |
| 256800 | INSENSITIVITY TO PAIN, CONGENITAL, WITH ANHIDROSIS | CIPA | NTRK1 |
| 271930 | STRIATONIGRAL DEGENERATION, INFANTILE | SNDI | NUP62 |
| 300319 | X-linked mental retardation | NXF5 | NXF5 |
| 309000 | LOWE OCULOCEREBRORENAL SYNDROME | OCRL | OCRL |
| 300209 | SIMPSON-GOLABI-BEHMEL SYNDROME, TYPE 2 | | OFD1 |
| 258501 | 3-@METHYLGLUTACONIC ACIDURIA, TYPE III | | OPA3 |
| 300486 | MENTAL RETARDATION, XLR, W CEREBELLAR HYPOPLASIA & DISTINCTIVE FACIAL APPEARANCE | | OPHN1 |
| 612782 | IMMUNE DYSFUNCTION WITH T-CELL INACTIVATION DUE TO CALCIUM ENTRY DEFECT 1 | ORAI1 | ORAI1 |
| 259720 | OSTEOPETROSIS, AUTOSOMAL RECESSIVE 5 | OPTB5 | OSTM1 |
| 311250 | ORNITHINE TRANSCARBAMYLASE DEFICIENCY, HYPERAMMONEMIA DUE TO | | OTC |
| 261600 | PHENYLKETONURIA | PKU | PAH |
| 300558 | MENTAL RETARDATION, X-LINKED 30 | MRX30 | PAK3 |
| 234200 | NEURODEGENERATION WITH BRAIN IRON ACCUMULATION 1 (Hallervorden-Spatz) | NBIA1 | PANK2 |
| 266150 | PYRUVATE CARBOXYLASE DEFICIENCY | | PC |
| 606054 | PROPIONIC ACIDEMIA | PCCA | PCCA |
| 606054 | PROPIONIC ACIDEMIA | PCCB | PCCB |
| 300088 | EPILEPSY, FEMALE-RESTRICTED, WITH MENTAL RETARDATION | EFMR | PCDH19 |
| 308930 | LEIGH SYNDROME, X-LINKED | | PDHA1 |
| 245349 | PYRUVATE DEHYDROGENASE E3-BINDING PROTEIN DEFICIENCY | | PDHX |
| 608782 | PYRUVATE DEHYDROGENASE PHOSPHATASE DEFICIENCY | | PDP1 |
| 607426 | COENZYME Q10 DEFICIENCY | | PDSS1 |
| 607426 | COENZYME Q10 DEFICIENCY | | PDSS2 |
| 202370 | ADRENOLEUKODYSTROPHY, AUTOSOMAL NEONATAL FORM | | PEX1 |
| 214100 | ZELLWEGER SYNDROME | ZS | PEX1 |
| 202370 | ADRENOLEUKODYSTROPHY, AUTOSOMAL NEONATAL FORM | PEX10 | | PEX10 |
| 214100 | ZELLWEGER SYNDROME | ZS | PEX12 |
| 202370 | ADRENOLEUKODYSTROPHY, AUTOSOMAL NEONATAL FORM | PEX13 | | PEX13 |
| 202370 | ADRENOLEUKODYSTROPHY, AUTOSOMAL NEONATAL FORM | PEX26 | | PEX26 |
| 202370 | ADRENOLEUKODYSTROPHY, AUTOSOMAL NEONATAL FORM | PEX5 | | PEX5 |
| 215100 | RHIZOMELIC CHONDRODYSPLASIA PUNCTATA TYPE 1 | RCDP1 | PEX7 |
| 263200 | POLYCYSTIC KIDNEY DISEASE, AUTOSOMAL RECESSIVE | ARPKD | PKHD1 |
| 266200 | PYRUVATE KINASE DEFICIENCY OF RED CELLS | | PKLR |
| 256600 | INFANTILE NEUROAXONAL DYSTROPHY | INAD1 | PLA2G6 |
| 610725 | nephrotic syndrome, TYPE 3 | NPHS3 | PLCE1 |
| 604310 | Hermansky Pudlak Syndrome, 9 | HPS9 | PLDN |
| 226670 | EPIDERMOLYSIS BULLOSA SIMPLEX WITH MUSCULAR DYSTROPHY | | PLEC1 |
| 611067 | SPINAL MUSCULAR ATROPHY, DISTAL, AUTOSOMAL RECESSIVE, 4 | DSMA4 | PLEKHG5 |
| 217090 | PLASMINOGEN DEFICIENCY TYPE I | | PLG |
| 601451 | NEVO SYNDROME | EDS VIA | PLOD1 |
| 312080 | PELIZAEUS-MERZBACHER DISEASE | PMD | PLP1 |
| 312920 | SPASTIC PARAPLEGIA 2, X-LINKED | SPG2 | PLP1 |
| 212065 | CONGENITAL DISORDER OF GLYCOSYLATION TYPE Ia | CDG1A | PMM2 |
| 145900 | HYPERTROPHIC NEUROPATHY OF DEJERINE-SOTTAS | CMT3, CMT4F | PMP22 |
| 610090 | PYRIDOXAMINE 5-PRIME-PHOSPHATE OXIDASE DEFICIENCY | | PNPO |
| 203700 | ALPERS DIFFUSE DEGENERATION OF CEREBRAL GRAY MATTER WITH HEPATIC CIRRHOSIS | | POLG |
| 253280 | MUSCLE-EYE-BRAIN DISEASE | MEB | POMGNT1 |
| 236670 | WALKER-WARBURG SYNDROME | WWS | POMT1 |
| 236670 | WALKER-WARBURG SYNDROME | WWS | POMT2 |
| 201750 | ANTLEY-BIXLER SYNDROME | ABS1 | POR |
| 613571 | DISORDERED STEROIDOGENESIS | | POR |
| 262600 | PITUITARY DWARFISM III | | POU1F1 |

TABLE S1-continued

| OMIM ID | Disease | Disease Symbol | Gene Symbol |
|---|---|---|---|
| 256730 | NEURONAL CEROID LIPOFUSCINOSIS 1 | CLN1 | PPT1 |
| 309500 | RENPENNING SYNDROME 1 | RENS1 | PQBP1 |
| 603553 | HEMOPHAGOCYTIC LYMPHOHISTIOCYTOSIS, FAMILIAL, 2 | FHL2 | PRF1 |
| 262600 | PITUITARY DWARFISM III | | PROP1 |
| 301835 | ARTS SYNDROME | ARTS | PRPS1 |
| 249500 | MENTAL RETARDATION, AUTOSOMAL RECESSIVE 1 | MRT1 | PRSS12 |
| 145900 | HYPERTROPHIC NEUROPATHY OF DEJERINE-SOTTAS | CMT3, CMT4F | PRX |
| 249900 | METACHROMATIC LEUKODYSTROPHY DUE TO SAPOSIN B DEFICIENCY | | PSAP |
| 611721 | COMBINED SAPOSIN DEFICIENCY | | PSAP |
| 215045 | CHONDRODYSPLASIA, BLOMSTRAND TYPE | BOCD | PTH1R |
| 201000 | CARPENTER SYNDROME | | RAB23 |
| 607624 | GRISCELLI SYNDROME, TYPE 2 | GS2 | RAB27A |
| 300271 | MENTAL RETARDATION X-LINKED 72 | MRX72 | RAB39B |
| 600118 | WARBURG MICRO SYNDROME | WARBM | RAB3GAP1 |
| 212720 | MARTSOLF SYNDROME | | RAB3GAP2 |
| 601457 | SEVERE COMBINED IMMUNODEFICIENCY, AUTOSOMAL RECESSIVE, T CELL-NEGATIVE, | | RAG1 |
| 603554 | OMENN SYNDROME | | RAG1 |
| 601457 | SEVERE COMBINED IMMUNODEFICIENCY, AUTOSOMAL RECESSIVE, T CELL-NEGATIVE, | | RAG2 |
| 603554 | OMENN SYNDROME | | RAG2 |
| 208150 | FETAL AKINESIA DEFORMATION SEQUENCE | FADS | RAPSN |
| 257320 | LISSENCEPHALY 2 | LIS2 | RELN |
| 612015 | CONGENITAL DISORDER OF GLYCOSYLATION, TYPE In | CDG1N | RFT1 |
| 250250 | CARTILAGE-HAIR HYPOPLASIA | CHH | RMRP |
| 607095 | ANAUXETIC DYSPLASIA | | RMRP |
| 610333 | AICARDI-GOUTIERES SYNDROME 4 | | RNASEH2A |
| 610181 | AICARDI-GOUTIERES SYNDROME 2 | | RNASEH2B |
| 610329 | AICARDI-GOUTIERES SYNDROME 3 | | RNASEH2C |
| 611561 | MECKEL SYNDROME, TYPE 5 | MKS5 | RPGRIP1L |
| 312173 | X-linked mental retardation | RPL10 | RPL10 |
| 300075 | MENTAL RETARDATION X-LINKED 19 INCLUDED | MRX19 | RPS6KA3 |
| 303600 | COFFIN-LOWRY SYNDROME | CLS | RPS6KA3 |
| 612075 | mtDNA depletion, encephalomyopathic form | RRM2B | RRM2B |
| 270550 | SPASTIC ATAXIA, CHARLEVOIX-SAGUENAY TYPE | SACS | SACS |
| 612952 | AICARDI-GOUTIERES SYNDROME 5 | SAMDH1 | SAMDH1 |
| 260400 | SHWACHMAN-DIAMOND SYNDROME | SDS | SBDS |
| 607330 | LATHOSTEROLOSIS | | SC5DL |
| 264350 | PSEUDOHYPOALDOSTERONISM, TYPE I, AUTOSOMAL RECESSIVE | PHA1 | SCNN1A |
| 264350 | PSEUDOHYPOALDOSTERONISM, TYPE I, AUTOSOMAL RECESSIVE | PHA1 | SCNN1B |
| 264350 | PSEUDOHYPOALDOSTERONISM, TYPE I, AUTOSOMAL RECESSIVE | PHA1 | SCNN1G |
| 220110 | Complex IV deficiency | | sco1 |
| 220110 | Complex IV deficiency | | sco2 |
| 604377 | CARDIOENCEPHALOMYOPATHY, FATAL INFANTILE, DUE TO CYTOCHROME c OXIDASE | | SCO2 |
| 602771 | RIGID SPINE MUSCULAR DYSTROPHY 1 | RSMD1 | SEPN1 |
| 265120 | SURFACTANT METABOLISM DYSFUNCTION, PULMONARY, 1 | SMDP1 | SFTPB |
| 267450 | RESPIRATORY DISTRESS SYNDROME IN PREMATURE INFANTS | | SFTPB |
| 267450 | RESPIRATORY DISTRESS SYNDROME IN PREMATURE INFANTS | | SFTPC |
| 252900 | MUCOPOLYSACCHARIDOSIS TYPE IIIA (Sanfilippo type A) | | SGSH |
| 308240 | LYMPHOPROLIFERATIVE SYNDROME, X-LINKED, 1 | XLP1 | SH2D1A |
| 300434 | STOCCO DOS SANTOS X-LINKED MENTAL RETARDATION SYNDROME | | SHROOM4 |
| 248800 | Marinesco-Sjogren Syndrome | | SIL1 |
| 601678 | BARTTER SYNDROME, ANTENATAL, TYPE 1 | | SLC12A1 |
| 218000 | AGENESIS OF THE CORPUS CALLOSUM WITH PERIPHERAL NEUROPATHY | ACCPN | SLC12A6 |
| 300523 | ALLAN-HERNDON-DUDLEY SYNDROME | AHDS | SLC16A2 |
| 269920 | INFANTILE SIALIC ACID STORAGE DISORDER | | SLC17A5 |
| 604369 | SIALURIA, FINNISH TYPE | | SLC17A5 |
| 212140 | CARNITINE DEFICIENCY, SYSTEMIC PRIMARY | CDSP | SLC22A5 |
| 238970 | HYPERORNITHINEMIA-HYPERAMMONEMIA-HOMOCITRULLINURIA SYNDROME | | SLC25A15 |
| 212138 | CARNITINE-ACYLCARNITINE TRANSLOCASE DEFICIENCY | | SLC25A20 |
| 609304 | EPILEPTIC ENCEPHALOPATHY, EARLY INFANTILE, 3 | | SLC25A22 |
| 222600 | DIASTROPHIC DYSPLASIA | | SLC26A2 |
| 256050 | ATELOSTEOGENESIS, TYPE II | AOII | SLC26A2 |
| 600972 | ACHONDROGENESIS, TYPE IB | ACG1B | SLC26A2 |
| 603585 | CONGENITAL DISORDER OF GLYCOSYLATION, TYPE IIf | CDG2F | SLC35A1 |
| 266265 | CONGENITAL DISORDER OF GLYCOSYLATION TYPE IIc | CDG2C | SLC35C1 |
| 269250 | SCHNECKENBECKEN DYSPLASIA | | SLC35D1 |

TABLE S1-continued

| OMIM ID | Disease | Disease Symbol | Gene Symbol |
|---|---|---|---|
| 232220 | GLYCOGEN STORAGE DISEASE Ib | | SLC37A4 |
| 232240 | GLYCOGEN STORAGE DISEASE Ic | | SLC37A4 |
| 217400 | CORNEAL DYSTROPHY AND PERCEPTIVE DEAFNESS | | SLC4A11 |
| 300352 | CREATINE DEFICIENCY SYNDROME, X-LINKED | | SLC6A8 |
| 300243 | MENTAL RETARDATION, X-LINKED ANGELMAN, SYNDROMIC, CHRISTIANSON | | SLC9A6 |
| 253300 | SPINAL MUSCULAR ATROPHY TYPE I | SMA1 | SMN1 |
| 253400 | SPINAL MUSCULAR ATROPHY TYPE III | SMA3 | SMN1 |
| 253550 | SPINAL MUSCULAR ATROPHY TYPE II | SMA2 | SMN1 |
| 257200 | NIEMANN-PICK DISEASE, TYPE A | | SMPD1 |
| 607616 | NIEMANN-PICK DISEASE, TYPE B | | SMPD1 |
| 309583 | MENTAL RETARDATION, X-LINKED, SNYDER-ROBINSON TYPE | | SMS |
| 609528 | CEREBRAL DYSGENESIS, NEUROPATHY, ICHTHYOSIS, AND PALMOPLANTAR KERATODERMA | | SNAP29 |
| 300123 | MENTAL RETARDATION, X-LINKED, WITH PANHYPOPITUITARISM | | sox3 |
| 300123 | MENTAL RETARDATION, X-LINKED, WITH PANHYPOPITUITARISM | | sox3 |
| 235550 | HEPATIC VENOOCCLUSIVE DISEASE WITH IMMUNODEFICIENCY | VODI | SP110 |
| 264600 | PSEUDOVAGINAL PERINEOSCROTAL HYPOSPADIAS; PPSH | | SRD5A2 |
| 611715 | Autosomal mental retardation CDG 1Q | SRD5A3 | SRD5A3 |
| 606494 | Autosomal mental retardation | | ST3GAL3 |
| 609056 | AMISH INFANTILE EPILEPSY SYNDROME | | ST3GAL5 |
| 201710 | LIPOID CONGENITAL ADRENAL HYPERPLASIA | CAH | STAR |
| 209950 | ATYPICAL MYCOBACTERIOSIS, FAMILIAL | | STAT1 |
| 612783 | IMMUNE DYSFUNCTION WITH T-CELL INACTIVATION DUE TO CALCIUM ENTRY DEFECT 2 | STIM1 | STIM1 |
| 601186 | MICROPHTHALMIA, SYNDROMIC 9 (Matthew-Wood syndrome) | MCOPS9 | STRA6 |
| 603552 | HEMOPHAGOCYTIC LYMPHOHISTIOCYTOSIS, FAMILIAL, 4 | FHL4 | STX11 |
| 613101 | HEMOPHAGOCYTIC LYMPHOHISTIOCYTOSIS, FAMILIAL, 5 | FHL5 | STXBP2 |
| 612073 | mtDNA depletion, encephalomyopathic form | SUCLA2 | SUCLA2 |
| 245400 | LACTIC ACIDOSIS, FATAL INFANTILE (mtDNA depletion) | | SUCLG1 |
| 272300 | SULFOCYSTEINURIA | | SUOX |
| 256000 | LEIGH SYNDROME | LS | SURF1 |
| 300802 | MENTAL RETARDATION X-LINKED SYP-RELATED | SYP | SYP |
| 300069 | CARDIOMYOPATHY, DILATED, 3A | CMD3A | TAZ |
| 302060 | BARTH SYNDROME | BTHS | TAZ |
| 241410 | HYPOPARATHYROIDISM-RETARDATION-DYSMORPHISM SYNDROME | HRD | TBCE |
| 259700 | OSTEOPETROSIS, AUTOSOMAL RECESSIVE 1 | OPTB1 | TCIRG1 |
| 242300 | ICHTHYOSIS, LAMELLAR, 1 | LI1 | TGM1 |
| 605407 | SEGAWA SYNDROME, AUTOSOMAL RECESSIVE | | TH |
| 311150 | OPTICOACOUSTIC NERVE ATROPHY WITH DEMENTIA | | TIMM8A |
| 609560 | MITOCHONDRIAL DNA DEPLETION SYNDROME, MYOPATHIC FORM | | TK2 |
| 613002 | HERPES SIMPLEX ENCEPHALITIS, SUSCEPTIBILITY TO, 2 | TLR3 | TLR3 |
| 610688 | JOUBERT SYNDROME 6 | JBTS6 | TMEM67 |
| 239000 | PAGET DISEASE, JUVENILE | | TNFRSF11B |
| 204500 | NEURONAL CEROID LIPOFUSCINOSIS 2 | CLN2 | TPP1 |
| 613192 | MENTAL RETARDATION AUTOSOMAL RECESSIVE 13 | MRT13 | TRAPPC9 |
| 225750 | AICARDI-GOUTIERES SYNDROME 1 | AGS1 | TREX1 |
| 253250 | MULIBREY NANISM | | TRIM37 |
| 225753 | PONTOCEREBELLAR HYPOPLASIA TYPE 4 | PCH4 | TSEN54 |
| 277470 | PONTOCEREBELLAR HYPOPLASIA TYPE 2A | PCH2A | TSEN54 |
| 610505 | COMBINED OXIDATIVE PHOSPHORYLATION DEFICIENCY 3 | COXPD3 | TSFM |
| 275100 | HYPOTHYROIDISM, CONGENITAL, NONGOITROUS, 4 | CHNG4 | TSHB |
| 608800 | SUDDEN INFANT DEATH WITH DYSGENESIS OF THE TESTES SYNDROME | SIDDT | TSPYL1 |
| 277460 | VITAMIN E, FAMILIAL ISOLATED DEFICIENCY OF | VED | TTPA |
| 611603 | LISSENCEPHALY 3 | | TUBA1a |
| 610678 | COMBINED OXIDATIVE PHOSPHORYLATION DEFICIENCY 4 | TUFM | TUFM |
| 611093 | MENTAL RETARDATION AUTOSOMAL RECESSIVE 7 | MRT7 | TUSC3 |
| 209950 | ATYPICAL MYCOBACTERIOSIS, FAMILIAL | | TYK2 |
| 603041 | MITOCHONDRIAL NEUROGASTROINTESTINAL ENCEPHALOPATHY SYNDROME | MNGIE | TYMP |
| 301830 | SPINAL MUSCULAR ATROPHY, X-LINKED 2 | SMAX2 | UBA1 |
| 312180 | MENTAL RETARDATION X-LINKED SYNDROMIC UBE2A-RELATED | UBE2A | UBE2A |
| 243800 | JOHANSON-BLIZZARD SYNDROME | JBS | UBR1 |
| 608898 | HEMOPHAGOCYTIC LYMPHOHISTIOCYTOSIS, FAMILIAL, 3 | FHL3 | UNC13D |
| 610551 | HERPES SIMPLEX ENCEPHALITIS, SUSCEPTIBILITY TO, 1 | | UNC93B1 |
| 300676 | MENTAL RETARDATION, X-LINKED, SYNDROMIC 14 | MRX14 | UPF3B |
| 124000 | MITOCHONDRIAL COMPLEX III DEFICIENCY | | UQCRB |
| 124000 | MITOCHONDRIAL COMPLEX III DEFICIENCY | | UQCRQ |
| 263700 | PORPHYRIA, CONGENITAL ERYTHROPOIETIC | | UROS |

TABLE S1-continued

| OMIM ID | Disease | Disease Symbol | Gene Symbol |
|---|---|---|---|
| 276904 | USHER SYNDROME, TYPE IC | USH1C | USH1C |
| 606943 | USHER SYNDROME, TYPE IG | USH1G | USH1G |
| 276901 | USHER SYNDROME, TYPE IIA | USH2A | USH2A |
| 277440 | VITAMIN D-DEPENDENT osteopenia, TYPE II | | VDR |
| 613404 | ARTHROGRYPOSIS, RENAL DYSFUNCTION, AND CHOLESTASIS 2 | ARCS2 | VIPAR |
| 224050 | CEREBELLAR HYPOPLASIA AND MENTAL RETARDATION WITH OR WITHOUT QUADRUPEDAL | | VLDLR |
| 216550 | COHEN SYNDROME | COH1 | VPS13B |
| 208085 | ARTHROGRYPOSIS, RENAL DYSFUNCTION, AND CHOLESTASIS | ARCS1 | VPS33B |
| 301000 | WISKOTT-ALDRICH SYNDROME | WAS | WAS |
| 257980 | ODONTOONYCHODERMAL DYSPLASIA | OODD | WNT10A |
| 273395 | TETRA-AMELIA, AUTOSOMAL RECESSIVE | | WNT3 |
| 228930 | FIBULAR APLASIA OR HYPOPLASIA, FEMORAL BOWING AND POLY-, SYN-, AND | | WNT7A |
| 276820 | ULNA AND FIBULA, ABSENCE OF, WITH SEVERE LIMB DEFICIENCY | | WNT7A |
| 277300 | SPONDYLOCOSTAL DYSOSTOSIS, AUTOSOMAL RECESSIVE 1 | SCDO1 | WNT7A |
| 300635 | LYMPHOPROLIFERATIVE SYNDROME, X-LINKED, 2 | XLP2 | XIAP |
| 278700 | XERODERMA PIGMENTOSUM, COMPLEMENTATION GROUP A | XPA | XPA |
| 278800 | DE SANCTIS-CACCHIONE SYNDROME | | XPA |
| 278720 | XERODERMA PIGMENTOSUM, COMPLEMENTATION GROUP C | | XPC |
| 300799 | MENTAL RETARDATION X-LINKED SYNDROMIC ZDHHC9-RELATED | ZDHHC9 | ZDHHC9 |
| 306955 | HETEROTAXY, VISCERAL, 1, X-LINKED | HTX1 | ZIC3 |
| 275210 | TIGHT SKIN CONTRACTURE SYNDROME, LETHAL | | ZMPSTE24 |
| 608612 | MANDIBULOACRAL DYSPLASIA WITH TYPE B LIPODYSTROPHY | MADB | ZMPSTE24 |
| 314995 | MENTAL RETARDATION X-LINKED 89 | MRX89 | ZNF41 |
| 229200 | BRITTLE CORNEA SYNDROME (Ehlers-Danlos syndrome type VIB) | BCS | ZNF469 |
| 300573 | MENTAL RETARDATION X-LINKED 92 | MRX92 | ZNF674 |
| 300803 | MENTAL RETARDATION X-LINKED ZNF711-RELATED | ZNF711 | ZNF711 |

The exome and CMH-Dx1 methods utilized Illumina TruSeq enrichment and HiSeq 2000 sequencing and took about 19 days. In contrast, rapid WGS did not use target enrichment, was performed with the HiSeq 2500 instrument and took about 50 hours. Samples CMH064, UDT002 and UDT173 were sequenced using these three methods and variants were detected with a single alignment method (the Genomic Short-read Nucleotide Alignment Program, GSNAP) and variant caller (the Genome Analysis Tool Kit, GATK). In sample CMH064, rapid WGS detected 96.0% of the variants identified by CMH-Dx1 and 99.4% of the variants identified by both methods had identical genotypes, indicating that rapid WGS is highly concordant with established clinical sequencing methods. In contrast, analysis of the rapid WGS dataset from sample CMH064 with three different alignment and variant detection methods (GSNAP/GATK, the Illumina CASAVA alignment tool, and BWA, the Burrows-Wheeler Alignment tool) revealed surprising differences between the variants detected. Only about 80% of the variants detected using GATK/GSNAP or BWA were also detected with CASAVA as show below in Table S2.

There was good concordance between the genotypes of variants detected by rapid WGS (using the HiSeq 2500 and CASAVA) and targeted sequencing (using exome enrichment, the HiSeq 2000 and GATK/GSNAP) was 99.48% (UDT002), 99.93% (UDT173), and 99.74% (CMH064), further showing that rapid WGS is highly concordant with an established genotyping method. In subsequent studies, the rapid WGS technique used CASAVA for alignment and variant detection.

Figure 4:
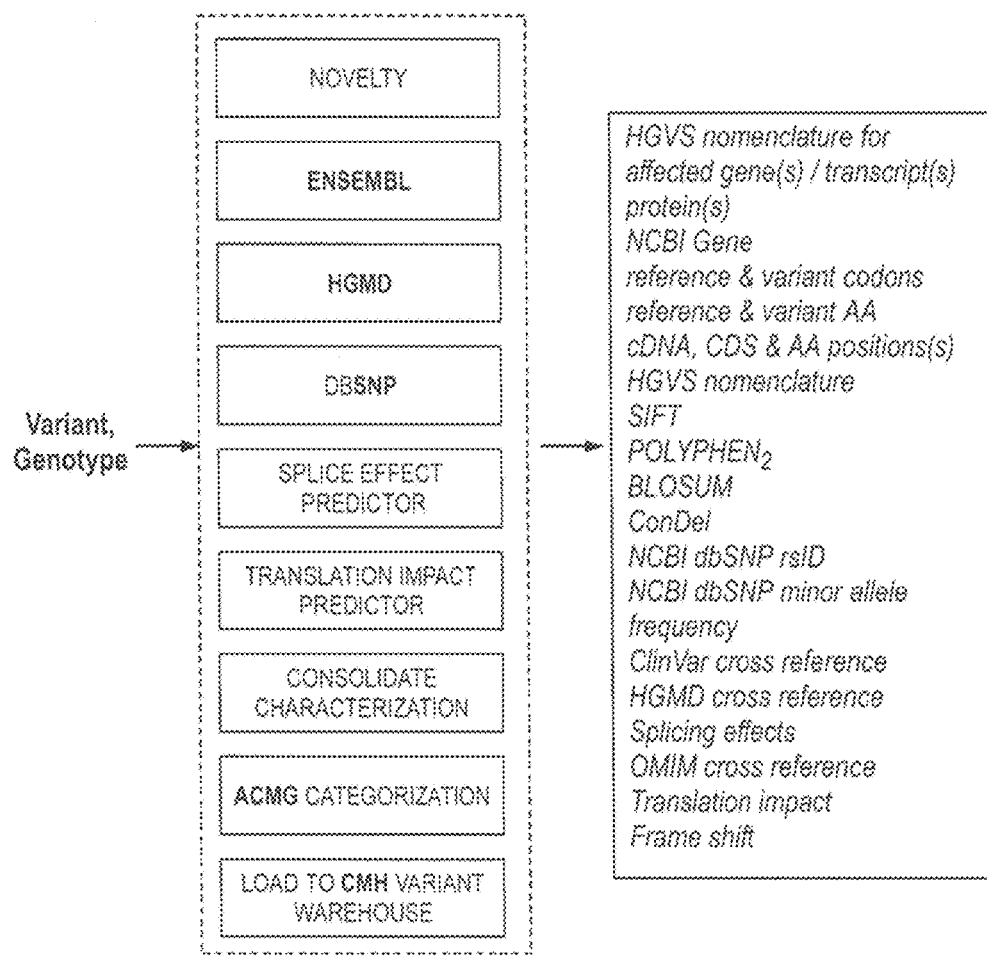
FIG. 4 is an illustration of the present system for the automated variant characterization by RUNES (Rapid Understanding of Nucleotide variant Effect Software)

Genomic variants were characterized with respect to functional consequence and zygosity with a new software pipeline (Rapid Understanding of Nucleotide variant Effect Software, RUNES shown in FIG. 4 as further described below) that analysed each sample in 2.5 hours. Samples contained a mean of 4.00±0.20 million (SD) genomic variants, of which a mean of 1.87±0.09 million (SD) were associated with protein-encoding genes (Table 1). Less than 1% of these variants (mean 10,848±523 SD) were also of a functional class that could potentially be disease causative (shown in Table 1). Of these, about 14% (mean 1,530±518 SD) had an allele frequency that was sufficiently low to be

TABLE S2

| Alignment Method 1 | Alignment Method 2 | Variants Detected By Both Methods | % Variants Detected By Both Methods | Variants Unique to Method 1 | % Variants Unique to Method 1 | Variants Unique to Method 2 | % Variants Unique to Method 2 |
|---|---|---|---|---|---|---|---|
| BWA | CASAVA | 3,505,141 | 78.7 | 466,203 | 10.5 | 482,418 | 10.8 |
| GSNAP | CASAVA | 3,607,308 | 80.3 | 506,910 | 11.3 | 380,251 | 8.5 |
| BWA | GSNAP | 3,766,179 | 87.2 | 205,165 | 4.7 | 348,039 | 8.1 | a candidate for being causative in an uncommon disease (<1% allele frequency in 836 individuals). Lastly, of these, about 71% (mean 1,083±240 SD) were also of a functional class that was likely to be disease causative (American College of Medical Genetics (ACMG) Categories 1 to 3) (shown in Table 1). This set of variants was evaluated for disease causality in each patient, with priority given to variants within the candidate genes that had been nominated by an individual patient presentation.

Retrospective Analyses

The following retrospective analyses are performed and the results reported to show the uniqueness and viability of the present system. Patient UDT002 was a male who presented at 13 months of age with hypotonia, developmental regression. Brain magnetic resonance imaging (MRI) showed diffuse white matter changes suggesting leukodystrophy. 352 disease genes were nominated by one of the three clinical terms hypotonia, developmental regression, or leukodystrophy; 150 disease genes were nominated by two terms, and nine disease genes were nominated by all three terms as shown in Table S3 below.

TABLE S3

| Gene | Clinical Term(s) | Disease |
|---|---|---|
| ERCC6 | ID LD hypotonia | CEREBROOCULOFACIOSKELETAL SYNDROME 1 |
| FAM126A | ID LD hypotonia | LEUKODYSTROPHY, HYPOMYELINATING, 5 |
| PEX1 | ID LD hypotonia | ZELLWEGER SYNDROME ADRENOLEUKODYSTROPHY |
| PEX10 | ID LD hypotonia | ADRENOLEUKODYSTROPHY, AUTOSOMAL NEONATAL FORM |
| PEX13 | ID LD hypotonia | ADRENOLEUKODYSTROPHY, AUTOSOMAL NEONATAL FORM |
| PEX26 | ID LD hypotonia | ADRENOLEUKODYSTROPHY, AUTOSOMAL NEONATAL FORM |
| PEX5 | ID LD hypotonia | ADRENOLEUKODYSTROPHY, AUTOSOMAL NEONATAL FORM |
| PLP1 | ID LD hypotonia | PELIZAEUS-MERZBACHER DISEASE |
| PSAP | ID LD hypotonia | COMBINED SAPOSIN DEFICIENCY METACHROMATIC LEUKODYSTROPHY |
| ABCD1 | ID LD | ADRENOLEUKODYSTROPHY |
| ACAD9 | ID hypotonia | DEFICIENCY OF ACYL-CoA DEHYDROGENASE FAMILY MEMBER 9 |
| ACOX1 | ID hypotonia | PEROXISOMAL ACYL-CoA OXIDASE DEFICIENCY |
| ADA | ID hypotonia | SEVERE COMBINED IMMUNODEFICIENCY, AUT REC, T CELL-NEGATIVE, |
| AHI1 | ID hypotonia | JOUBERT SYNDROME 3 |
| ALDH5A1 | ID hypotonia | SUCCINIC SEMIALDEHYDE DEHYDROGENASE DEFICIENCY |
| ALDH7A1 | ID hypotonia | EPILEPSY, PYRIDOXINE-DEPENDENT |
| ALG1 | ID hypotonia | CONGENITAL DISORDER OF GLYCOSYLATION, TYPE Ik |
| ALG12 | ID hypotonia | CONGENITAL DISORDER OF GLYCOSYLATION TYPE Ig |
| ALG2 | ID hypotonia | CONGENITAL DISORDER OF GLYCOSYLATION TYPE Ii |
| ALG3 | ID hypotonia | CONGENITAL DISORDER OF GLYCOSYLATION, TYPE Id; CDG1D |
| ALG6 | ID hypotonia | CONGENITAL DISORDER OF GLYCOSYLATION TYPE Ic |
| ALG9 | ID hypotonia | CONGENITAL DISORDER OF GLYCOSYLATION, TYPE Il |
| AMT | ID hypotonia | GLYCINE ENCEPHALOPATHY |
| AP1S2 | ID hypotonia | MENTAL RETARDATION, X-LINKED 59 |
| ARSA | ID LD | METACHROMATIC LEUKODYSTROPHY |
| ASPA | ID hypotonia | CANAVAN DISEASE |
| ATP6V0A2 | ID hypotonia | CUTIS LAXA, AUTOSOMAL RECESSIVE, TYPE II |
| ATRX | ID hypotonia | THALASSEMIA/ID, NONDELETION TYPE, X-LINKED |
| B4GALT1 | ID hypotonia | CONGENITAL DISORDER OF GLYCOSYLATION TYPE IId |
| BCKDHA | ID hypotonia | MAPLE SYRUP URINE DISEASE Type Ia |
| BCKDHB | ID hypotonia | BRANCHED-CHAIN KETO ACID DEHYDROGENASE E1, BETA POLYPEPTIDE |
| BCS1L | ID hypotonia | MITOCHONDRIAL COMPLEX III DEFICIENCY |
| BRWD3 | ID hypotonia | MENTAL RETARDATION, X-LINKED 93 |
| BTD | ID hypotonia | BIOTINIDASE DEFICIENCY |
| C10ORF2 | ID hypotonia | INFANTILE-ONSET SPINOCEREBELLAR ATAXIA |
| CEP290 | ID hypotonia | JOUBERT SYNDROME 5 |
| CLN3 | ID LD | NEURONAL CEROID LIPOFUSCINOSIS 3 |
| CLN5 | ID LD | NEURONAL CEROID LIPOFUSCINOSIS 5 |
| CLN6 | ID LD | CEROID LIPOFUSCINOSIS, NEURONAL, 6 |
| CLN8 | ID LD | CEROID LIPOFUSCINOSIS, NEURONAL, 8 |
| COG1 | ID hypotonia | CONGENITAL DISORDER OF GLYCOSYLATION TYPE IIg |
| COG7 | ID hypotonia | CONGENITAL DISORDER OF GLYCOSYLATION, TYPE IIe |
| COG8 | ID hypotonia | CONGENITAL DISORDER OF GLYCOSYLATION TYPE IIh |
| COX10 | ID hypotonia | Complex IV deficiency |
| COX15 | ID hypotonia | Complex IV deficiency |
| COX6B1 | ID hypotonia | Complex IV deficiency |
| CPT1A | ID hypotonia | CARNITINE PALMITOYLTRANSFERASE I DEFICIENCY |
| CTSD | ID LD | CEROID LIPOFUSCINOSIS, NEURONAL, 10 |
| DBT | ID hypotonia | MSUD type 2 |
| DCX | ID hypotonia | LISSENCEPHALY, X-LINKED, 1 |
| DGUOK | ID hypotonia | MITOCHONDRIAL DNA DEPLETION SYNDROME, HEPATOCEREBRAL FORM |
| DLD | ID hypotonia | DIHYDROLIPOAMIDE DEHYDROGENASE DEFICIENCY |
| DOLK | ID hypotonia | CONGENITAL DISORDER OF GLYCOSYLATION TYPE Im |
| DPAGT1 | ID hypotonia | CONGENITAL DISORDER OF GLYCOSYLATION, TYPE Ij |
| DPM1 | ID hypotonia | CONGENITAL DISORDER OF GLYCOSYLATION, TYPE Ie |
| DPYD | ID hypotonia | DIHYDROPYRIMIDINE DEHYDROGENASE |
| ETFA | ID hypotonia | MULTIPLE ACYL-CoA DEHYDROGENASE DEFICIENCY |

TABLE S3-continued

| Gene | Clinical Term(s) | Disease |
|---|---|---|
| ETFB | ID hypotonia | MULTIPLE ACYL-CoA DEHYDROGENASE DEFICIENCY |
| ETFDH | ID hypotonia | MULTIPLE ACYL-CoA DEHYDROGENASE DEFICIENCY |
| ETHE1 | ID hypotonia | ENCEPHALOPATHY, ETHYLMALONIC |
| FASTKD2 | ID hypotonia | Complex IV deficiency |
| FH | ID hypotonia | FUMARASE DEFICIENCY |
| FKRP | ID hypotonia | MUSCULAR DYSTROPHY, CONGENITAL, 1C |
| FKTN | ID hypotonia | FUKUYAMA CONGENITAL MUSCULAR DYSTROPHY |
| GALC | ID LD | KRABBE DISEASE |
| GCDH | ID hypotonia | GLUTARIC ACIDEMIA I |
| GCSH | ID hypotonia | GLYCINE ENCEPHALOPATHY |
| GJC2 | ID LD | LEUKODYSTROPHY, HYPOMYELINATING, 2 |
| GLDC | ID hypotonia | GLYCINE ENCEPHALOPATHY |
| GNPTAB | ID hypotonia | MUCOLIPIDOSIS II ALPHA/BETA |
| HADH | ID hypotonia | 3-HYDROXYACYL-CoA DEHYDROGENASE DEFICIENCY |
| HADHA | ID hypotonia | HYDROXYACYL-CoA DEHYDROGENASE |
| HADHB | ID hypotonia | TRIFUNCTIONAL PROTEIN DEFICIENCY |
| HLCS | ID hypotonia | HOLOCARBOXYLASE SYNTHETASE DEFICIENCY |
| HSD17B10 | ID hypotonia | MENTAL RETARDATION, X-LINKED, SYNDROMIC 10 |
| HSD17B4 | ID hypotonia | D-BIFUNCTIONAL PROTEIN DEFICIENCY |
| IL1RAPL1 | ID hypotonia | MENTAL RETARDATION, X-LINKED 21 |
| L1CAM | ID hypotonia | HYDROCEPHALUS DUE TO CONGENITAL STENOSIS OF AQUEDUCT OF SYLVIUS |
| LAMA2 | ID hypotonia | MUSCULAR DYSTROPHY, CONGENITAL MEROSIN-DEFICIENT, 1A |
| LAMB2 | ID hypotonia | PIERSON SYNDROME |
| LARGE | ID hypotonia | MUSCULAR DYSTROPHY, CONGENITAL, TYPE 1D |
| LRPPRC | ID hypotonia | LEIGH SYNDROME, FRENCH-CANADIAN TYPE |
| MCOLN1 | ID hypotonia | MUCOLIPIDOSIS IV |
| MECP2 | ID hypotonia | RETT SYNDROME |
| MED12 | ID hypotonia | LUJAN-FRYNS SYNDROME |
| MFSD8 | ID LD | CEROID LIPOFUSCINOSIS, NEURONAL, 7 |
| MGAT2 | ID hypotonia | CONGENITAL DISORDER OF GLYCOSYLATIO, TYPE IIa |
| MMAA | ID hypotonia | METHYLMALONIC ACIDURIA, cblA TYPE |
| MMAB | ID hypotonia | METHYLMALONIC ACIDURIA, cblB TYPE |
| MMACHC | ID hypotonia | METHYLMALONIC ACIDURIA AND HOMOCYSTINURIA, cblC TYPE |
| MOGS | ID hypotonia | CONGENITAL DISORDER OF GLYCOSYLATION TYPE IIb |
| MPDU1 | ID hypotonia | CONGENITAL DISORDER OF GLYCOSYLATION, TYPE If |
| MPI | ID hypotonia | CONGENITAL DISORDER OF GLYCOSYLATION, TYPE Ib |
| MPV17 | ID hypotonia | NAVAJO NEUROHEPATOPATHY MITOCHONDRIAL DNA DEPLETION, HEPATOCEREBRAL |
| MRPS16 | ID hypotonia | COMBINED OXIDATIVE PHOSPHORYLATION DEFICIENCY 2 |
| MRPS22 | ID hypotonia | COMBINED OXIDATIVE PHOSPHORYLATION DEFICIENCY 5 |
| MUT | ID hypotonia | METHYLMALONIC ACIDURIA DUE TO METHYLMALONYL-CoA MUTASE DEFICIENCY |
| MYO5A | ID hypotonia | GRISCELLI SYNDROME, TYPE 1 |
| NPC2 | ID hypotonia | NIEMANN-PICK DISEASE, TYPE C2 |
| NPHP1 | ID hypotonia | JOUBERT SYNDROME 4 |
| OCRL | ID hypotonia | LOWE OCULOCEREBRORENAL SYNDROME |
| OFD1 | ID hypotonia | SIMPSON-GOLABI-BEHMEL SYNDROME, TYPE 2 |
| OPHN1 | ID hypotonia | ID, XLR, W CEREBELLAR HYPOPLASIA & DISTINCTIVE FACIAL APPEARANCE |
| PC | ID hypotonia | PYRUVATE CARBOXYLASE DEFICIENCY |
| PCCA | ID hypotonia | PROPIONIC ACIDEMIA |
| PCCB | ID hypotonia | PROPIONIC ACIDEMIA |
| PDHA1 | ID hypotonia | LEIGH SYNDROME, X-LINKED |
| PDHX | ID hypotonia | PYRUVATE DEHYDROGENASE E3-BINDING PROTEIN DEFICIENCY |
| PDP1 | ID hypotonia | PYRUVATE DEHYDROGENASE PHOSPHATASE DEFICIENCY |
| PEX12 | ID hypotonia | ZELLWEGER SYNDROME |
| PLA2G6 | ID hypotonia | INFANTILE NEUROAXONAL DYSTROPHY |
| PMM2 | ID hypotonia | CONGENITAL DISORDER OF GLYCOSYLATION TYPE Ia |
| PNPO | ID hypotonia | PYRIDOXAMINE 5-PRIME-PHOSPHATE OXIDASE DEFICIENCY |
| POLG | ID hypotonia | ALPERS DIFFUSE DEGENERATION OF CEREBRAL GRAY MATTER W. HEPATIC CIRRHOSIS |
| POMGNT1 | ID hypotonia | MUSCLE-EYE-BRAIN DISEASE |
| POMT1 | ID hypotonia | WALKER-WARBURG SYNDROME |
| POMT2 | ID hypotonia | WALKER-WARBURG SYNDROME |
| PPT1 | ID LD | NEURONAL CEROID LIPOFUSCINOSIS 1 |
| PRPS1 | ID hypotonia | ARTS SYNDROME |
| RAB3GAP1 | ID hypotonia | WARBURG MICRO SYNDROME |
| RELN | ID hypotonia | LISSENCEPHALY 2 |
| RFT1 | ID hypotonia | CONGENITAL DISORDER OF GLYCOSYLATION, TYPE In |
| RNASEH2A | ID LD | AICARDI-GOUTIERES SYNDROME 4 |
| RNASEH2B | ID LD | AICARDI-GOUTIERES SYNDROME 2 |
| RNASEH2C | ID LD | AICARDI-GOUTIERES SYNDROME 3 |
| RRM2B | ID hypotonia | mtDNA depletion, encephalomyopathic form |
| SAMHD1 | ID LD | AICARDI-GOUTIERES SYNDROME 5 |
| SC5DL | ID hypotonia | LATHOSTEROLOSIS |

TABLE S3-continued

| Gene | Clinical Term(s) | Disease |
| --- | --- | --- |
| SCO1 | ID hypotonia | Complex IV deficiency |
| SCO2 | ID hypotonia | CARDIOENCEPHALOMYOPATHY, FATAL INFANTILE, DUE TO CYTOCHROME c OXIDASE |
| SIL1 | ID hypotonia | Marinesco-Sjogren Syndrome |
| SLC16A2 | ID hypotonia | ALLAN-HERNDON-DUDLEY SYNDROME |
| SLC17A5 | ID hypotonia | INFANTILE SIALIC ACID STORAGE DISORDER |
| SLC22A5 | ID hypotonia | CARNITINE DEFICIENCY, SYSTEMIC PRIMARY |
| SLC25A15 | ID hypotonia | HYPERORNITHINEMIA-HYPERAMMONEMIA-HOMOCITRULLINURIA SYNDROME |
| SLC25A22 | ID hypotonia | EPILEPTIC ENCEPHALOPATHY, EARLY INFANTILE, 3 |
| SLC35C1 | ID hypotonia | CONGENITAL DISORDER OF GLYCOSYLATION TYPE IIc |
| SMPD1 | ID hypotonia | NIEMANN-PICK DISEASE, TYPE A |
| SMS | ID hypotonia | MENTAL RETARDATION, X-LINKED, SNYDER-ROBINSON TYPE |
| SNAP29 | ID hypotonia | CEREBRAL DYSGENESIS, NEUROPATHY, ICHTHYOSIS, PALMOPLANTAR KERATODERMA |
| ST3GAL5 | ID hypotonia | AMISH INFANTILE EPILEPSY SYNDROME |
| STRA6 | ID hypotonia | MICROPHTHALMIA, SYNDROMIC 9 (Matthew-Wood syndrome) |
| SUCLA2 | ID hypotonia | mtDNA depletion, encephalomyopathic form |
| SUCLG1 | ID hypotonia | LACTIC ACIDOSIS, FATAL INFANTILE (mtDNA depletion) |
| SUOX | ID hypotonia | SULFOCYSTEINURIA |
| SURF1 | ID hypotonia | LEIGH SYNDROME |
| TH | ID hypotonia | SEGAWA SYNDROME, AUTOSOMAL RECESSIVE |
| TMEM67 | ID hypotonia | JOUBERT SYNDROME 6 |
| TPP1 | ID LD | NEURONAL CEROID LIPOFUSCINOSIS 2 |
| TREX1 | ID LD | AICARDI-GOUTIERES SYNDROME 1 |
| TSFM | ID hypotonia | COMBINED OXIDATIVE PHOSPHORYLATION DEFICIENCY 3 |
| TSHB | ID hypotonia | HYPOTHYROIDISM, CONGENITAL, NONGOITROUS, 4 |
| TUFM | ID hypotonia | COMBINED OXIDATIVE PHOSPHORYLATION DEFICIENCY 4 |
| TYMP | ID LD | MITOCHONDRIAL NEUROGASTROINTESTINAL ENCEPHALOPATHY SYNDROME |
| UQCRB | ID hypotonia | MITOCHONDRIAL COMPLEX III DEFICIENCY |
| UQCRQ | ID hypotonia | MITOCHONDRIAL COMPLEX III DEFICIENCY |
| VLDLR | ID hypotonia | CEREBELLAR HYPOPLASIA AND ID WITH/WITHOUT QUADRUPEDAL |
| VPS13B | ID hypotonia | COHEN SYNDROME |
| VPS33B | ID hypotonia | ARTHROGRYPOSIS, RENAL DYSFUNCTION, AND CHOLESTASIS |
| AAAS | ID | ACHALASIA-ADDISONIANISM-ALACRIMA SYNDROME |
| ABCC8 | hypotonia | HYPERINSULINEMIC HYPOGLYCEMIA, FAMILIAL, 1 |
| ACADL | hypotonia | ACYL-CoA DEHYDROGENASE, LONG-CHAIN, DEFICIENCY OF |
| ACADM | hypotonia | ACYL-CoA DEHYDROGENASE, MEDIUM-CHAIN, DEFICIENCY OF |
| ACADVL | hypotonia | ACYL-CoA DEHYDROGENASE, VERY LONG-CHAIN, DEFICIENCY OF |
| ACAT1 | ID | ALPHA-METHYLACETOACETIC ACIDURIA |
| ACSL4 | ID | MENTAL RETARDATION, X-LINKED 68 |
| ADAMTSL2 | ID | GELEOPHYSIC DYSPLASIA |
| ADCK3 | ID | COENZYME Q10 DEFICIENCY |
| AFF2 | ID | MENTAL RETARDATION X-LINKED ASSOCIATED WITH FRAGILE SITE |
| AGPS | ID | RHIZOMELIC CHONDRODYSPLASIA PUNCTATA, TYPE 3 |
| AGTR2 | ID | MENTAL RETARDATION X-LINKED 88 |
| ALDH3A2 | ID | SJOGREN-LARSSON SYNDROME |
| ALG8 | hypotonia | CONGENITAL DISORDER OF GLYCOSYLATION, TYPE Ih |
| ALMS1 | ID | ALSTROM SYNDROME |
| ALS2 | ID | PRIMARY LATERAL SCLEROSIS, JUVENILE |
| AP3B1 | ID | HERMANSKY-PUDLAK SYNDROME 2 |
| APTX | ID | ATAXIA, EARLY-ONSET, WITH oculomotor apraxia AND HYPOALBUMINEMIA |
| ARHGEF6 | ID | MENTAL RETARDATION, X-LINKED 46 |
| ARHGEF9 | ID | HYPEREKPLEXIA AND EPILEPSY |
| ARSB | ID | MUCOPOLYSACCHARIDOSIS TYPE VI MAROTEAUX-LAMY |
| ARSE | ID | CHONDRODYSPLASIA PUNCTATA 1, X-LINKED RECESSIVE |
| ARX | ID | LISSENCEPHALY, X-LINKED, 2 |
| ASL | ID | ARGININOSUCCINIC ACIDURIA |
| ASS1 | ID | CITRULLINEMIA, CLASSIC |
| ATM | ID | ATAXIA-TELANGIECTASIA |
| ATP7A | ID | MENKES DISEASE |
| ATP7B | ID | WILSON DISEASE |
| ATR | ID | SECKEL SYNDROME 1 |
| AUH | ID | 3-METHYLGLUTACONIC ACIDURIA, TYPE I |
| CA2 | ID | OSTEOPETROSIS, AUTOSOMAL RECESSIVE 3 |
| CASK | ID | ID AND MICROCEPHALY WITH PONTINE AND CEREBELLAR HYPOPLASIA |
| CBS | ID | HOMOCYSTINURIA |
| COQ2 | ID | COENZYME Q10 DEFICIENCY |
| COQ9 | ID | COENZYME Q10 DEFICIENCY |
| CPS1 | ID | CARBAMOYL PHOSPHATE SYNTHETASE I DEFICIENCY, HYPERAMMONEMIA DUE TO |
| CPT2 | ID | CARNITINE PALMITOYLTRANSFERASE II DEFICIENCY, INFANTILE |

TABLE S3-continued

| Gene | Clinical Term(s) | Disease |
| --- | --- | --- |
| CRLF1 | ID | CRISPONI SYNDROME |
| CSTB | ID | MYOCLONIC EPILEPSY OF UNVERRICHT AND LUNDBORG |
| CUL4B | ID | MENTAL RETARDATION X-LINKED WITH BRACHYDACTYLY AND MACROGLOSSIA |
| CYP27A1 | ID | CEREBROTENDINOUS XANTHOMATOSIS |
| CYP27B1 | hypotonia | VITAMIN D-DEPENDENT osteopenia, TYPE I |
| DDC | ID | AROMATIC L-AMINO ACID DECARBOXYLASE DEFICIENCY |
| DHCR24 | ID | DESMOSTEROLOSIS |
| DHCR7 | ID | SMITH-LEMLI-OPITZ SYNDROME |
| DKC1 | ID | HOYERAAL-HREIDARSSON SYNDROME |
| DLG3 | ID | MENTAL RETARDATION X-LINKED 90 |
| DNAJC19 | ID | 3-METHYLGLUTACONIC ACIDURIA, TYPE V |
| DNMT3B | ID | IMMUNODEFICIENCY-CENTROMERIC INSTABILITY-FACIAL ANOMALIES SYNDROME |
| EDN3 | ID | WAARDENBURG-SHAH SYNDROME |
| EDNRB | ID | ABCD SYNDROME |
| EFNB1 | ID | CRANIOFRONTONASAL SYNDROME |
| EGR2 | hypotonia | HYPERTROPHIC NEUROPATHY OF DEJERINE-SOTTAS |
| EIF2AK3 | ID | EPIPHYSEAL DYSPLASIA, MULTIPLE, WITH EARLY-ONSET DIABETES MELLITUS |
| EPM2A | ID | MYOCLONIC EPILEPSY OF LAFORA |
| ERCC2 | ID | TRICHOTHIODYSTROPHY, PHOTOSENSITIVE |
| ERCC3 | ID | TRICHOTHIODYSTROPHY, PHOTOSENSITIVE |
| ERCC8 | ID | COCKAYNE SYNDROME, TYPE A |
| ESCO2 | ID | ROBERTS SYNDROME |
| EVC | ID | ELLIS-VAN CREVELD SYNDROME; EVC |
| EVC2 | ID | ELLIS-VAN CREVELD SYNDROME |
| FANCC | ID | Fanconi anemia type C |
| FGD1 | ID | FACIOGENITAL DYSPLASIA |
| FOLR1 | ID | NEURODEGENERATION DUE TO CEREBRAL FOLATE TRANSPORT DEFICIENCY |
| FRAS1 | ID | FRASER SYNDROME |
| FREM2 | ID | FRASER SYNDROME |
| FTSJ1 | ID | MENTAL RETARDATION, X-LINKED 9 |
| FUCA1 | ID | FUCOSIDOSIS |
| GAA | hypotonia | GLYCOGEN STORAGE DISEASE II (pompe) |
| GALT | ID | GALACTOSEMIA |
| GAMT | ID | GUANIDINOACETATE METHYLTRANSFERASE DEFICIENCY |
| GBA | ID | GAUCHER DISEASE II |
| GBE1 | hypotonia | GLYCOGEN STORAGE DISEASE IV |
| GDI1 | ID | MENTAL RETARDATION, X-LINKED 41, 48 |
| GFM1 | ID | COMBINED OXIDATIVE PHOSPHORYLATION DEFICIENCY 1 |
| GLB1 | ID | GM1-GANGLIOSIDOSIS TYPE II |
| GRIK2 | ID | MENTAL RETARDATION AUTOSOMAL RECESSIVE 6 |
| GSS | ID | GLUTATHIONE SYNTHETASE DEFICIENCY |
| GTF2H5 | ID | TRICHOTHIODYSTROPHY, PHOTOSENSITIVE |
| GUSB | ID | MUCOPOLYSACCHARIDOSIS TYPE VII SLY SYNDROME |
| HAX1 | ID | neutropenia, SEVERE CONGENITAL, AUTOSOMAL RECESSIVE 3 |
| HEXA | ID | TAY-SACHS DISEASE |
| HEXB | ID | SANDHOFF DISEASE |
| HGSNAT | ID | MUCOPOLYSACCHARIDOSIS TYPE IIIC (Sanfilippo type c) |
| HIBCH | ID | BETA-HYDROXYISOBUTYRYL CoA DEACYLASE, DEFICIENCY OF |
| HMGCL | ID | 3-HYDROXY-3-METHYLGLUTARYL-CoA LYASE DEFICIENCY |
| HPRT1 | ID | LESCH-NYHAN SYNDROME |
| HUWE1 | ID | MENTAL RETARDATION X-LINKED SYNDROMIC TURNER TYPE |
| IDS | ID | MUCOPOLYSACCHARIDOSIS TYPE II |
| IDUA | ID | HURLER SYNDROME |
| IKBKAP | hypotonia | NEUROPATHY, HEREDITARY SENSORY AND AUTONOMIC, TYPE III |
| IVD | ID | ISOVALERIC ACIDEMIA |
| KCNJ1 | ID | BARTTER SYNDROME, ANTENATAL, TYPE 2 |
| KDM5C | ID | MENTAL RETARDATION, X-LINKED, SYNDROMIC |
| LHX3 | ID | PITUITARY HORMONE DEFICIENCY, COMBPNED, 3; CPHD3 |
| LIFR | hypotonia | STUVE-WIEDEMANN SYNDROME |
| LRP2 | ID | DONNAI-BARROW SYNDROME |
| LYST | ID | CHEDIAK HIGASHI SYNDROME |
| MAN2B1 | ID | MANNOSIDOSIS, ALPHA B, LYSOSOMAL |
| MBTPS2 | ID | ICHTHYOSIS FOLLICULARIS, ATRICHIA, AND PHOTOPHOBIA SYNDROME |
| MID1 | ID | OPITZ GBBB SYNDROME, X-LINKED |
| MKS1 | ID | MECKEL SYNDROME TYPE 1 |
| MLC1 | ID | MEGALENCEPHALIC LEUKOENCEPHALOPATHY WITH SUBCORTICAL CYSTS |
| MOCS1 | ID | MOLYBDENUM COFACTOR DEFICIENCY |
| MOCS2 | ID | MOLYBDENUM COFACTOR DEFICIENCY |
| MPZ | hypotonia | HYPERTROPHIC NEUROPATHY OF DEJERINE-SOTTAS |
| MTM1 | ID | MYOTUBULAR MYOPATHY 1 |
| MVK | ID | MEVALONIC ACIDURIA |
| MYO7A | ID | USHER SYNDROME, TYPE I |

TABLE S3-continued

| Gene | Clinical Term(s) | Disease |
|---|---|---|
| NAGS | ID | N-ACETYLGLUTAMATE SYNTHASE DEFICIENCY |
| NBN | ID | NIJMEGEN BREAKAGE SYNDROME |
| NDP | ID | NORRIE DISEASE |
| NDUFA1 | ID | Complex I Deficiency |
| NDUFA7 | ID | Complex I Deficiency |
| NDUFAF2 | ID | Complex I Deficiency |
| NDUFAF4 | ID | Complex I Deficiency |
| NDUFS3 | ID | Complex I Deficiency |
| NDUFS4 | ID | Complex I Deficiency |
| NDUFS5 | ID | Complex I Deficiency |
| NDUFS6 | ID | Complex I Deficiency |
| NDUFS7 | ID | Complex I Deficiency |
| NDUFS8 | ID | Complex I Deficiency |
| NDUFV1 | ID | Complex I Deficiency |
| NEB | hypotonia | NEMALINE MYOPATHY 2 |
| NEU1 | ID | NEURAMINIDASE DEFICIENCY |
| NHLRC1 | ID | MYOCLONIC EPILEPSY OF LAFORA |
| NHS | ID | NANCE-HORAN SYNDROME; NHS |
| NLGN4X | ID | X-linked Asperger syndrome-2 |
| NPC1 | ID | NIEMANN-PICK DISEASE, TYPE C1 |
| NSUN2 | ID | Autosomal mental retardation |
| NTRK1 | ID | INSENSITIVITY TO PAIN, CONGENITAL, WITH ANHIDROSIS |
| NUP62 | ID | STRIATONIGRAL DEGENERATION, INFANTILE |
| NXF5 | ID | X-linked mental retardation |
| OPA3 | ID | 3-@METHYLGLUTACONIC ACIDURIA, TYPE III |
| ORAI1 | hypotonia | IMMUNE DYSFUNCTION WITH T-CELL INACTIVATION DUE TO CALCIUM ENTRY DEFECT 1 |
| OTC | ID | ORNITHINE TRANSCARBAMYLASE DEFICIENCY, HYPERAMMONEMIA DUE TO |
| PAH | ID | PHENYLKETONURIA |
| PAK3 | ID | MENTAL RETARDATION, X-LINKED 30 |
| PANK2 | ID | NEURODEGENERATION WITH BRAIN IRON ACCUMULATION 1 (Hallervorden-Spatz) |
| PCDH19 | ID | EPILEPSY, FEMALE-RESTRICTED, WITH MENTAL RETARDATION |
| PDSS1 | ID | COENZYME Q10 DEFICIENCY |
| PDSS2 | ID | COENZYME Q10 DEFICIENCY |
| PEX7 | ID | RHIZOMELIC CHONDRODYSPLASIA PUNCTATA TYPE 1 |
| PLOD1 | hypotonia | NEVO SYNDROME |
| PMP22 | hypotonia | HYPERTROPHIC NEUROPATHY OF DEJERINE-SOTTAS |
| POR | ID | ANTLEY-BIXLER SYNDROME |
| PQBP1 | ID | RENPENNING SYNDROME 1 |
| PRSS12 | ID | MENTAL RETARDATION, AUTOSOMAL RECESSIVE 1 |
| PRX | hypotonia | HYPERTROPHIC NEUROPATHY OF DEJERINE-SOTTAS |
| RAB23 | ID | CARPENTER SYNDROME |
| RAB27A | ID | GRISCELLI SYNDROME, TYPE 2 |
| RAB39B | ID | MENTAL RETARDATION X-LINKED 72 |
| RAB3GAP2 | ID | MARTSOLF SYNDROME |
| RAPSN | ID | FETAL AKINESIA DEFORMATION SEQUENCE |
| RMRP | ID | ANAUXETIC DYSPLASIA |
| RPGRIP1L | ID | MECKEL SYNDROME, TYPE 5 |
| RPL10 | ID | X-linked mental retardation |
| RPS6KA3 | ID | COFFIN-LOWRY SYNDROME |
| SEPN1 | hypotonia | RIGID SPINE MUSCULAR DYSTROPHY 1 |
| SGSH | ID | MUCOPOLYSACCHARIDOSIS TYPE IIIA (Sanfilippo type A) |
| SHROOM4 | ID | STOCCO DOS SANTOS X-LINKED MENTAL RETARDATION SYNDROME |
| SLC12A1 | ID | BARTTER SYNDROME, ANTENATAL, TYPE 1 |
| SLC12A6 | ID | AGENESIS OF THE CORPUS CALLOSUM WITH PERIPHERAL NEUROPATHY |
| SLC25A20 | ID | CARNITINE-ACYLCARNITINE TRANSLOCASE DEFICIENCY |
| SLC6A8 | ID | CREATINE DEFICIENCY SYNDROME, X-LINKED |
| SLC9A6 | ID | MENTAL RETARDATION, X-LINKED ANGELMAN, SYNDROMIC, CHRISTIANSON |
| SMN1 | hypotonia | SPINAL MUSCULAR ATROPHY TYPE I |
| sox3 | ID | MENTAL RETARDATION, X-LINKED, WITH PANHYPOPITUITARISM |
| SRD5A3 | ID | Autosomal mental retardation CDG 1Q |
| ST3GAL3 | ID | Autosomal mental retardation |
| STIM1 | hypotonia | IMMUNE DYSFUNCTION WITH T-CELL INACTIVATION DUE TO CALCIUM ENTRY DEFECT 2 |
| SYP | ID | MENTAL RETARDATION X-LINKED SYP-RELATED |
| TAZ | ID | BARTH SYNDROME |
| TBCE | ID | HYPOPARATHYROIDISM-RETARDATION-DYSMORPHISM SYNDROME |
| TIMM8A | ID | OPTICOACOUSTIC NERVE ATROPHY WITH DEMENTIA |
| TK2 | hypotonia | MITOCHONDRIAL DNA DEPLETION SYNDROME, MYOPATHIC FORM |
| TRAPPC9 | ID | MENTAL RETARDATION AUTOSOMAL RECESSIVE 13 |

TABLE S3-continued

| Gene | Clinical Term(s) | Disease |
|---|---|---|
| TRIM37 | hypotonia | MULIBREY NANISM |
| TSEN54 | ID | PONTOCEREBELLAR HYPOPLASIA TYPE 2A |
| TSPYL1 | ID | SUDDEN INFANT DEATH WITH DYSGENESIS OF THE TESTES SYNDROME |
| TUBA1a | ID | LISSENCEPHALY 3 |
| TUSC3 | ID | MENTAL RETARDATION AUTOSOMAL RECESSIVE 7 |
| UBA1 | hypotonia | SPINAL MUSCULAR ATROPHY, X-LINKED 2 |
| UBE2A | ID | MENTAL RETARDATION X-LINKED SYNDROMIC UBE2A-RELATED |
| UBR1 | ID | JOHANSON-BLIZZARD SYNDROME |
| UPF3B | ID | MENTAL RETARDATION, X-LINKED, SYNDROMIC 14 |
| UROS | ID | PORPHYRIA, CONGENITAL ERYTHROPOIETIC |
| VDR | hypotonia | VITAMIN D-DEPENDENT osteopenia, TYPE II |
| XPA | ID | XERODERMA PIGMENTOSUM, COMPLEMENTATION GROUP A |
| ZDHHC9 | ID | MENTAL RETARDATION X-LINKED SYNDROMIC ZDHHC9-RELATED |
| ZNF41 | ID | MENTAL RETARDATION X-LINKED 89 |
| ZNF674 | ID | MENTAL RETARDATION X-LINKED 92 |
| ZNF711 | ID | MENTAL RETARDATION X-LINKED ZNF711-RELA |

Only 16 known pathogenic variants had allele frequencies in dbSNP and the cumulative database that were consistent with uncommon disease mutations. Of these, only two variants mapped to the nine candidate genes; the variants were both compound heterozygous (verified by parental testing) substitution mutations in the gene that encodes the a subunit of the lysosomal enzyme hexosaminidase A (HEXA Chr 15:72,641,417T>C (gene symbol, chromosome number, chromosome coordinate, reference nucleotide>variant nucleotide), c.986+3A>G (transcript coordinate, reference nucleotide, variant nucleotide); and Chr15:72,640,388C>T, c.1073+1G>A). The c.986+3A>G alters a 5' exon-flanking nucleotide and is a known mutation that causes Tay-Sachs disease, a debilitating lysosomal storage disorder (TSD, OMIM#272800). The variant had not previously been observed in our database of 651 individuals or dbSNP, which is relevant because mutation databases are contaminated with some common polymorphisms, and these can be distinguished from true mutations on the basis of allele frequency (33). The c.1073+1G>A variant is a known TSD mutation that affects an exonic splice donor site (db-SNP rs76173977). The variant has been observed only once before in our database of 414 samples, which is consistent with an allele frequency of a causative mutation in an orphan genetic disease. Thus, the known diagnosis of TSD was confirmed in patient UDT002 by rapid WGS.

Patient UDT173 was a male who presented at 5 months of age with developmental regression, hypotonia, and seizures. Brain MRI showed dysmyelination, hair shaft analysis revealed pili torti (kinky hair), and serum copper and ceruloplasmin were low. On the basis of this clinical presentation, 276 disease genes matched one of these clinical terms and three matched three terms as shown in Table S4 below.

TABLE S4

| Gene | Search term(s) | Disease(s) |
|---|---|---|
| ABCC8 | epilepsy; hypotonia | HYPERINSULINEMIC HYPOGLYCEMIA, FAMILIAL, 1 |
| ACAD9 | hypotonia | DEFICIENCY OF ACYL-CoA DEHYDROGENASE FAMILY MEMBER 9 |
| ACADL | hypotonia | ACYL-CoA DEHYDROGENASE, LONG-CHAIN, DEFICIENCY OF |
| ACADM | hypotonia | ACYL-CoA DEHYDROGENASE, MEDIUM-CHAIN, DEFICIENCY OF |
| ACADVL | hypotonia | ACYL-CoA DEHYDROGENASE, VERY LONG-CHAIN, DEFICIENCY OF |
| ACOX1 | epilepsy; hypotonia | PEROXISOMAL ACYL-CoA OXIDASE DEFICIENCY |
| ADA | hypotonia | SEVERE COMBINED IMMUNODEFICIENCY, AUT REC, T CELL-NEGATIVE, |
| ADAMTSL2 | epilepsy; | GELEOPHYSIC DYSPLASIA |
| ADCK3 | epilepsy; | COENZYME Q10 DEFICIENCY |
| AGL | dev. motor disorder; | GLYCOGEN STORAGE DISEASE III |
| AGTR2 | epilepsy; | MENTAL RETARDATION X-LINKED 88 |
| AHI1 | hypotonia | JOUBERT SYNDROME 3 |
| ALDH3A2 | epilepsy; | SJOGREN-LARSSON SYNDROME |
| ALDH5A1 | epilepsy; hypotonia | SUCCINIC SEMIALDEHYDE DEHYDROGENASE DEFICIENCY |
| ALDH7A1 | epilepsy; hypotonia | epilepsy;, PYRIDOXINE-DEPENDENT; EPD |
| ALDOB | epilepsy; | FRUCTOSE INTOLERANCE, HEREDITARY |
| ALG1 | hypotonia | CONGENITAL DISORDER OF GLYCOSYLATION, TYPE Ik |
| ALG12 | dev. motor disorder; epilepsy; hypotonia | CONGENITAL DISORDER OF GLYCOSYLATION TYPE Ig |
| ALG2 | epilepsy; hypotonia | CONGENITAL DISORDER OF GLYCOSYLATION TYPE Ii |
| ALG3 | epilepsy; hypotonia | CONGENITAL DISORDER OF GLYCOSYLATION, TYPE Id; CDG1D |
| ALG6 | epilepsy; hypotonia | CONGENITAL DISORDER OF GLYCOSYLATION TYPE Ic |
| ALG8 | epilepsy; hypotonia | CONGENITAL DISORDER OF GLYCOSYLATION, TYPE Ih |
| ALG9 | epilepsy; hypotonia | CONGENITAL DISORDER OF GLYCOSYLATION, TYPE Il |
| ALPL | epilepsy; | HYPOPHOSPHATASIA, CHILDHOOD |
| ALS2 | dev. motor disorder; | JUVENILE AMYOTROPHIC LATERAL SCLEROSIS 2 |
| AMT | epilepsy; hypotonia | GLYCINE ENCEPHALOPATHY |
| ANTXR2 | dev. motor disorder; | HYALINOSIS, INFANTILE SYSTEMIC |

TABLE S4-continued

| Gene | Search term(s) | Disease(s) |
|---|---|---|
| AP1S2 | hypotonia | MENTAL RETARDATION, X-LINKED 59 |
| APTX | dev. motor disorder; epilepsy; | ATAXIA, EARLY-ONSET, oculomotor apraxia, HYPOALBUMINEMIA, CoQ10 DEFICIENCY |
| ARHGEF9 | epilepsy; | HYPEREKPLEXIA AND epilepsy; |
| ARSA | epilepsy; | METACHROMATIC LEUKODYSTROPHY |
| ARX | epilepsy; | LISSENCEPHALY, X-LPNKED, 2 |
| ASL | epilepsy; | ARGININOSUCCINIC ACIDURIA |
| ASPA | epilepsy; hypotonia | CANAVAN DISEASE |
| ASS1 | epilepsy; | CITRULLINEMIA, CLASSIC |
| ATP6V0A2 | epilepsy; hypotonia | CUTIS LAXA, AUTOSOMAL RECESSIVE, TYPE II |
| ATP7A | epilepsy; | MENKES DISEASE |
| ATR | epilepsy; | SECKEL SYNDROME 1 |
| ATRX | epilepsy; hypotonia | THALASSEMIA/MENTAL RETARDATION SYNDROME, NONDELETION TYPE, X-LINKED |
| B4GALT1 | hypotonia | CONGENITAL DISORDER OF GLYCOSYLATION TYPE IId |
| BCKDHA | epilepsy; hypotonia | MAPLE SYRUP URINE DISEASE Type Ia |
| BCKDHB | epilepsy; hypotonia | BRANCHED-CHAIN KETO ACID DEHYDROGENASE E1, BETA POLYPEPTIDE |
| BCS1L | hypotonia | MITOCHONDRIAL COMPLEX III DEFICIENCY |
| BRWD3 | hypotonia | MENTAL RETARDATION, X-LINKED 93 |
| BTD | epilepsy; hypotonia | BIOTINIDASE DEFICIENCY |
| C10ORF2 | epilepsy; hypotonia | INFANTILE-ONSET SPINOCEREBELLAR ATAXIA |
| CBS | epilepsy; | HOMOCYSTINURIA |
| CEP290 | hypotonia | JOUBERT SYNDROME 5 |
| CLN3 | epilepsy; | NEURONAL CEROID LIPOFUSCINOSIS 3 |
| CLN5 | epilepsy; | NEURONAL CEROID LIPOFUSCINOSIS 5 |
| CLN6 | dev. motor disorder; epilepsy; | CEROID LIPOFUSCINOSIS, NEURONAL, 6 |
| CLN8 | epilepsy; | CEROID LIPOFUSCINOSIS, NEURONAL, 8 |
| COG1 | hypotonia | CONGENITAL DISORDER OF GLYCOSYLATION TYPE Iig |
| COG7 | epilepsy; hypotonia | CONGENITAL DISORDER OF GLYCOSYLATION, TYPE Iie |
| COG8 | hypotonia | CONGENITAL DISORDER OF GLYCOSYLATION TYPE Iih |
| COQ2 | epilepsy; | COENZYME Q10 DEFICIENCY |
| COQ9 | epilepsy; | COENZYME Q10 DEFICIENCY |
| COX10 | hypotonia | Complex IV deficiency |
| COX15 | hypotonia | Complex IV deficiency |
| COX6B1 | hypotonia | Complex IV deficiency |
| CPS1 | epilepsy; | CARBAMOYL PHOSPHATE SYNTHETASE I DEFICIENCY, HYPERAMMONEMIA DUE TO |
| CPT1A | hypotonia | CARNITINE PALMITOYLTRANSFERASE I DEFICIENCY |
| CPT2 | dev. motor disorder; epilepsy; | CARNITINE PALMITOYLTRANSFERASE II DEFICIENCY |
| CRLF1 | epilepsy; | CRISPONI SYNDROME |
| CSTB | epilepsy; | MYOCLONIC epilepsy; OF UNVERRICHT AND LUNDBORG |
| CTSD | epilepsy; | CEROID LIPOFUSCINOSIS, NEURONAL, 10 |
| CYP27B1 | dev. motor disorder; hypotonia | VITAMIN D-DEPENDENT osteopenia, TYPE I |
| DBT | epilepsy; hypotonia | MSUD type 2 |
| DCX | epilepsy; hypotonia | LISSENCEPHALY, X-LINKED, 1 |
| DGUOK | epilepsy; hypotonia | MITOCHONDRIAL DNA DEPLETION SYNDROME, HEPATOCEREBRAL FORM |
| DLD | epilepsy; hypotonia | DIHYDROLIPOAMIDE DEHYDROGENASE DEFICIENCY |
| DMD | dev. motor disorder; | MUSCULAR DYSTROPHY, DUCHENNE TYPE |
| DOLK | epilepsy; hypotonia | CONGENITAL DISORDER OF GLYCOSYLATION TYPE Im |
| DPAGT1 | epilepsy; hypotonia | CONGENITAL DISORDER OF GLYCOSYLATION, TYPE Ij |
| DPM1 | epilepsy; hypotonia | CONGENITAL DISORDER OF GLYCOSYLATION, TYPE Ie |
| DPYD | epilepsy; hypotonia | DIHYDROPYRIMIDINE DEHYDROGENASE |
| EGR2 | dev. motor disorder; hypotonia | HYPERTROPHIC NEUROPATHY OF DEJERINE-SOTTAS |
| EPM2A | epilepsy; | MYOCLONIC epilepsy; OF LAFORA |
| ERBB3 | dev. motor disorder; | LETHAL CONGENITAL CONTRACTURE SYNDROME 2 |
| ERCC6 | dev. motor disorder; hypotonia | COCKAYNE SYNDROME TYPE B CEREBROOCULOFACIOSKELETAL SYNDROME 1 |
| ETFA | hypotonia | MULTIPLE ACYL-CoA DEHYDROGENASE DEFICIENCY |
| ETFB | hypotonia | MULTIPLE ACYL-CoA DEHYDROGENASE DEFICIENCY |
| ETFDH | hypotonia | MULTIPLE ACYL-CoA DEHYDROGENASE DEFICIENCY |
| ETHE1 | epilepsy; hypotonia | ENCEPHALOPATHY, ETHYLMALONIC |
| FAH | dev. motor disorder; | TYROSINEMIA, TYPE I |
| FAM126A | epilepsy; hypotonia | LEUKODYSTROPHY, HYPOMYELINATING, 5 |
| FASTKD2 | hypotonia | Complex IV deficiency |
| FGD4 | dev. motor disorder; | CHARCOT-MARIE-TOOTH DISEASE, TYPE 4H |
| FH | epilepsy; hypotonia | FUMARASE DEFICIENCY |
| FKRP | dev. motor disorder; hypotonia | MUSCULAR DYSTROPHY, CONGENITAL, 1C |
| FKTN | epilepsy; hypotonia | FUKUYAMA CONGENITAL MUSCULAR DYSTROPHY |
| FOLR1 | epilepsy; | NEURODEGENERATION DUE TO CEREBRAL FOLATE TRANSPORT DEFICIENCY |
| FTSJ1 | epilepsy; | MENTAL RETARDATION, X-LINKED 9 |

TABLE S4-continued

| Gene | Search term(s) | Disease(s) |
|---|---|---|
| GAA | dev. motor disorder; hypotonia | GLYCOGEN STORAGE DISEASE II (pompe) |
| GALC | epilepsy; | KRABBE DISEASE |
| GAMT | epilepsy; | GUANIDINOACETATE METHYLTRANSFERASE DEFICIENCY |
| GBA | epilepsy; | GAUCHER DISEASE II |
| GBE1 | dev. motor disorder; | GLYCOGEN STORAGE DISEASE IV |
| GCDH | hypotonia | GLUTARIC ACIDEMIA I |
| GCSH | epilepsy; hypotonia | GLYCINE ENCEPHALOPATHY |
| GDAP1 | dev. motor disorder; | CHARCOT-MARIE-TOOTH DISEASE TYPE 4A |
| GFM1 | dev. motor disorder; | COMBINED OXIDATIVE PHOSPHORYLATION DEFICIENCY 1 |
| GJC2 | epilepsy; | LEUKODYSTROPHY, HYPOMYELINATING, 2 |
| GLB1 | epilepsy; | GM1-GANGLIOSIDOSIS TYPE II |
| GLDC | epilepsy; hypotonia | GLYCINE ENCEPHALOPATHY |
| GLE1 | dev. motor disorder; | LETHAL CONGENITAL CONTRACTURE SYNDROME 1 |
| GNPTAB | hypotonia | MUCOLIPIDOSIS II ALPHA/BETA |
| GSS | epilepsy; | GLUTATHIONE SYNTHETASE DEFICIENCY |
| HADH | epilepsy; hypotonia | 3-HYDROXYACYL-CoA DEHYDROGENASE DEFICIENCY |
| HADHA | epilepsy; hypotonia | HYDROXYACYL-CoA DEHYDROGENASE |
| HADHB | epilepsy; hypotonia | TRIFUNCTIONAL PROTEIN DEFICIENCY |
| HAX1 | epilepsy; | neutropenia, SEVERE CONGENITAL, AUTOSOMAL RECESSIVE 3 |
| HESX1 | epilepsy; | PITUITARY DWARFISM III |
| HEXA | epilepsy; | TAY-SACHS DISEASE |
| HLCS | epilepsy; hypotonia | HOLOCARBOXYLASE SYNTHETASE DEFICIENCY |
| HSD17B10 | hypotonia | MENTAL RETARDATION, X-LINKED, SYNDROMIC 10 |
| HSD17B4 | epilepsy; hypotonia | D-BIFUNCTIONAL PROTEIN DEFICIENCY |
| IGHMBP2 | dev. motor disorder; | SPINAL MUSCULAR ATROPHY, DISTAL, AUTOSOMAL RECESSIVE, 1 |
| IKBKAP | hypotonia | NEUROPATHY, HEREDITARY SENSORY AND AUTONOMIC, TYPE III |
| IL1RAPL1 | hypotonia | MENTAL RETARDATION, X-LINKED 21 |
| IVD | epilepsy; | ISOVALERIC ACIDEMIA |
| KDM5C | epilepsy; | MENTAL RETARDATION, X-LINKED, SYNDROMIC |
| L1CAM | epilepsy; hypotonia | HYDROCEPHALUS DUE TO CONGENITAL STENOSIS OF AQUEDUCT OF SYLVIUS |
| LAMA2 | dev. motor disorder; hypotonia | MUSCULAR DYSTROPHY, CONGENITAL MEROSIN-DEFICIENT, 1A |
| LAMB2 | hypotonia | PIERSON SYNDROME |
| LARGE | dev. motor disorder; hypotonia | MUSCULAR DYSTROPHY, CONGENITAL, TYPE 1D |
| LHX3 | epilepsy; | PITUITARY DWARFISM III |
| LIFR | hypotonia | STUVE-WIEDEMANN SYNDROME |
| LRPPRC | hypotonia | LEIGH SYNDROME, FRENCH-CANADIAN TYPE |
| MBTPS2 | epilepsy; | ICHTHYOSIS FOLLICULARIS, ATRICHIA, AND PHOTOPHOBIA SYNDROME |
| MCOLN1 | hypotonia | MUCOLIPIDOSIS IV |
| MECP2 | epilepsy; hypotonia | RETT SYNDROME |
| MED12 | epilepsy; hypotonia | LUJAN-FRYNS SYNDROME |
| MFSD8 | epilepsy; | CEROID LIPOFUSCINOSIS, NEURONAL, 7 |
| MGAT2 | epilepsy; hypotonia | CONGENITAL DISORDER OF GLYCOSYLATIO, TYPE IIa |
| MLC1 | epilepsy; | MEGALENCEPHALIC LEUKOENCEPHALOPATHY WITH SUBCORTICAL CYSTS |
| MMAA | hypotonia | METHYLMALONIC ACIDURIA, cblA TYPE |
| MMAB | hypotonia | METHYLMALONIC ACIDURIA, cblB TYPE |
| MMACHC | hypotonia | METHYLMALONIC ACIDURIA AND HOMOCYSTINURIA, cblC TYPE |
| MOCS1 | epilepsy; | MOLYBDENUM COFACTOR DEFICIENCY |
| MOCS2 | epilepsy; | MOLYBDENUM COFACTOR DEFICIENCY |
| MOGS | epilepsy; hypotonia | CONGENITAL DISORDER OF GLYCOSYLATION TYPE IIb |
| MPDU1 | epilepsy; hypotonia | CONGENITAL DISORDER OF GLYCOSYLATION, TYPE If |
| MPI | epilepsy; hypotonia | CONGENITAL DISORDER OF GLYCOSYLATION, TYPE Ib |
| MPV17 | epilepsy; hypotonia | MITOCHONDRIAL DNA DEPLETION SYNDROME, HEPATOCEREBRAL FORM |
| MPZ | dev. motor disorder; hypotonia | HYPERTROPHIC NEUROPATHY OF DEJERINE-SOTTAS |
| MRPS16 | hypotonia | COMBINED OXIDATIVE PHOSPHORYLATION DEFICIENCY 2 |
| MRPS22 | hypotonia | COMBINED OXIDATIVE PHOSPHORYLATION DEFICIENCY 5 |
| MTM1 | dev. motor disorder; | MYOTUBULAR MYOPATHY 1 |
| MUT | hypotonia | METHYLMALONIC ACIDURIA DUE TO METHYLMALONYL-CoA MUTASE DEFICIENCY |
| MYO5A | epilepsy; hypotonia | GRISCELLI SYNDROME, TYPE 1 |
| MYO7A | dev. motor disorder; | USHER SYNDROME, TYPE I |
| NAGS | epilepsy; | N-ACETYLGLUTAMATE SYNTHASE DEFICIENCY |
| NDP | epilepsy; | NORRIE DISEASE |
| NDUFA1 | epilepsy; | Complex I Deficiency |
| NDUFA7 | epilepsy; | Complex I Deficiency |
| NDUFAF2 | epilepsy; | Complex I Deficiency |
| NDUFAF4 | epilepsy; | Complex I Deficiency |

TABLE S4-continued

| Gene | Search term(s) | Disease(s) |
|---|---|---|
| NDUFS3 | epilepsy; | Complex I Deficiency |
| NDUFS4 | epilepsy; | Complex I Deficiency |
| NDUFS5 | epilepsy; | Complex I Deficiency |
| NDUFS6 | epilepsy; | Complex I Deficiency |
| NDUFS7 | epilepsy; | Complex I Deficiency |
| NDUFS8 | epilepsy; | Complex I Deficiency |
| NDUFV1 | epilepsy; | Complex I Deficiency |
| NEB | dev. motor disorder; hypotonia | NEMALINE MYOPATHY 2 |
| NEU1 | epilepsy; | NEURAMINIDASE DEFICIENCY |
| NHLRC1 | epilepsy; | MYOCLONIC epilepsy; OF LAFORA |
| NPC1 | epilepsy; | NIEMANN-PICK DISEASE, TYPE C1 |
| NPC2 | epilepsy; hypotonia | NIEMANN-PICK DISEASE, TYPE C2 |
| NPHP1 | hypotonia | JOUBERT SYNDROME 4 |
| NR0B1 | epilepsy; | CONGENITAL ADRENAL HYPOPLASIA |
| OCRL | epilepsy; hypotonia | LOWE OCULOCEREBRORENAL SYNDROME |
| OFD1 | hypotonia | SIMPSON-GOLABI-BEHMEL SYNDROME, TYPE 2 |
| OPHN1 | epilepsy; hypotonia | ID XLR, W CEREBELLAR HYPOPLASIA & DISTINCTIVE FACIAL APPEARANCE |
| ORAI1 | dev. motor disorder; hypotonia | IMMUNE DYSFUNCTION WITH T-CELL INACTIVATION DUE TO CALCIUM ENTRY DEFECT 1 |
| OTC | epilepsy; | ORNITHINE TRANSCARBAMYLASE DEFICIENCY, HYPERAMMONEMIA DUE TO |
| PAH | epilepsy; | PHENYLKETONURIA |
| PAK3 | epilepsy; | MENTAL RETARDATION, X-LINKED 30 |
| PC | epilepsy; hypotonia | PYRUVATE CARBOXYLASE DEFICIENCY |
| PCCA | epilepsy; hypotonia | PROPIONIC ACIDEMIA |
| PCCB | epilepsy; hypotonia | PROPIONIC ACIDEMIA |
| PCDH19 | epilepsy; | epilepsy;, FEMALE-RESTRICTED, WITH MENTAL RETARDATION |
| PDHA1 | epilepsy; hypotonia | LEIGH SYNDROME, X-LINKED |
| PDHX | epilepsy; hypotonia | PYRUVATE DEHYDROGENASE E3-BINDING PROTEIN DEFICIENCY |
| PDP1 | epilepsy; hypotonia | PYRUVATE DEHYDROGENASE PHOSPHATASE DEFICIENCY |
| PDSS1 | epilepsy; | COENZYME Q10 DEFICIENCY |
| PDSS2 | epilepsy; | COENZYME Q10 DEFICIENCY |
| PEX1 | epilepsy; hypotonia | ZELLWEGER SYNDROME |
| PEX10 | epilepsy; hypotonia | ADRENOLEUKODYSTROPHY, AUTOSOMAL NEONATAL FORM |
| PEX12 | epilepsy; hypotonia | ZELLWEGER SYNDROME |
| PEX13 | epilepsy; hypotonia | ADRENOLEUKODYSTROPHY, AUTOSOMAL NEONATAL FORM |
| PEX26 | epilepsy; hypotonia | ADRENOLEUKODYSTROPHY, AUTOSOMAL NEONATAL FORM |
| PEX5 | epilepsy; hypotonia | ADRENOLEUKODYSTROPHY, AUTOSOMAL NEONATAL FORM |
| PEX7 | epilepsy; | RHIZOMELIC CHONDRODYSPLASIA PUNCTATA TYPE 1 |
| PLA2G6 | epilepsy; hypotonia | INFANTILE NEUROAXONAL DYSTROPHY |
| PLEC | dev. motor disorder; | EPIDERMOLYSIS BULLOSA SIMPLEX WITH MUSCULAR DYSTROPHY |
| PLEKHG5 | dev. motor disorder; | SPINAL MUSCULAR ATROPHY, DISTAL, AUTOSOMAL RECESSIVE, 4 |
| PLOD1 | dev. motor disorder; hypotonia | NEVO SYNDROME |
| PLP1 | hypotonia | PELIZAEUS-MERZBACHER DISEASE |
| PMM2 | epilepsy; hypotonia | CONGENITAL DISORDER OF GLYCOSYLATION TYPE Ia |
| PMP22 | dev. motor disorder; hypotonia | HYPERTROPHIC NEUROPATHY OF DEJERINE-SOTTAS |
| PNPO | epilepsy; hypotonia | PYRIDOXAMINE 5-PRIME-PHOSPHATE OXIDASE DEFICIENCY |
| POLG | epilepsy; hypotonia | ALPERS DIFFUSE DEGENERATION OF CEREBRAL GRAY MATTER WITH HEPATIC CIRRHOSIS |
| POMGNT1 | hypotonia | MUSCLE-EYE-BRAIN DISEASE |
| POMT1 | hypotonia | WALKER-WARBURG SYNDROME |
| POMT2 | hypotonia | WALKER-WARBURG SYNDROME |
| POU1F1 | epilepsy; | PITUITARY DWARFISM III |
| PPT1 | epilepsy; | NEURONAL CEROID LIPOFUSCINOSIS 1 |
| PROP1 | epilepsy; | PITUITARY DWARFISM III |
| PRPS1 | hypotonia | ARTS SYNDROME |
| PRX | dev. motor disorder; hypotonia | HYPERTROPHIC NEUROPATHY OF DEJERINE-SOTTAS |
| PSAP | epilepsy; hypotonia | COMBINED SAPOSIN DEFICIENCY |
| RAB27A | epilepsy; | GRISCELLI SYNDROME, TYPE 2 |
| RAB39B | epilepsy; | MENTAL RETARDATION X-LINKED 72 |
| RAB3GAP1 | hypotonia | WARBURG MICRO SYNDROME |
| RAPSN | dev. motor disorder; | FETAL AKINESIA DEFORMATION SEQUENCE |
| RELN | epilepsy; hypotonia | LISSENCEPHALY 2 |
| RFT1 | epilepsy; hypotonia | CONGENITAL DISORDER OF GLYCOSYLATION, TYPE In |
| RNASEH2A | epilepsy; | AICARDI-GOUTIERES SYNDROME 4 |
| RNASEH2B | epilepsy; | AICARDI-GOUTIERES SYNDROME 2 |
| RNASEH2C | epilepsy; | AICARDI-GOUTIERES SYNDROME 3 |
| RPS6KA3 | epilepsy; | COFFIN-LOWRY SYNDROME |
| RRM2B | epilepsy; hypotonia | mtDNA depletion, encephalomyopathic form |
| SACS | dev. motor disorder; | SPASTIC ATAXIA, CHARLEVOIX-SAGUENAY TYPE |

TABLE S4-continued

| Gene | Search term(s) | Disease(s) |
|---|---|---|
| SC5DL | hypotonia | LATHOSTEROLOSIS |
| SCO1 | hypotonia | Complex IV deficiency |
| SCO2 | hypotonia | CARDIOENCEPHALOMYOPATHY, FATAL INFANTILE, DUE TO CYTOCHROME c OXIDASE |
| SEPN1 | dev. motor disorder; hypotonia | RIGID SPINE MUSCULAR DYSTROPHY 1 |
| SGSH | epilepsy; | MUCOPOLYSACCHARIDOSIS TYPE IIIA (Sanfilippo type A) |
| SIL1 | hypotonia | Marinesco-Sjogren Syndrome |
| SLC12A6 | dev. motor disorder; | AGENESIS OF THE CORPUS CALLOSUM WITH PERIPHERAL NEUROPATHY |
| SLC16A2 | hypotonia | ALLAN-HERNDON-DUDLEY SYNDROME |
| SLC17A5 | epilepsy; hypotonia | SIALURIA, FINNISH TYPE INFANTILE SIALIC ACID STORAGE DISORDER |
| SLC22A5 | hypotonia | CARNITINE DEFICIENCY, SYSTEMIC PRIMARY |
| SLC25A15 | epilepsy; hypotonia | HYPERORNITHINEMIA-HYPERAMMONEMIA-HOMOCITRULLINURIA SYNDROME |
| SLC25A20 | epilepsy; | CARNITINE-ACYLCARNITINE TRANSLOCASE DEFICIENCY |
| SLC25A22 | epilepsy; hypotonia | EPILEPTIC ENCEPHALOPATHY, EARLY INFANTILE, 3 |
| SLC35C1 | epilepsy; hypotonia | CONGENITAL DISORDER OF GLYCOSYLATION TYPE IIc |
| SLC6A8 | epilepsy; | CREATINE DEFICIENCY SYNDROME, X-LINKED |
| SLC9A6 | epilepsy; | MENTAL RETARDATION, X-LINKED ANGELMAN, SYNDROMIC, CHRISTIANSON |
| SMN1 | dev. motor disorder; hypotonia | SPINAL MUSCULAR ATROPHY TYPE I |
| SMPD1 | hypotonia | NIEMANN-PICK DISEASE, TYPE A |
| SMS | epilepsy; hypotonia | MENTAL RETARDATION, X-LINKED, SNYDER-ROBINSON TYPE |
| SNAP29 | hypotonia | CEREBRAL DYSGENESIS, NEUROPATHY, ICHTHYOSIS, PALMOPLANTAR KERATODERMA |
| ST3GAL5 | epilepsy; hypotonia | AMISH INFANTILE epilepsy; SYNDROME |
| STIM1 | dev. motor disorder; hypotonia | IMMUNE DYSFUNCTION WITH T-CELL INACTIVATION DUE TO CALCIUM ENTRY DEFECT 2 |
| STRA6 | hypotonia | MICROPHTHALMIA, SYNDROMIC 9 (Matthew-Wood syndrome) |
| SUCLA2 | dev. motor disorder; hypotonia | mtDNA depletion, encephalomyopathic form |
| SUCLG1 | epilepsy; hypotonia | LACTIC ACIDOSIS, FATAL INFANTILE (mtDNA depletion) |
| SUOX | epilepsy; hypotonia | SULFOCYSTEINURIA |
| SURF1 | epilepsy; hypotonia | LEIGH SYNDROME |
| SYP | epilepsy; | MENTAL RETARDATION X-LINKED SYP-RELATED |
| TBCE | epilepsy; | HYPOPARATHYROIDISM-RETARDATION-DYSMORPHISM SYNDROME |
| TCIRG1 | epilepsy; | OSTEOPETROSIS, AUTOSOMAL RECESSIVE 1 |
| TH | dev. motor disorder; hypotonia | SEGAWA SYNDROME, AUTOSOMAL RECESSIVE |
| TK2 | dev. motor disorder; hypotonia | MITOCHONDRIAL DNA DEPLETION SYNDROME, MYOPATHIC FORM |
| TMEM67 | hypotonia | JOUBERT SYNDROME 6 |
| TNFRSF11B | dev. motor disorder; | PAGET DISEASE, JUVENILE |
| TPP1 | epilepsy; | NEURONAL CEROID LIPOFUSCINOSIS 2 |
| TRAPPC9 | epilepsy; | MENTAL RETARDATION AUTOSOMAL RECESSIVE 13 |
| TREX1 | epilepsy; | AICARDI-GOUTIERES SYNDROME 1 |
| TRIM37 | hypotonia | MULIBREY NANISM |
| TSEN54 | epilepsy; | PONTOCEREBELLAR HYPOPLASIA TYPE 2A |
| TSFM | epilepsy; hypotonia | COMBINED OXIDATIVE PHOSPHORYLATION DEFICIENCY 3 |
| TSHB | hypotonia | HYPOTHYROIDISM, CONGENITAL, NONGOITROUS, 4 |
| TUBA1a | epilepsy; | LISSENCEPHALY 3 |
| TUFM | hypotonia | COMBINED OXIDATIVE PHOSPHORYLATION DEFICIENCY 4 |
| UBA1 | dev. motor disorder; hypotonia | SPINAL MUSCULAR ATROPHY, X-LINKED 2 |
| UQCRB | hypotonia | MITOCHONDRIAL COMPLEX III DEFICIENCY |
| UQCRQ | hypotonia | MITOCHONDRIAL COMPLEX III DEFICIENCY |
| VDR | epilepsy; hypotonia | VITAMIN D-DEPENDENT osteopenia, TYPE II |
| VLDLR | hypotonia | CEREBELLAR HYPOPLASIA AND ID WITH/WITHOUT QUADRUPEDAL |
| VPS13B | epilepsy; hypotonia | COHEN SYNDROME |
| VPS33B | hypotonia | ARTHROGRYPOSIS, RENAL DYSFUNCTION, AND CHOLESTASIS |
| ZNF41 | epilepsy; | MENTAL RETARDATION X-LINKED 89 |

There were no previously reported disease-causing variants in these 276 genes. However, five of the candidate genes contained either variants of a type that are expected to be disease-causing based on their predicted functional consequence, or missense variants of unknown significance (VUS). One of these variants was in a gene that matched all three clinical terms and was a hemizygous substitution mutation in the gene that encodes the α polypeptide of copper-transporting ATPase (ATP7A Chr X:77,271,307C>T, c.2555C>T, p.P852L), aberrant forms of which are known to cause Menkes disease, a copper-transport disorder. This variant—new to our database and dbSNP—specified a non-conservative substitution in an amino acid that was highly conserved across species and had deleterious SIFT (Sorts Intolerant From Tolerant substitutions), PolyPhen2 (Polymorphism Phenotyping), and BLOSUM (BLOcks SUbstitution Matrix) scores. The known diagnosis of Menkes disease (OMIM#309400) was recapitulated.

The following prospective analyses were preformed and results provided. Mutations in 34 genes can cause generalized, erosive dermatitis of the type found in CMH064 as shown in Table S5 below.

TABLE S5

| Erosive dermatitis candidate genes |
| --- |
| AHNAK |
| ALOX12B |
| CD151 |
| CDSN |
| CHST8 |
| COL17A1 |
| COL7A1 |
| CTNNB1 |
| CTNND1 |
| CSTA |
| DSG1 |
| DSC1 |
| DSP |
| DST |
| GRIP1 |

TABLE S5-continued

| Erosive dermatitis candidate genes |
| --- |
| KRT14 |
| KRT16 |
| KRT2 |
| KRT5 |
| KRT9 |
| LAMA3 |
| LAMB3 |
| LAMC1 |
| LAMC2 |
| PKP1 |
| PLEC1 |
| TGM5 |
| TP63 |

The severe phenotype, negative family history and absence of consanguinity suggested dominant de novo or recessive inheritance. No known pathogenic mutations were identified in the candidate genes that had low allele frequencies in the cumulative genome and exome sequence database and similar public databases. Average coverage of the genomic regions corresponding to the candidate genes was 38.9-fold, and 98.4% of candidate gene nucleotides had >16× high-quality coverage (sufficient to rule out a heterozygous variant; as shown in Table S6 below).

TABLE S6

| Target (Chr:nt start-nt stop) | Gene | Mean Coverage | % Nt With Coverage >15X | Pseudogene | Paralog | Repeat segments |
| --- | --- | --- | --- | --- | --- | --- |
| 11:62201016-62314332 | AHNAK | 37.0 | 99.8 | no | yes | yes |
| 17:7975954-7991021 | ALOX12B | 35.0 | 99.7 | yes | yes | |
| 6:31082865-31088252 | CDSN | 37.7 | 99.8 | no | no | no |
| 19:34112861-34264414 | CHST8 | 37.7 | 99.3 | no | yes | |
| 10:105791046-105845638 | COL17A1 | 38.5 | 99.8 | no | no | yes |
| 3:48601506-48632593 | COL7A1 | 34.3 | 100 | no | no | yes |
| 3:122044011-122060815 | CSTA | 40.4 | 99.9 | no | yes | no |
| 3:41240942-41281939 | CTNNB1 | 42.2 | 100 | no | yes | yes |
| 11:57529234-57586652 | CTNND1 | 40.7 | 99.7 | no | no | yes |
| 18:28709214-28742819 | DSC1 | 44.2 | 99.6 | no | yes | |
| 18:28898052-28937393 | DSG1 | 39.5 | 90.2 | no | yes | |
| 6:7541870-7586946 | DSP | 41.0 | 99.9 | no | yes | |
| 6:56322785-56507694 | DST | 43.9 | 99.2 | no | no | |
| 12:66741211-67072925 | GRIP1 | 41.3 | 98.2 | no | no | |
| 2:173292314-173371181 | ITGA6 | 41.1 | 99.5 | no | yes | |
| 17:73717516-73753899 | ITGB4 | 35.5 | 100 | no | yes | |
| 17:39910859-39942964 | JUP | 36.1 | 99.8 | no | no | |
| 12:53068520-53074191 | KRT1 | 38.5 | 98.7 | no | yes | |
| 17:38974369-38978863 | KRT10 | 40.9 | 99.8 | no | yes | |
| 17:39738531-39743147 | KRT14 | 35.4 | 99.6 | yes | yes | |
| 17:39766031-39769079 | KRT16 | 33.1 | 96.1 | yes | yes | |
| 12:53038342-53045959 | KRT2 | 39.0 | 100 | no | yes | |
| 12:52908359-52914243 | KRT5 | 38.1 | 100 | no | yes | |
| 17:39722094-39728310 | KRT9 | 36.3 | 100 | no | yes | |
| 18:21269562-21535029 | LAMA3 | 41.1 | 99.7 | no | yes | |
| 1:209788218-209825820 | LAMB3 | 38.2 | 99.9 | no | yes | |
| 1:182992595-183114727 | LAMC1 | 41.6 | 100 | no | no | |
| 1:183155174-183214262 | LAMC2 | 40.8 | 100 | no | yes | |
| 1:201252580-201302121 | PKP1 | 38.4 | 99.9 | no | yes | |
| 8:144989321-145050913 | PLEC | 35.1 | 99.2 | no | no | |
| 15:43524793-43559055 | TGM5 | 39.2 | 99.8 | no | yes | |
| 3:189349216-189615068 | TP63 | 43.6 | 99.8 | no | yes | |
| Average | | 38.9 | 99.3 | 3 | 23 | |

TABLE S5-continued

| Erosive dermatitis candidate genes |
| --- |
| ITGA3 |
| ITGA6 |
| ITGB4 |
| JUP |
| KRT1 |
| KRT10 |

Five candidate genes had 100% nucleotides with >16-fold high-quality coverage, and, thus, clearly lacked a known pathogenic mutation in an exon or within 20 nucleotides of the intron-exon boundaries. Eighteen of the candidate genes had >99% nucleotides with >16-fold high-quality coverage, and 31 had >95% nucleotides with at least this level of coverage. Furthermore, while 26 of the candidate genes had pseudogenes, paralogs, and/or repeat segments as shown in Table S6 above that could potentially result in mis-alignment and variant mis-calls, only 0.03% of target nucleotides had poor alignment quality scores.

Among the 34 candidate genes, one rare heterozygous VUS was detected in CMH064; however, dideoxy sequencing of both healthy parents excluded it as a de novo mutation. The exomes of both parents were subsequently sequenced, and variants were examined in the trio. No VUS in a gene related to the 34 known epidermolysis bullosa genes had a pattern of inheritance in the trio that was consistent with causality.

Diagnoses suggested by the presentation in CMH076 were mitochondrial disorders, organic acidemia, or pyruvate carboxylase deficiency. Together, 75 nuclear genes and the mitochondrial genome cause these diseases as shown in Table S7 below.

TABLE S7

Nuclear Genes Causing Mitochondrial Disease

AGK
AIF1
ATPAF2
BCS1L
C8orf38
C10orf2
C20orf7
CABC1
COQ2
COQ9
COX10
COX15
DGUOK
DLD
DTNA
ETFDH
FKBP12
FOXRED1
GFER
LDB3
LRPPRC
MPV17
NDUFA1
NDUFA2
NDUFA10
NDUFA11
NDUFA9
NDUFAF1
NDUFAF2
NDUFAF3
NDUFAF4
NDUFS1
NDUFS2
NDUFS3
NDUFS4
NDUFS6
NDUFS7
NDUFS8
NDUFV1
NDUFV2

TABLE S7-continued

Nuclear Genes Causing Mitochondrial Disease

NUBPL
OPA1
OPA3
PEX
PEX10
PEX12
PEX13
PEX14
PEX16
PEX19
PEX2
PEX26
PEX3
PEX5
PEX6
POLG
POLG2
RRM2B
SACS
SCO1
SCO2
SDHA
SDHAF1
SLC25A3
SLC25A4
SUCLA2
SUCLG1
SUCLG2
SURF1
TAZ
TK2
TMEM70
TRMU
TYMP
UQCRB

A negative family history suggested recessive inheritance that resulted from compound heterozygous or hemizygous variants or a heterozygous de novo dominant variant. Rapid WGS excluded known pathogenic mutations in the candidate genes. One novel heterozygous VUS was found. However, de novo occurrence of this variant was ruled out by exome sequencing of his healthy parents. No homozygous or compound heterozygous VUS with suitably low allele frequencies were identified in the known disease genes. Potential novel candidates included 929 nuclear genes that encode mitochondrial proteins but have not yet been associated with a genetic disease. Only one of these had a homozygous or compound heterozygous VUS with an allele frequency in dbSNP and the database that was sufficiently low to be a candidate for causality in an uncommon inherited disease. Deep exome sequencing of both parents excluded this variant and did not disclose any further potentially causal variants.

A total of 174 genes are known to cause epilepsy of the type found in CMH172, as shown below in Table S8.

TABLE S8

| Gene | Search term(s) | Disease(s) |
| --- | --- | --- |
| ABCC8 | epilepsy | HYPERINSULINEMIC HYPOGLYCEMIA, FAMILIAL, 1 |
| ACOX1 | epilepsy | PEROXISOMAL ACYL-CoA OXIDASE DEFICIENCY |
| ADAMTSL2 | epilepsy | GELEOPHYSIC DYSPLASIA |
| ADCK3 | epilepsy | COENZYME Q10 DEFICIENCY |
| AGTR2 | epilepsy | MENTAL RETARDATION X-LINKED 88 |
| ALDH3A2 | epilepsy | SJOGREN-LARSSON SYNDROME |
| ALDH5A1 | epilepsy | SUCCINIC SEMIALDEHYDE DEHYDROGENASE DEFICIENCY |
| ALDH7A1 | epilepsy | EPILEPSY, PYRIDOXINE-DEPENDENT; EPD |
| ALDOB | epilepsy | FRUCTOSE INTOLERANCE, HEREDITARY |
| ALG12 | epilepsy | CONGENITAL DISORDER OF GLYCOSYLATION TYPE Ig |
| ALG2 | epilepsy | CONGENITAL DISORDER OF GLYCOSYLATION TYPE Ii |

TABLE S8-continued

| Gene | Search term(s) | Disease(s) |
|---|---|---|
| ALG3 | epilepsy | CONGENITAL DISORDER OF GLYCOSYLATION, TYPE Id; CDG1D |
| ALG6 | epilepsy | CONGENITAL DISORDER OF GLYCOSYLATION TYPE Ic |
| ALG8 | epilepsy | CONGENITAL DISORDER OF GLYCOSYLATION, TYPE Ih |
| ALG9 | epilepsy | CONGENITAL DISORDER OF GLYCOSYLATION, TYPE Il |
| ALPL | epilepsy | HYPOPHOSPHATASIA, CHILDHOOD |
| AMT | epilepsy | GLYCINE ENCEPHALOPATHY |
| APTX | epilepsy | COENZYME Q10 DEFICIENCY |
| ARHGEF9 | epilepsy | HYPEREKPLEXIA AND EPILEPSY |
| ARSA | epilepsy | METACHROMATIC LEUKODYSTROPHY |
| ARX | epilepsy | LISSENCEPHALY, X-LINKED, 2 |
| ASL | epilepsy | ARGININOSUCCINIC ACIDURIA |
| ASPA | epilepsy | CANAVAN DISEASE |
| ASS1 | epilepsy | CITRULLINEMIA, CLASSIC |
| ATP6V0A2 | epilepsy | CUTIS LAXA, AUTOSOMAL RECESSIVE, TYPE II |
| ATP7A | epilepsy | MENKES DISEASE |
| ATR | epilepsy | SECKEL SYNDROME 1 |
| ATRX | epilepsy | ?-THALASSEMIA/MENTAL RETARDATION SYNDROME, NONDELETION TYPE, X-LINKED |
| BCKDHA | epilepsy | MAPLE SYRUP URINE DISEASE Type Ia |
| BCKDHB | epilepsy | BRANCHED-CHAIN KETO ACID DEHYDROGENASE E1, BETA POLYPEPTIDE |
| BTD | epilepsy | BIOTINIDASE DEFICIENCY |
| C10ORF2 | epilepsy | INFANTILE-ONSET SPINOCEREBELLAR ATAXIA |
| CBS | epilepsy | HOMOCYSTINURIA |
| CLN3 | epilepsy | NEURONAL CEROID LIPOFUSCINOSIS 3 |
| CLN5 | epilepsy | NEURONAL CEROID LIPOFUSCINOSIS 5 |
| CLN6 | epilepsy | CEROID LIPOFUSCINOSIS, NEURONAL, 6 |
| CLN8 | epilepsy | CEROID LIPOFUSCINOSIS, NEURONAL, 8 |
| COG7 | epilepsy | CONGENITAL DISORDER OF GLYCOSYLATION, TYPE IIe |
| COQ2 | epilepsy | COENZYME Q10 DEFICIENCY |
| COQ9 | epilepsy | COENZYME Q10 DEFICIENCY |
| CPS1 | epilepsy | CARBAMOYL PHOSPHATE SYNTHETASE I DEFICIENCY, HYPERAMMONEMIA DUE TO |
| CPT2 | epilepsy | CARNITINE PALMITOYLTRANSFERASE II DEFICIENCY, INFANTILE |
| CRLF1 | epilepsy | CRISPONI SYNDROME |
| CSTB | epilepsy | MYOCLONIC EPILEPSY OF UNVERRICHT AND LUNDBORG |
| CTSD | epilepsy | CEROID LIPOFUSCINOSIS, NEURONAL, 10 |
| DBT | epilepsy | MSUD type 2 |
| DCX | epilepsy | LISSENCEPHALY, X-LINKED, 1 |
| DGUOK | epilepsy | MITOCHONDRIAL DNA DEPLETION SYNDROME, HEPATOCEREBRAL FORM |
| DLD | epilepsy | DIHYDROLIPOAMIDE DEHYDROGENASE DEFICIENCY |
| DOLK | epilepsy | CONGENITAL DISORDER OF GLYCOSYLATION TYPE Im |
| DPAGT1 | epilepsy | CONGENITAL DISORDER OF GLYCOSYLATION, TYPE Ij |
| DPM1 | epilepsy | CONGENITAL DISORDER OF GLYCOSYLATION, TYPE Ie |
| DPYD | epilepsy | DIHYDROPYRIMIDINE DEHYDROGENASE |
| EPM2A | epilepsy | MYOCLONIC EPILEPSY OF LAFORA |
| ETHE1 | epilepsy | ENCEPHALOPATHY, ETHYLMALONIC |
| FAM126A | epilepsy | LEUKODYSTROPHY, HYPOMYELINATING, 5 |
| FH | epilepsy | FUMARASE DEFICIENCY |
| FKTN | epilepsy | FUKUYAMA CONGENITAL MUSCULAR DYSTROPHY |
| FOLR1 | epilepsy | NEURODEGENERATION DUE TO CEREBRAL FOLATE TRANSPORT DEFICIENCY |
| FTSJ1 | epilepsy | MENTAL RETARDATION, X-LINKED 9 |
| GALC | epilepsy | KRABBE DISEASE |
| GAMT | epilepsy | GUANIDINOACETATE METHYLTRANSFERASE DEFICIENCY |
| GBA | epilepsy | GAUCHER DISEASE II |
| GCSH | epilepsy | GLYCINE ENCEPHALOPATHY |
| GJC2 | epilepsy | LEUKODYSTROPHY, HYPOMYELINATING, 2 |
| GLB1 | epilepsy | GM1-GANGLIOSIDOSIS TYPE II |
| GLDC | epilepsy | GLYCINE ENCEPHALOPATHY |
| GSS | epilepsy | GLUTATHIONE SYNTHETASE DEFICIENCY |
| HADH | epilepsy | 3-HYDROXYACYL-CoA DEHYDROGENASE DEFICIENCY |
| HADHA | epilepsy | HYDROXYACYL-CoA DEHYDROGENASE/3-KETOACYL-CoA THIOLASE/ENOYL-CoA HYDRATASE, |
| HADHB | epilepsy | TRIFUNCTIONAL PROTEIN DEFICIENCY |
| HAX1 | epilepsy | neutropenia, SEVERE CONGENITAL, AUTOSOMAL RECESSIVE 3 |
| HESX1 | epilepsy | PITUITARY DWARFISM III |
| HEXA | epilepsy | TAY-SACHS DISEASE |
| HLCS | epilepsy | HOLOCARBOXYLASE SYNTHETASE DEFICIENCY |
| HSD17B4 | epilepsy | D-BIFUNCTIONAL PROTEIN DEFICIENCY |
| IVD | epilepsy | ISOVALERIC ACIDEMIA |
| KDM5C | epilepsy | MENTAL RETARDATION, X-LINKED, SYNDROMIC |
| L1CAM | epilepsy | HYDROCEPHALUS DUE TO CONGENITAL STENOSIS OF AQUEDUCT OF SYLVIUS |
| LHX3 | epilepsy | PITUITARY DWARFISM III |
| MBTPS2 | epilepsy | ICHTHYOSIS FOLLICULARIS, ATRICHIA, AND PHOTOPHOBIA SYNDROME |

TABLE S8-continued

| Gene | Search term(s) | Disease(s) |
|---|---|---|
| MECP2 | epilepsy | RETT SYNDROME |
| MED12 | epilepsy | LUJAN-FRYNS SYNDROME |
| MFSD8 | epilepsy | CEROID LIPOFUSCINOSIS, NEURONAL, 7 |
| MGAT2 | epilepsy | CONGENITAL DISORDER OF GLYCOSYLATIO, TYPE IIa |
| MLC1 | epilepsy | MEGALENCEPHALIC LEUKOENCEPHALOPATHY WITH SUBCORTICAL CYSTS |
| MOCS1 | epilepsy | MOLYBDENUM COFACTOR DEFICIENCY |
| MOCS2 | epilepsy | MOLYBDENUM COFACTOR DEFICIENCY |
| MOGS | epilepsy | CONGENITAL DISORDER OF GLYCOSYLATION TYPE IIb |
| MPDU1 | epilepsy | CONGENITAL DISORDER OF GLYCOSYLATION, TYPE If |
| MPI | epilepsy | CONGENITAL DISORDER OF GLYCOSYLATION, TYPE Ib |
| MPV17 | epilepsy | MITOCHONDRIAL DNA DEPLETION SYNDROME, HEPATOCEREBRAL FORM |
| MYO5A | epilepsy | GRISCELLI SYNDROME, TYPE 1 |
| NAGS | epilepsy | N-ACETYLGLUTAMATE SYNTHASE DEFICIENCY |
| NDP | epilepsy | NORRIE DISEASE |
| NDUFA1 | epilepsy | Complex I Deficiency |
| NDUFA7 | epilepsy | Complex I Deficiency |
| NDUFAF2 | epilepsy | Complex I Deficiency |
| NDUFAF4 | epilepsy | Complex I Deficiency |
| NDUFS3 | epilepsy | Complex I Deficiency |
| NDUFS4 | epilepsy | Complex I Deficiency |
| NDUFS5 | epilepsy | Complex I Deficiency |
| NDUFS6 | epilepsy | Complex I Deficiency |
| NDUFS7 | epilepsy | Complex I Deficiency |
| NDUFS8 | epilepsy | Complex I Deficiency |
| NDUFV1 | epilepsy | Complex I Deficiency |
| NEU1 | epilepsy | NEURAMINIDASE DEFICIENCY |
| NHLRC1 | epilepsy | MYOCLONIC EPILEPSY OF LAFORA |
| NPC1 | epilepsy | NIEMANN-PICK DISEASE, TYPE C1 |
| NPC2 | epilepsy | NIEMANN-PICK DISEASE, TYPE C2 |
| NR0B1 | epilepsy | CONGENITAL ADRENAL HYPOPLASIA |
| OCRL | epilepsy | LOWE OCULOCEREBRORENAL SYNDROME |
| OPHN1 | epilepsy | MENTAL RETARDATION, XLR, W CEREBELLAR HYPOPLASIA & DISTINCTIVE FACIAL APPEARANCE |
| OTC | epilepsy | ORNITHINE TRANSCARBAMYLASE DEFICIENCY, HYPERAMMONEMIA DUE TO |
| PAH | epilepsy | PHENYLKETONURIA |
| PAK3 | epilepsy | MENTAL RETARDATION, X-LINKED 30 |
| PC | epilepsy | PYRUVATE CARBOXYLASE DEFICIENCY |
| PCCA | epilepsy | PROPIONIC ACIDEMIA |
| PCCB | epilepsy | PROPIONIC ACIDEMIA |
| PCDH19 | epilepsy | EPILEPSY, FEMALE-RESTRICTED, WITH MENTAL RETARDATION |
| PDHA1 | epilepsy | LEIGH SYNDROME, X-LINKED |
| PDHX | epilepsy | PYRUVATE DEHYDROGENASE E3-BINDING PROTEIN DEFICIENCY |
| PDP1 | epilepsy | PYRUVATE DEHYDROGENASE PHOSPHATASE DEFICIENCY |
| PDSS1 | epilepsy | COENZYME Q10 DEFICIENCY |
| PDSS2 | epilepsy | COENZYME Q10 DEFICIENCY |
| PEX1 | epilepsy | ZELLWEGER SYNDROME |
| PEX10 | epilepsy | ADRENOLEUKODYSTROPHY, AUTOSOMAL NEONATAL FORM | PEX10 |
| PEX12 | epilepsy | ZELLWEGER SYNDROME |
| PEX13 | epilepsy | ADRENOLEUKODYSTROPHY, AUTOSOMAL NEONATAL FORM | PEX13 |
| PEX26 | epilepsy | ADRENOLEUKODYSTROPHY, AUTOSOMAL NEONATAL FORM | PEX26 |
| PEX5 | epilepsy | ADRENOLEUKODYSTROPHY, AUTOSOMAL NEONATAL FORM | PEX5 |
| PEX7 | epilepsy | RHIZOMELIC CHONDRODYSPLASIA PUNCTATA TYPE 1 |
| PLA2G6 | epilepsy | INFANTILE NEUROAXONAL DYSTROPHY |
| PMM2 | epilepsy | CONGENITAL DISORDER OF GLYCOSYLATION TYPE Ia |
| PNPO | epilepsy | PYRIDOXAMINE 5-PRIME PHOSPHATE OXIDASE DEFICIENCY |
| POLG | epilepsy | ALPERS DIFFUSE DEGENERATION OF CEREBRAL GRAY MATTER WITH HEPATIC CIRRHOSIS |
| POU1F1 | epilepsy | PITUITARY DWARFISM III |
| PPT1 | epilepsy | NEURONAL CEROID LEPOFUSCINOSIS 1 |
| PROP1 | epilepsy | PITUITARY DWARFISM III |
| PSAP | epilepsy | COMBINED SAPOSIN DEFICIENCY |
| RAB27A | epilepsy | GRISCELLI SYNDROME, TYPE 2 |
| RAB39B | epilepsy | MENTAL RETARDATION X-LINKED 72 |
| RELN | epilepsy | LISSENCEPHALY 2 |
| RFT1 | epilepsy | CONGENITAL DISORDER OF GLYCOSYLATION, TYPE In |
| RNASEH2A | epilepsy | AICARDI-GOUTIERES SYNDROME 4 |
| RNASEH2B | epilepsy | AICARDI-GOUTIERES SYNDROME 2 |
| RNASEH2C | epilepsy | AICARDI-GOUTIERES SYNDROME 3 |
| RPS6KA3 | epilepsy | COFFIN-LOWRY SYNDROME |
| RRM2B | epilepsy | mtDNA depletion, encephalomyopathic form |
| SGSH | epilepsy | MUCOPOLYSACCHARIDOSIS TYPE IIIA (Sanfilippo type A) |
| SLC17A5 | epilepsy | SIALURIA, FINNISH TYPE |
| SLC25A15 | epilepsy | HYPERORNITHINEMIA-HYPERAMMONEMIA-HOMOCITRULLINURIA SYNDROME |
| SLC25A20 | epilepsy | CARNITINE-ACYLCARNITINE TRANSLOCASE DEFICIENCY |
| SLC25A22 | epilepsy | EPILEPTIC ENCEPHALOPATHY, EARLY INFANTILE, 3 |
| SLC35C1 | epilepsy | CONGENITAL DISORDER OF GLYCOSYLATION TYPE IIc |

TABLE S8-continued

| Gene | Search term(s) | Disease(s) |
|---|---|---|
| SLC6A8 | epilepsy | CREATINE DEFICIENCY SYNDROME X-LINKED |
| SLC9A6 | epilepsy | MENTAL RETARDATION, X-LINKED ANGELMAN, SYNDROMIC, CHRISTIANSON |
| SMS | epilepsy | MENTAL RETARDATION, X-LINKED, SNYDER-ROBINSON TYPE |
| ST3GAL5 | epilepsy | AMISH INFANTILE EPILEPSY SYNDROME |
| SUCLG1 | epilepsy | LACTIC ACIDOSIS, FATAL INFANTILE (mtDNA depletion) |
| SUOX | epilepsy | SULFOCYSTEINURIA |
| SURF1 | epilepsy | LEIGH SYNDROME |
| SYP | epilepsy | MENTAL RETARDATION X-LINKED SYP-RELATED |
| TBCE | epilepsy | HYPOPARATHYROIDISM-RETARDATION-DYSMORPHISM SYNDROME |
| TCIRG1 | epilepsy | OSTEOPETROSIS, AUTOSOMAL RECESSIVE 1 |
| TPP1 | epilepsy | NEURONAL CEROID LIPOFUSCINOSIS 2 |
| TRAPPC9 | epilepsy | MENTAL RETARDATION AUTOSOMAL RECESSIVE 13 |
| TREX1 | epilepsy | AICARDI-GOUTIERES SYNDROME 1 |
| TSEN54 | epilepsy | PONTOCEREBELLAR HYPOPLASIA TYPE 2A |
| TSFM | epilepsy | COMBINED OXIDATIVE PHOSPHORYLATION DEFICIENCY 3 |
| TUBA1a | epilepsy | LISSENCEPHALY 3 |
| VDR | epilepsy | VITAMIN D-DEPENDENT osteopenia, TYPE II |
| VPS13B | epilepsy | COHEN SYNDROME |
| ZNF41 | epilepsy | MENTAL RETARDATION X-LINKED 89 |

A positive family history of neonatal epilepsy and evidence of shared parental ancestry strongly suggested recessive inheritance. No known disease-causing variants or homozygous/compound heterozygous VUS with low allele frequencies were identified in these genes, which largely excluded them as causative in this patient. A genome-wide search of homozygous, likely pathogenic VUS that were novel in the database and dbSNP disclosed a frame-shifting insertion in the BRCA1-associated protein required for ATM activation-1 (BRAT1, Chr 7:2,583,573-2,583,574insATCT-TCTC,c.453_454insATCTTCTC, p.Leu152IlefsX70), A literature search yielded a very recent report of BRAT1 mutations in two infants with lethal, multifocal seizures, hypertonia, microcephaly, apnea, and bradycardia (OMIM#614498). Dideoxy sequencing confirmed the variant to be homozygous in CMH172 and heterozygous in both parents.

Rapid WGS was performed simultaneously on proband CMH184 (male), affected sibling (brother) CMH185, and their healthy parents, CMH186 and CMH202. Twelve genes have been associated with the clinical features of the brothers (heterotaxy and congenital heart disease; as shown below in Table S9).

TABLE S9

| Candidate genes for heterotaxy |
|---|
| ACVR2B |
| CCDC11 |
| CFC1 |
| CRELD1 |
| DLL1 |
| DNAH5 |
| DNAL1 |
| FOXH1 |
| LZTFL1 |
| NODAL |
| NPHP4 |
| ZIC3 |

Co-occurrence in two siblings strongly suggested recessive inheritance. No known disease causing variants or homozygous/compound heterozygous VUS with low allele frequencies were identified in these genes. A genomewide search of novel, homozygous/compound heterozygous, likely pathogenic VUS that were common to the affected brothers and heterozygous in their parents yielded two non-synonymous variants in the B-cell CLL/lymphoma 9—like gene. (BCL9L, Chr 11:118,772,350G>A, c.2102G>A, p.Gly701Asp and Chr 11:118,774,140G>A, c.554C>T, p.Ala185Val). Evidence supporting the candidacy of BCL9L for heterotaxy and congenital heart disease is presented below.

Over the last several years, the cost of WGS has fallen dramatically, potentially bringing it within the realm of cost-effectiveness for high-intensity medical practice, such as occurs in NICUs. Furthermore, experience has been gained with clinical use of WGS that has instructed initial guidelines for its use in molecular diagnosis of genetic disorders. However, a major impediment to the implementation of practical genomic medicine has been time-to-result.

This limitation has always been a problem for diagnosis of genetic diseases: Time-to-result and cost have greatly constrained the use of serial analysis of single gene targets by dideoxy sequencing. Hitherto, clinical use of WGS by next-generation sequencing has also taken at least a month: Sample preparation has taken at least a day, clustering 5 hours, 2×100 nt sequencing eleven days, alignment, variant calling, and genotyping one day, variant characterization a week, and clinical interpretation at least a week. Although exome sequencing lengthens sample preparation by several days, it decreases computation time somewhat and is less costly. For utility in acute care, the turnaround time of molecular diagnosis, including analysis, must match that of medical decision-making, which ranges from 1 to 3 days for most acute medical care. Herein we described proof-of-concept for two-day genome analysis of acutely ill neonates with suspected genetic disorders.

Automating Medicine

Much of the onerous characterization of genome variation is automated, and facilitated interpretation by restricting and prioritizing variants with respect to allele frequency, likelihood of a functional consequence, and relevance to the prompting illness. Thus, rapid WGS, as described herein, was designed for prompt disease diagnosis, rather than carrier testing or newborn screening. SSAGA mapped the clinical features in ill neonates and children to disease genes. Thereby, analysis was limited only to the parts of the genome relevant to an individual patient's presentation, in accord with guidelines for genetic testing in children. This greatly decreased the number of variants to be interpreted. In particular, SSAGA caused the vast majority of incidental (secondary) findings to be masked. In the setting of acute care in the NICU, secondary findings are anticipated to impede facile interpretation, reporting, and communication with physicians and patients greatly. SSAGA also assisted in test ordering, permitting a broad selection of genes to be nominated for testing based on entry of the patients clinical features with easy-to-use pull-down menus. The version used herein contains about 600 recessive and mitochondrial diseases and has a diagnostic sensitivity of 99.3% for those disorders. SSAGA is likely to be particularly useful in disorders that feature clinical or genetic heterogeneity or early manifestation of partial phenotypes, because it maps features to a superset of genetic disorders. Clearly, SSAGA needs to be expanded to encompass dominant disorders and to the full complement of genetic diseases that meet ACMG guidelines for testing rare disorders (such as having been reported in at least two unrelated families). Although neonatal disease presentations are often incomplete, only one feature is needed in order to match a disease gene to a presentation. In cases for which SSAGA-delimited genome analysis was negative, such as CMH064 and CMH076, a comprehensive secondary analysis was performed with limitation of variants solely to those with acceptable allele frequencies and likelihood of a functional consequence. Nevertheless, secondary analysis was relatively facile, yielding about one thousand variants per sample.

RUNES performed many laborious steps involved in variant characterization, annotation, and conversion to HGVS nomenclature in about 2 hours. RUNES unified these in an automated report that contained nearly all of the information desirable for variant interpretation, together with a cumulative variant allele frequency and a composite ACMG categorization of variant pathogenicity, shown in FIG. 4. ACMG categorization is a particularly useful standard for prioritization of the likelihood of variants being causal. In particular, more than 75% of coding variants were of ACMG category 4 (very unlikely to be pathogenic). Removal of such variants allowed rapid interpretation of high-likelihood pathogenic variants in relevant genes. The hands-on time for starting pipeline components and interpretation of known disease genes was, on average, less than one hour. Because genomic knowledge is currently limited to 1 to 2% of physicians (physician-scientists, medical geneticists, and molecular pathologists), variant characterization, interpretation, and clinical guidance tools are greatly needed, as is training of medical geneticists and genetic counselors in their use.

Return of Results

In blinded, retrospective analyses of two patients, rapid WGS correctly recapitulated known diagnoses. In child UDT002, two heterozygous, known mutations were identified in a gene that matched all clinical features. In male UDT173, a hemizygous (X-linked) variant of unknown significance was identified in the single candidate gene matching all clinical features. The variant, a non-synonymous nucleotide substitution, was predicted to be damaging. Rapid WGS also provided a definitive diagnosis in one of four infants enrolled prospectively. In CMH172, with refractory epilepsy, rapid WGS disclosed a novel, homozygous frame-shifting insertion in a single candidate gene (BRCA1-associated protein required for ATM activation-1, BRAT1). BRAT1 mutations were very recently reported in two unrelated Amish infants who suffered lethal, multifocal seizures. A molecular diagnosis was reached within one hour of WGS data inspection in CMH172, despite the fact that extant reference databases (HGMD and OMIM) had not yet been updated with a BRAT1-disease association. The diagnosis was made clinically reportable by resequencing the patient and her parents. Had this diagnosis been obtained in real-time, it can have expedited the decision to reduce or withdraw support. The latter decision was made in the absence of a molecular diagnosis after 5 weeks of ventilatory support, testing, and unsuccessful interventions to control seizures. Given high rates of NICU bed occupancy, accelerated diagnosis by rapid WGS has the potential to reduce the number of neonates who are turned away. The molecular diagnosis was also useful for genetic counseling of the infant's parents, to share the information with other family members at risk for carrying of this mutation. As suggested by recent guidelines, this case demonstrates the utility of WGS for diagnostic testing when a genetic test for a specific gene of interest is not available.

In three of five affected individuals, prospective, rapid WGS provided a definitive or likely molecular diagnosis in about 50 hours. These cases demonstrated the utility of WGS for diagnostic testing when a high degree of genetic heterogeneity exists, as suggested by recent guidelines. Confirmatory resequencing, which is necessary for return of results until rapid WGS is Clinical Laboratory Improvement Amendments (CLIA) compliant, took at least an additional 4 days. Until compliance has been established, we suggest preliminary verbal disclosure of molecular diagnoses to the neonatologist of record, followed by formal reporting upon performance of CLIA-conforming resequencing. Staged return of results of broad or complex screening tests, together with considered, expert interpretation and targeted quantification and confirmation are likely to be acceptable in intensive care. Precedents for rapid return of interim, potentially actionable results include preliminary reporting of histopathology, radiographic, and imaging studies and interim antibiotic selection based on Gram stains pending culture and sensitivity results.

Disease Gene Sleuthing

Because at least 3,700 monogenic disease genes remain to be identified, WGS will often rule out known molecular diagnoses and suggest novel candidate disease genes. Indeed, in another prospectively enrolled family, WGS resulted in the identification of a novel candidate disease gene, providing a likely molecular diagnosis. The proband was the second affected child of healthy parents. Accurate genetic counseling regarding risk of recurrence had not been possible because the first affected child lacked a molecular diagnosis. We undertook rapid WGS of the quartet simultaneously, allowing us to further limit incidental variants by requiring recessive inheritance. Rapid WGS ruled out 14 genes known to be associated with visceral heterotaxy and congenital heart disease (HTX). Among genes that had not been associated with HTX, rapid WGS of the quartet narrowed the likely pathogenic variants to two in the BCL9L gene. BCL9L had not previously been associated with a human phenotype, but is an excellent candidate gene for HTX on the basis of its role in the Wingless (Wnt) signaling pathway, which controls numerous developmental processes, including early embryonic patterning, epithelial-mesenchymal interactions, and stem cell maintenance.

Recently, the Wnt pathway was implicated in the left-right asymmetric development of vertebrate embryos, with a role in regulation of ciliated organ formation and function. The key effector of Wnt signaling is β-catenin, which functions either to promote cell adhesion by linking cadherin to the actin cytoskeleton via α-catenin or to bind transcriptional coactivators in the nucleus to activate the expression of specific genes. The protein that controls the switch between these two processes is encoded by BCL9L (also known as BCL9-2) and serves as a docking protein to link β-catenin with other transcription coactivators. BCL9L and α-catenin share competitive overlapping binding sites on β-catenin; phosphorylation of β-catenin determines which pathway is activated. The p.Gly701Asp mutation found in our patients lies within the BCL9L nuclear localization signal, which is essential for β-catenin to perform transcriptional regulatory functions in the nucleus.

BCL9L is one of two human homologs of *Drosophila* legless (lgs), a segment polarity gene required for Wnt signaling during development. lgs-deficient flies die as pharate adults with Wnt-related defects, including absent legs, and antennae and occasional wing defects. Fly embryos lacking the maternal lgs contribution display a lethal segment polarity defect. BCL9L-deficient zebrafish exhibit patterning defects of the ventro-lateral mesoderm, including severe defects of trunk and tail development. Furthermore, inhibition of zebrafish β-catenin results in defective organ laterality. Overexpression of constitutively active β-catenin in medaka fish causes cardiac laterality defects. β-catenin-deficient mice have defective development of heart, intestine, liver, pancreas, and stomach, including inverted cell types in the esophagus and posteriorization of the gut. Downregulation of Wnt signaling in mouse and zebrafish causes randomized organ laterality and randomized side-specific gene expression. These likely reflect aberrant Wnt activity on midline formation and function of Kupffer's vesicle, a ciliated organ of asymmetry in the zebrafish embryo that initiates left-right development of the brain, heart, and gut. The second human homolog of lgs, BCL9, has been implicated in complex congenital heart disease in humans, of the type found in our patients. BCL9 was originally identified in precursor-B-cell acute lymphoblastic leukemia with a t(1:14)(q21;q32) translocation, linking the Wnt pathway and certain B-cell leukemias or lymphomas. Finally, it was recently demonstrated that the Wnt/β-catenin signaling pathway regulates the ciliogenic transcription factor foxj1a expression in zebrafish. Decreased Wnt signal leads to disruption of left-right patterning, shorter/fewer cilia, loss of ciliary motility, and decreased foxj1a expression. Foxj1a is a member of the forkhead gene family and regulates transcriptional control of production of motile cilia. On the basis of this collected evidence, the symbol HTX6 has been reserved for BCL9L-associated autosomal recessive visceral heterotaxy. Additional studies are in progress to show causality definitively. These findings support clinical WGS as being valuable for research in reverse translation studies (bedside-to-bench) that reveal new genetically amenable disease models.

Addressing Limitations

In two remaining prospective patients, rapid WGS failed to yield a molecular diagnosis. CMH064 illustrates a current impediment of WGS: It cannot survey every nucleotide in the genome. At 50× aligned coverage of the genome, WGS genotyped at least 95% of the reference genome with greater than 99.95% accuracy, using methods very similar to those used in this study. It has been suggested that this level of completeness is applicable for analyzing personal genomes in a clinical setting. In particular, GC-rich first exons of genes tend to be under-represented. More complete clinical utility of WGS will require higher sequencing depth, multiplatform sequencing and/or alignment methodologies, complementation by exome sequencing, or all three. Combined alignments with two methods sequencing identified about 9% more nucleotide variants than one alone. However, these additions raise the cost of WGS, increase the time to clinical interpretation, and shift the cost-benefit balance.

For genetic disease diagnosis, the genomic regions that harbor known or likely disease mutations, the Mendelianome, must be genotyped accurately. In addition to exons and exon-intron boundaries, the Mendelianome includes some regions in the vicinity of genes that have structural variations or rearrangements. NGS of genome regions that contain pseudogenes, paralogs (genes related by genomic duplication), or repetitive motifs can be problematic. CMH064 had fulminant epidermolysis bullosa (EB). Most EB-associated genes encode large cytoskeletal proteins with regions of constrained amino acid usage, which equate with low nucleotide complexity. In addition, several EB-associated genes have closely related paralogs or pseudogenes. These features impede unambiguous alignment of short reads, which can complicate attribution of variants by NGS. Importantly, this limitation can prevent definitive exclusion of candidate genes. For example, 4.5% of nucleotides in KRT14, an EB-associated gene, had <16-fold high-quality coverage, and thus, can have failed to disclose a heterozygous variant. In CMH064, however, this possibility was excluded by targeted sequencing of the regions of KRT14 known to contain mutations that cause EB.

With CLIA-type adherence to standard operational processes, the component of the Mendelianome for which WGS is effective is extremely reproducible. Thus, the specific diseases, genes, exons, and mutation classes that are qualified for analysis, interpretation, and clinical reporting with WGS can be precisely predicted. This is of critical importance for reporting of differential diagnoses in the genetic disease arena. Thus, although insufficient alone, rapid WGS can still be a cost-effective initial screening tool for differential diagnosis of EB. In our study, all EB-associated genes had >95% nucleotides with high-quality coverage sufficient to exclude heterozygous and homozygous nucleotide variants (>16-fold); nineteen of these genes had >99% nucleotides with this coverage. Hence, for rigorous testing of all EB-associated genes and mutation types, additional studies remain necessary, such as immunohistochemistry, targeted sequencing of uncallable nucleotides, and cytogenetic studies. Of 531 disease genes examined, 52 had pseudogenes, paralogs, repetitive motifs, or mutation types that can complicate WGS for comprehensive mutation detection. The comprehensiveness of WGS can be further enhanced by longer reads, improved alignment methods, and validated algorithms for detecting large or complex variants.

Finally, in singleton cases, such as CMH064, family history is often unrevealing in distinguishing the pattern of inheritance. For example, inheritance of EB can be dominant or recessive. While one plausible heterozygous VUS was detected in a candidate gene in CMH064, it was excluded as a de novo mutation by sequencing of both healthy parents. For evaluation of dominantly inherited diseases, WGS requires either that the parents be concomitantly tested by rapid WGS or by resequencing of candidate de novo variants.

Rapid WGS failed to yield a definitive molecular diagnosis for CMH076. No known mutations were found in 89 disease-associated nuclear genes or the mitochondrial genome. This was an important negative finding, because a molecular diagnosis of several of these genes is "actionable." That is, specific treatments are indicated (such as pyruvate carboxylase deficiency, thiamine responsive congenital acidosis, biotinidase deficiency, fructose 1, 6-bisphosphatase deficiency and coenzyme Q10 deficiency). Likewise, exclusion of actionable diagnoses can prevent empiric institution of inappropriate treatments. Exclusion of known genetic diseases from a differential diagnosis is also of psychosocial benefit to family members and assists in guiding physicians regarding additional testing. There were no VUS with suitable inheritance patterns, in CMH076 or in either of the healthy parents, in known disease genes or in the remaining 929 nuclear-encoded mitochondrial genes.

In contrast to the rapidly declining cost of WGS, the computational cost of genome analysis is largely governed by Moore's law. Sequence alignment, variant calling, and genotyping took 16 hours. Extremely rapid WGS is of practical utility in clinical guidance only when married to equally rapid, cost-effective, deployable and facile interpretation and analysis. The speed of sequence base-calling continues to improve, alignment, and variant-calling. It is likely that this interval can be halved and that HiSeq2500-based rapid WGS can be performed in fewer than 36 hours by the end of 2012. Clinical validation of rapid WGS, however, will take some time.

The following materials and methods were used in the previously disclosed experiments. Retrospective samples, UDT002 and UDT173, were selected from a validation set of 384 samples with known molecular diagnoses for one or more genetic diseases. Seven prospective samples were selected from families with probands that presented in infancy, among 143 individuals without molecular diagnoses that were enrolled between Nov. 22, 2011 and Apr. 4, 2012 for exome or genome sequencing.

The features of the patients' diseases were mapped to likely candidate genes. In part, this was performed manually by a board certified pediatrician and medical geneticist. In part, it was performed automatically by entry of terms describing the patients presentations into a new clinico-pathological correlation tool, SSAGA. It was designed to enable physicians to delimit WGS analyses to genes of causal relevance to individual clinical presentations, in accord with published guidelines for genetic testing in children and with NGS. SSAGA has a menu of 227 clinical terms, arranged in 9 categories (FIG. 3). SNOMED-CT terms map to 591 well-established recessive diseases with known causal genes (Table S1). Phenotype-to-disease-to-gene mapping was informed by Gene Reviews, Online Mendelian Inheritance in Man (OMIM) Clinical Synopsis, Mitocarta and expert physician reviewers.

Upon entry of the features of an individual patient, SSAGA nominates the corresponding superset of relevant diseases and genes, rank ordered by number of matching terms (FIG. 3). It also contains a freeform text box that allows physicians to enter findings for which no SNOMED term exists, clinical term qualifiers, relevant family history, and specific genes of interest. The diagnostic sensitivity of SSAGA improves with use, by manual updating of mappings in cases where nominations failed to include the causal gene. SSAGA is extensible to additional diseases, genes, and clinical terms. Interpretation of results was manual, based on ranking of variant reports yielded by RUNES (Rapid Understanding of Nucleotide variant Effect Software) on SSAGA-prioritized candidate genes, supplemented with expert gene nominations (FIG. 3). In some pedigrees, the presumed pattern(s) of inheritance allowed additional variant ranking, on the basis of obligatory genotypes in affected and unaffected individuals. Aligned sequences containing variants of interest were inspected for veracity in pedigrees using the Integrative Genomics Viewer.

Isolated genomic DNA was prepared for rapid WGS using a modification of the Illumina TruSeq sample preparation (Illumina, Cambridge, UK). Briefly, 500 ng of DNA was sheared using a Covaris S2 Biodisruptor, end repaired, A-tailed and adaptor ligated. PCR was omitted. Libraries were purified using SPRI beads (Beckman Coulter). Quantitation was carried out by real-time PCR. Libraries were denatured using 0.1M NaOH and diluted to 2.8 pM in hybridisation buffer.

Samples for rapid WGS were each loaded onto two flowcells, followed by sequencing on Illumina HiSeq2500 instruments that were set to high throughput mode. Cluster generation, followed by two ×100 cycle sequencing reads, separated by paired-end turnaround, were performed automatically on the instrument.

Isolated genomic DNA was also prepared for Illumina TruSeq exome or custom gene panel sequencing using standard Illumina TruSeq protocols. Enrichment for the custom gene panel was performed twice by Illumina hybrid selection with 20,477 80-nucleotide probes for 8,366 genomic regions, representing exons and 20 intron-exon boundary nucleotides. It encompassed 2,158,661 base pairs (bp), 525 genes and 591 recessive diseases (table S1). The probes were designed to target 350 nucleotide genomic targets, with an average density of 2.4 probes per target (range 2 to 56). Custom gene panel-enriched samples were sequenced on HiSeq 2000 instruments with TruSeq v3 reagents to a depth of >3 GB of singleton 100 bp reads in sample UDT173 and UDT002, respectively. 32.9% and 38.3% of bp were on target defined with a 0-bp extension, representing 469-fold and 501-fold enrichment in sample UDT173 and UDT002, respectively. Exome-enriched samples were enriched twice with standard Illumina hybrid selection and were sequenced on a HiSeq 2000 instruments with TruSeq v3 reagents to a depth of >8 GB of singleton 100 bp reads per sample.

Genome and exome sequencing were performed as research, not in a manner that complies with routine diagnostic tests as defined by the CLIA guidelines.

The following are the results of the sequence analysis. CASAVA 1.8.2 (Illumina) performed gapped ELAND alignment of HiSeq2500 sequences to the reference nuclear and mitochondrial genome sequences (Hg19 and GRCH37 [NC_012920.1], respectively) as well as variant identification. HiSeq 2000 sequences were aligned to the reference nuclear and mitochondrial genome sequences using GSNAP, and variants were identified and genotyped using the GATK. Sequence analysis employed base-call files, FASTQ files that contain sequences and base-call quality scores, the compressed binary version of the Sequence Alignment/Map format (a representation of nucleotide sequence alignments), and Variant Call Format (a format for nucleotide variants). Nucleotide variants were annotated with RUNES, our variant characterization pipeline, which incorporated VEP (Variant Effect Predictor), comparisons to NCBI dbSNP, known disease mutations from the Human Gene Mutation Database, and additional in silico prediction of variant consequences using ENSEMBL and UCSC gene annotations (FIG. 4). RUNES assigned each variant an American College of Medical Genetics (ACMG) pathogenicity category and an allele frequency, on the basis of 722 patients sequenced since October 2011.

Example 1—Patient 1

CMH064 was a male born at 33 weeks gestation with erosive dermatoses. He was delivered vaginally following induction for pre-eclampsia. Desquamation and erythroderma from the hairline to occiput were present at birth. Denuded, hyperpigmented, and partially scarred lesions were noted above the upper lip, over the mentum, and in place of eyebrows. His nails were dystrophic and yellowed. There were no vesicles, pustules, blisters, or mucosal lesions. Family history was positive for psoriasis. His mother had a healthy daughter from a prior union; there was no history of fetal loss. His father was healthy.

Cultures and herpesvirus PCR were negative. He developed severe neutropenia by day three. Skin sloughing worsened. Rigid bronchoscopy and intubation was necessary due to fibrinous oropharyngeal exudate.

Skin biopsy histology revealed acantholysis, loss of cohesion between keratinocytes, and empty lacunae. There was focal dermal infiltration with neutrophils and lymphocytes and complete sloughing of the epidermal layer with focal clefting at the suprabasal layer (FIG. 3b). Immunofluorescence staining was negative for IgA, IgM and IgG except for linear staining for C3. Additional skin immunofluorescence studies revealed slightly reduced plakoglobin and desmoplakin, and normal laminin 332, collagen Types 4, 7 and 17, and plakophilin-1. Electron microscopy confirmed absence of dermo-epidermal junction (DEJ) separation, and showed focally widened spaces between keratinocytes and cell vacuolization from the DEJ to the stratum corneum. Hemidesmosomes were normal. Some keratinocytes had large solitary vacuoles, abnormal condensation of keratin filaments and peri-nuclear pallor. Some desmosomes had ragged edges. There were no intracellular inclusions. Negative laboratory studies included karyotype, Ro, La, Smith, RNP and Scl-70 autoantibodies. Immunoglobulins were unremarkable apart from an elevated serum IgA.

Sloughing of the skin, mucosal surfaces, and cornea continued to worsen and by day 30, his activity level had markedly decreased. His fingers were edematous, discolored, and had retained only 3 nails. On day 39, he developed purulent drainage from facial lesions; Skin cultures were positive for *Escherichia coli* and *Enterococcus faecalis*, and blood cultures for *E. coli*. Antibiotics were administered. He was thrombocytopenic and anemic, necessitating numerous transfusions. On day 47, ultrasound revealed non-occlusive portal vein and left brachiocephalic vein thrombi. By day 54, he developed metabolic acidosis, bloody stools, and persistent tachycardia. Medical interventions were withdrawn and he died on day 54. At autopsy, suprabasal acantholysis was present in the skin and the esophageal mucosa. Dideoxy sequencing of candidate genes KRT5, DSP, JUP, TP63 and KRT14 exons 1, 4 and 6 (the regions harboring most KRT14 mutations) were negative.

Example 2—Patient 2

CMH076 was a male born at term with lactic acidosis, cardiomyopathy and corneal clouding. He was born to a primigravid mother whose pregnancy was notable for decreased movements at 35 weeks gestation. His mother and father were healthy. Variable decelerations in heart rate were noted on the day prior to delivery. Labor was complicated by prolonged rupture of membranes and delivery was by vacuum extraction for meconium staining. Apgar scores were 2, 3, and 5 at one, five, and ten minutes. He had poor respiratory effort, hypotonia and required intubation. Upon transfer on day 2, he had lactic acidosis (lactate 12 mmol/dL), coagulopathy and cloudy corneas. Multiple cultures were negative. Echocardiogram showed chamber enlargement, reduction in biventricular function, noncompaction cardiomyopathy, mild tricuspid insufficiency, and mild aortic insufficiency. Urine testing revealed normal amino acids, and elevated 3-methyglutaconic acid, 3-methylglutaric acid and 2-ethyl-3-hydroxy-propionic acid. Long chain fatty acids, acyl-carnitines, lysosomal hydrolases, β-galactosidase, β-glucuronidase, sphingomyelinase, glucocerebrosidase, α-L-iduronidase, and α-glucosaminidase were normal. Pressors were required for hypotension, and acidosis increased. He was diagnosed with hypoxic ischemic encephalopathy. On day 3, lactate was 28.2 mmol/dL. On day 5, respiratory distress worsened, accompanied by bloody endotracheal secretions; arterial pH was 7.04 and lactate 22.0 mmol/dL. Medical interventions were withdrawn at the family's request, and he expired on day 5. Post-mortem testing by array-comparative genomic hybridization (aCGH) and sequencing for mitochondrial tRNAs and TAZ, associated with Barth syndrome, were normal.

Example 3—Patient 3

CMH172 was a female with intractable epilepsy. She was delivered at 39 weeks gestation by Cesarean section after an uncomplicated pregnancy. No exposure in utero to drugs, alcohol or medications was reported. Birth weight was normal, length 46 cm (<3%), and head circumference 33 cm (<3%). Amniotic fluid was meconium stained. Apgar scores were 6, 7, and 8 at 1, 5, and 10 minutes. Family history was positive for a female cousin with profound intellectual disability and infrequent seizures, and two cousins by a consanguineous marriage who died at 6 and 8 weeks of age of intractable epilepsy; all were from the same small Mexican town as the proband. Seizures started one hour after delivery. Antibiotics were given empirically until cultures and cerebrospinal fluid herpesvirus PCR returned negative. Seizures continued despite multiple antiepileptic medications. Cerebrospinal fluid (CSF, including glycine level and CSF/plasma ratio) and brain magnetic resonance imaging (MRI) were normal. Electroencephalogram (EEG) showed focal epileptiform and sharp wave activity. Blood ammonia, electrolytes, pH and glucose were normal. Oral feeding was poor. She was intubated, and required increasing respiratory support for low $SaO_2$ and bradycardia. Ophthalmologic examination and radiologic skeletal survey were normal. An echocardiogram revealed a patent foramen ovale, tricuspid regurgitation, and peripheral pulmonary stenosis. Her karyotype was normal. Array-CGH was not diagnostic, but multiple tracts of homozygosity suggested shared parental ancestry. A repeat brain MRI at age 3 weeks was normal. Upon transfer at 5 weeks of age, she was small, but symmetric, with bitemporal narrowing, micrognathia, flat nasal bridge, upslanted palpebral fissures, uplifted ear lobes, redundant helices, and fifth finger clinodactyly. She had hypertonia, persistence of cortical thumbs, hyperreflexia, clonus and facial twitching. B6 challenge improved her EEG transiently, followed by return of multifocal sharp waves. Serum amino acids and urine organic acids were normal. Recurrent seizures continued both clinically and by EEG. After lengthy discussion, the parents requested withdrawal of support.

Example—Patient 4

CMH184 was a male with visceral heterotaxy and congenital heart disease (dextro-transposition of the great arteries, total anomalous pulmonary venous return with pulmonary veins connecting to the right atrium, a large ventricular septal defect, pulmonary valve and main pulmonary artery atresia, mildy hypoplastic branch pulmonary arteries, patent ductus arteriosis with ductal-dependant left to right flow, large atrial septal defect with obligate right to left flow). There was situs inversus of the spleen liver and stomach, with the aorta on the right of the spine and inferior vena cava on the left. Family history was positive for a 6 year old brother (CMH185) with the same findings (dextrocardia, ventricular inversion, double outlet right ventricle, pulmonary stenosis, small pulmonary arteries, interrupted inferior vena cava with azygous continuation and situs inversus of the liver and spleen). His parents (mother, CMH186 and father, CMH202) and two other siblings (one male, one female) were healthy. Testing of ZIC3, associated with X-linked recessive Heterotaxy 1, was normal. Patient 4 remains in the NICU and is undergoing cardiac surgery.

One embodiment of the present invention uses a computer program entitled RUNES (Rapid Understanding of Nucleotide variant Effect Software) for database mapping. RUNES is a multi-stage analysis pipeline for annotating and classifying human nucleotide variation detected through short read alignment. The "Variant Warehouse" is a relational database and accompanying lightweight web application that stores characterization results and makes them available through a simple query and display interface. The Variant Warehouse is designed to store the characterization results of all nucleotide variants detected as part of conducted sequencing projects and is continually updated as projects are completed.

The technical architecture of RUNES is a command line tool that executed in a Linux or other Unix environment. RUNES is written in Java 1.6 but relies heavily on the execution of external processes and tools (written in Perl and other languages) as it proceeds through the characterization stages.

The Variant Warehouse database is a relational database deployed on a MySQL 5.5 server, though no RDBMS specific features are utilized other then the MySQL specific tools for bulk loading of delimited data. The Variant Warehouse web application is a Ruby on Rails 3.2 application running through either the built-in Rails web server or through Apache web server with the Passenger module. Data is presented in standard HTML. Linux servers that run the CentOS release 5.5 operating system can be used.

A complete pipeline run follows this progression:
1. De-redundification of variants from input samples. This is done by reading through all sample variant lists and keeping the superset of all variants (with no duplicates) for characterization.
2. Comparison with Variant Warehouse database to identify novel variants.
3. Characterization stages (described in detail below)
4. Gathering and aggregation of variant annotations
5. Variant classification
6. Creation of bulk data import files and loading to database The de-redundification processes require input variant lists to be sorted lexically by reference sequence (Chr), start position, stop position and variant allele (so that chromosomes are sorted as 1, 10, 11 . . . 19, 2, 20, 21 instead of numerically as 1, 2, 3 . . . etc.). This reliance on sort order enables much improved efficiency and scalability. Lexical sorting of reference sequences is required given the presence of non-numeric reference sequences such as X, Y or MT.

RUNES is designed to evaluate a variant once and store the results, meaning a variant's characterization can only be updated (e.g. due to updates to software or reference data) by removing the existing variant record from the Variant Warehouse db and re-running the variant through RUNES. Consequently, the entire variant warehouse is expected to be versioned as a whole with new software and data releases being accompanied by a complete repopulation of the database.

RUNES takes as input 1-200 variant files, with each file usually representing all variants detected for a single sample. The upper limit of 200 is currently a hard-coded limit but can be adjusted upwards, if needed. Note, however, that this version of the pipeline is somewhat limited by RAM requirements so that the upper limit on the number of variants that can be processed in a single pipeline run is around 3-4 million variants using a 32 GB max memory setting for Java Virtual Machine. With additional compute resources, the JVM can be expanded to at least 512 GB.

Reading and writing of variant files is abstracted in the pipeline so that several different file formats can be handled. In one embodiment the input format can be a CSV format. Alternatively, (the standard that arose from the 1000 Genomes project) VCF can be used as input as well as other formats as desired. All input files for a single pipeline run can be in the same format, although file-specific formats can be used as desired.

Characterization is divided into multiple independent stages that each read through the de-redundified variant list and record zero or more simple key/value annotations for each variant according to the type of characterization being performed by the stage. Characterizations made by each stage are done orthogonally to other stages without taking their annotation into account. At the end of characterization, variant annotations are aggregated and all submitted to a variant classifier which assigns an American College of Medical Genetics (ACMG) category to each based on the accumulated annotation evidence, with the most damaging category achieved being the final categorization.

Characterization stages use a variety of software and data from both internal and external sources. All stages follow the basic pattern of reading data from a VariantReader and writing variant annotations using a VariantWriter. The stages are:
1. ENSEMBL Variant Effect Predictor (VEP)
2. Comparison with dbSNP
3. Splice impact evaluator
4. Transcript context characterizer
5. Comparison with Human Gene Mutation Database (HGMD/GenomeTrax)

Each of these stages is described in detail below.

ENSEMBL Variant Effect Predictor.

VEP is a Perl script that uses the core and variation ENSEMBL APIs and databases to characterize variants. While VEP is able to use the publicly hosted ENSEMBL databases for querying, local copies of the databases can be maintained for performance reasons. ENSEMBL characterization can be performed with version 63_37 of the database and API.

The following variant annotations are recorded from ENSEMBL output:
Affected genes, transcripts and proteins
Reference and variant amino acids
Reference and variant codons cDNA position of variant
CDS position of variant
AA sequence position of variant
HGVS_c and HGVS_p variant notations
SIFT score and prediction
PolyPhen2 score and prediction
ConDel score and prediction (recorded but not included in classification)

In addition to the above, BLOSUM62 score for an AA change and translation impact of AA change are recorded using conventional modules. VEP records annotations in reference to ENSEMBL gene, transcript and protein identifiers (though HGNC gene symbol is also supplied). Wherever possible, transcript and protein identifiers are translated to their RefSeq equivalents and recorded in the Variant Warehouse using the RefSeq id. Translation is done using a combination of resources from both NCBI and ENSEMBL. A direct comparison shows that there are some differences between RefSeq and ENSEMBL sequence versions of the same transcript; primarily this seems to be in the length of 5' and 3' untranslated regions with the CDS remaining constant between the two. Given this ambiguity, transcript specific annotations are still recorded in RefSeq style, though to ensure accuracy, HGVS notations are preserved using the ENSEMBL identifiers and no attempt is made to translate cDNA positions. Additionally, ENSEMBL has many transcripts that have no RefSeq equivalent—annotations made to one of these transcripts are currently discarded and not stored in the Variant Warehouse.

A comparison of variants to all known data in dbSNP is performed to link variants to dbSNP wherever possible. If a match is found, the following info is recorded:
dbSNP rsID
Global Minor Allele Frequency (GMAF)
Snp Clinical Significance (SCS)

GMAF and SCS are not recorded for all variants. SCS can be recorded in dbSNP using the categories of unknown, untested, non-pathogenic, probable-non-pathogenic, probable-pathogenic, pathogenic, drug-response, histocompatibility and other. All values can be recorded by RUNES, though only pathogenic is relevant to ACMG classification. dbSNP data can be supplied in a VCF 4.0 file; comparisons can be made to dbSNP build 134.

The dbSNP VCF file reports variants in the pseudo-autosomal region (PAR) of chromosomes X & Y as being on the 'PAR' chromosome, though the coordinates reported appear to be the coordinates for the Y PAR (evaluated by nmiller). For the purposes of this comparison, a version of the dbSNP variant can be created for both the Y and the corresponding X PAR positions so that a match will be made to experimental variants detected on either chromosome.

The Splice Impact Evaluator is a tool for characterizing a variant's putative effect on splicing. This evaluation can be done by comparing the positions of each variant to the following splice site contexts around each annotated exon:

3_flank 5 bp preceding polyY tract in intron
3_polyY 13 bp polyY tract on 3' end of intron before acceptor core splice site
acceptor 2 bp core splice site on 3' end of intron (AG)
3_exonic first base on exon after 3' core of intron (G)
5_exonic last 2 bp 3' end of exon (AG)
donor 2 bp core splice site on '5 end of intron (GT)
5_flank 4 bp after core site on 5' of intron
5_intronic 14 bp after 5_flank on 5' of intron The following diagram illustrates the splice site contexts used for splice impact characterization as well as the ACMG category assigned to variants appearing in each region: -=intron; *=exon ACMG Variant Category

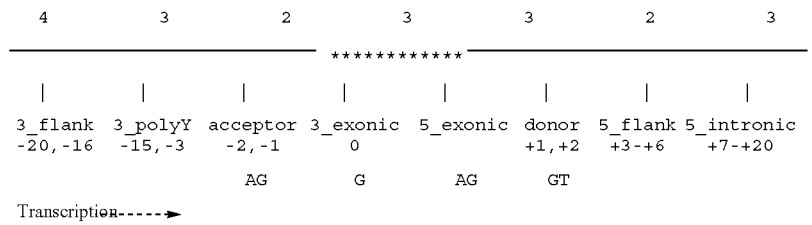

The splice evaluator software can be implemented in the Perl programming language and consists of two separate scripts. The first script reads through a file of reference gene/transcript annotations in Gene Transfer Format (GTF) and outputs a GTF file containing the genomic coordinates of the above splice site context regions for each exonic region in the reference annotation. This splice region database is created once as part of the setup for RUNES. The second script, run as part of RUNES itself, simply compares all variants to the splice region database and outputs which regions the variant overlaps with.

Transcript Context Characterizer.

Variants are compared to the reference gene and transcript annotation to determine the transcript-specific effects of a variant. A positional comparison is made to determine what transcripts a variant overlaps with, then for each transcript the transcript context (intron, exon or CDS) and the estimated translational impact of the variant are recorded.

Translational impact is recorded as a set of enumerated values, so that each variant will have only one associated impact.

The values recorded are:

| Recorded Impact | Description |
| --- | --- |
| None | no impact; synonymous substitution or intronic |
| non-synonymous | substitution causing amino acid change |
| premature stop | creation of premature stop codon through non-synonymous substitution as well as insertion or deletion of bases |
| disruption of stop | nonsense disruption of stop codon, including deletion of entire codon |
| loss of initiation | nonsense disruption of start codon, including deletion of codon or non-synonymous substitution changing first AA base from Methionine to anything else |

| Recorded Impact | Description |
| --- | --- |
| disruption of splicing | deletion across an intron/CDS boundary that potentially affects splicing (somewhat redundant with the splice effect evaluator stage) |
| Frameshift | indel that changes translation frame by adding or removing bases from the coding sequence, including deletions within a single exon as well as spanning multiple exons |
| in-frame in/del | insertion or deletion in the coding region that preserves translation frame |
| transcript deletion | deletion of entire transcript |

A comparison is made to the Human Gene Mutation Database (HGMD) to determine whether any detected variants have been previously identified as disease causing mutations. To make this comparison, RUNES uses data from GenomeTrax, a BioBase product that contains all data from the HGMD in a flat file format (Generic Feature Format [GFF3]) that is more easily integrated into large scale analysis programs. In the characterization stage, each variant is compared to the known mutations from GenomeTrax; if a match is found, the following data is recorded for each variant:

- variant type (e.g. mismatch, insertion, deletion)
- mutation type (e.g. disease causing mutation, disease associated polymorphism)
- HGMD accession #
- nucleotide change
- associated disease
- Entrez-Gene id of affected gene To address issues in HGMD data as well as in the precise mapping of some in/del variants, the comparison of insertion and deletion variants to HGMD variants is done 'fuzzily' so that a match is called if the following conditions are met:

- insertion or deletion variants are within 5 bp (configurable) upstream or downstream of the recorded HGMD variant position
- variants are of the same type (matching rules below)
- variant have the same length, where length is 1 for substitutions, the number of deleted bases or the number of inserted bases. An exception is made when matching HGMD in/del variants where allele size comparison is unlikely to match given the complexity of variant described: in these cases, length comparison is skipped.

Substitutions are not treated in this way, rather they will be matched if they have the exact same position only. Substitution allele is not compared, so that a C>G substitution variant will match an C>T HGMD variant.

HGMD uses a wider vocabulary to describe variants than RUNES (which currently calls all variants substitution, insertion or deletion). For purposes of comparison, the following table shows what types will be considered a match.

| HGMD Type | RUNES type |
| --- | --- |
| M—missense or nonsense single nucleotide mutation | Substitution |
| S—splice site mutation | |
| D—deletion | Deletion |
| G—gross* deletion | |
| I—insertion | Insertion |
| N—gross* insertion/deletion | insertion/deletion |
| X—In/del | (without length comparison) |
| R—promoter mutation | unhandled |
| E—amplet | |
| P—complex rearrangement | |

*gross refers to lesions covering >20 nt. GSNAP + GATK should detect insertions up to 60 bp and deletions up to 10 kbp.

GenomeTrax specifies the above types, however our current data files contain only S, M, D, X and I variant types. The matching rules are deliberately slightly lax, taking the strategy that this automated comparison can overagressively call matches that will be sorted out through manual curation during review of patient specific results.

At the end of characterization, RUNES has recorded multiple independent characterization assertions for each variant. Further evaluation requires that all characterization assertions be first aggregated for each variant so that all information can considered together. Aggregation is done simply by reading through files that contain independent annotations from each characterization stage and collecting them in memory for each variant. This in-memory merging represents the single hardware limiting factor of RUNES since each variant instance and all its associated annotation is held in RAM during this step (causing memory exhaustion if more variants are being characterized than available RAM can handle).

During this step, transcript specific annotations are further aggregated so that all information on a variant's effect on a single transcript and in all transcripts for a given gene can be considered together. Annotations that are made to the variant itself without being part of a specific transcript context (e.g. dbSNP rsID) remain properties of the variant.

Variant classification is the final stage of variant characterization and consists of assigning an interpretive category representing clinical significance to each variant. Every variant will receive a classification. RUNES uses categories recommended by the American College of Medical Geneticists—these are listed along with the criteria used for including a variant in each category:

| Category | Description | Criteria |
| --- | --- | --- |
| 1 | Previously reported, recognized cause of the disorder | HGMD variant type of 'Disease Mutant' dbSNP Snp Clinical Significance of 'pathogenic' |
| 2 | Novel, of a type expected to cause the disorder | loss of initiation premature stop codon disruption of stop codon whole transcript deletion frameshifting in/del disruption of splicing through deletion causing CDS/intron fusion overlap with splice donor or acceptor sites. |
| 3 | Novel, can or can not be causal | non-synonymous substitution in-frame in/del disruption of polypyrimidine tract overlap with 5' exonic, 5' flank or 3' exonic splice contexts |
| 4 | Novel, probably not causal of disease | all variants not in categories 1-3 synonymous AA changes overlap with 5' intronic or 3' flank splice contexts pyrimidine substitutions in polypyrimidine tract, other intronic variants dbSNP GMAF of greater than 0.02 |

-continued

| Category | Description | Criteria |
|---|---|---|
| 5 | Known neutral variant | not used |
| 6 | Not known/expected to cause of disease but associated with a clinical presentation | not used |

The ACMG categories rely heavily on the identification of novel versus known variants which implies comparison to external variation databases. The current VCP uses HGMD and dbSNP to fulfill this role.

RUNES categorizes any variants as Category 5 or Category 6, meaning that most novel variants without clear pathogenicity will end up as Category 4. It is expected that as these existing resources improve or as additional clinical grade databases become available this categorization will be updated to include these categories.

Classification will assign membership to a category if the variant has any of the criteria for that category. Evaluation for each category is done independently so that each step considers only the criteria relevant to that category without taking into account membership in any other category (i.e. while evaluating for Category 2, there is no check to see if possibly variant belongs to Category 1 and therefore shouldn't be a member of Category 2). A variant will receive the most severe classification possible—this is done by evaluating category membership in a prioritized manner so that a variant is only evaluated for a lower category if it did not get put in a higher category (i.e. check is only made for Category 3 if variant was not put into Categories 1 or 2).

The exception to this 'keep the most severe category' rule is if dbSNP reports a Global Minor Allele Frequence greater than 0.02—in this case, RUNES will assign Category 4 regardless of any other predicted effect. This overriding usage of the GMAF is an accommodation to the incomplete state of reference databases and is used under the assumption that any variant with that frequency in the population cannot be causative of catastrophic disease. RUNES' use of the GMAF is currently imperfect as it does not recognize a limited number cases where the reported GMAF refers to the reference allele rather than the variant allele, meaning that some variants will not be correctly recognized as common polymorphisms.

The Variant Warehouse records a Minor Allele Frequency for all variants observed through CPGM sequencing projects. This frequency value simply records the number of samples that have each variant in them along with the total number of samples sequenced to date. These values are recalculated for every variant in the Variant Warehouse after the completion of each VCP run so that the value properly records the presence or absence of each variant across every sample represented in the database. This calculation can be run as a separate process. The frequency calculation can be implemented as a Hadoop Map/Reduce job using Java 1.6.

Variants are detected using the GRCh37.p5 build of the human reference genome. Gene and transcript annotations are compiled from a variety of sources including:

UCSC RefSeq genes

ENSEMBL mitochondrial genes

HGNC symbols

OMIM

Other external data sources include:

HGMD Pro/Genome Trax [v. 2011.3]

ENSEMBL core and variant databases [v63_37]

dbSNP [build 134]

NCBI's ClinVar Database

NCBI currently is making plans for a new database, ClinVar, which is intended to serve as a publicly available, clinical grade mutation database. RUNES can be updated to compare variants against ClinVar data as it becomes available; additionally, efforts will be made to deposit data from the variant warehouse db into ClinVar as NCBI finalizes the mechanisms for accepting such submissions.

The Variant Warehouse currently makes characterization results available through a simple query and display interface on a 1-by-1 basis. The immediate plans are to incorporate a single sample's variant calls with VCP annotations for an interpretation report on a sample-by-sample basis. Batch upload of characterization results will be available in a future release.

A method is disclosed for a computer-assisted and largely automated ascertainment of clinical symptoms and signs, integration of those clinical features (Sx), fitting to all or most disease states, and interpretation of a whole or most of a genome sequence of a patient with a suspected genetic disease based, in part, on the ranking of likelihood of diseases in a differential diagnosis list based on those mappings in order to arrive at a best singular or sparse list of clinical diagnoses (Dx). This differs from the currently used approaches which evaluate the relative pathogenic potential of all variants on a gene-by-gene basis across the genome and then to fit those interpreted variants to the clinical picture or to report them without integration with the clinical picture. The method of the present invention uses symptoms, signs and/or laboratory values (Sx), and/or suspected mode of inheritance (dominant, recessive, X-linked, any, maternal) obtained by a physician or other healthcare provider (such as a nurse, genetic counselor) or a patient or their parents (in the case of childhood diseases) as inputs, performs (ideally) multinomial, probabilistic classification and mapping to diseases, assisted by comprehensive databases of known genome sequence variations and known associated genes and known associated genetic diseases and known associated symptoms to provide an automated probabilistic classification (interpretation) of the clinical picture, that prioritizes genes and genomic regions for guidance of interpretation of genome information in order to reach a Dx that is the likely cause of the patient's symptoms and signs and genetic disease.

For each genetic disease there exists a specific set of phenotypes, set of genes and set of causal genome variations (mutations). Each member is a "class" in terms of classification algorithms. The problem is to find the best matching "class" for a given set of "features" (syndromes+patient data such as gender, race and age) based on the sum of the previous experience. There are many different classification algorithms including, but not limited to, (1) neural networks, (2) logistic regression, (3) bayes classifiers, (4) decision trees, and (5) fuzzy logic.

Furthermore, a feature of the disclosed system of the present invention is continuous self-learning, meaning that the data from each patient for whom the system is used is anonymously applied to further "train" or update the clinical feature to disease to gene to variant classifiers or mappings. After each training event these mappings will be better able to predict or impute disease causality for variants based on symptoms from the classified data and weight with the updated and more accurate probabilities. As each new patient's data is entered and the ordering healthcare provider provides subsequent feedback about the truth of the conclusions, the system is able to add this to the "training" set and adjust the probabilities and algorithms correspondingly.

The algorithm chosen is influenced by the fact that the training data that we currently have is very limited (sparse), incomplete, and contains ascertainment and other errors. The algorithm should still operate reasonably well in terms of accuracy and reproducibility and sensitivity of diagnostic decisions since likelihood of truth of all associations is initially governed by public databases. An example of a limitation in the data is that the training set cannot include all possible mutations. Thus "manual" rules or initial empirical knowledge can also be used in the system to assist the algorithm, especially in the initial stages of program training.

The proper description of the items, such as "patient" and "symptom" and "disease" is important in for the system to correctly classify the various data items. The proper description of the items used in the system for classification can greatly help the algorithms. Therefore, symptoms and patients need to be described in convenient terms for both physician and algorithm. An example is the use of standardized terms and controlled vocabularies, such as Online Mendelian Inheritance in Man (OMIM), Entrez gene, the Gene Ontology (GO), the database of single nucleotide polymorphisms (dbSNP), the Human Gene Mutation Database (HGMD), the Systematized Nomenclature Of Medicine Clinical Terms—Clinical Terms (SNOMED-CT), Human Genome Variation Society nomenclature (HGVS), the London Medical Databases (LMD), and the Human Phenotype Ontology (HPO).

The problem is that the items, such as symptoms (Sx, HPO, LMD or SNOMED-CT), are diverse and knowledge or identification in individual patients can be incomplete or inaccurate. For instance, it is not always possible to tell what tissue is affected by a disease. Likewise, the networks, pathways and connections between individual elements can be incomplete or inaccurate.

There are several different types of mutations, such as deletions, duplications, translocations, point mutations and other mutation types. These classes of mutations are different and the description of these mutations will be different. For clinical and other features there can be weighting associated with severity or duration or frequency or other attributes of the clinical or laboratory feature. Knowledge representation through linguistic variables characterized by means of fuzzy qualifications and linguistic modifiers that slightly change the qualifications are incorporated ("hedges"). These hedges can be used symbolically, though in a way compatible with logic systems. Their use provides an interface between numerical and symbolic descriptions of evidence. They can help to give elements of comparison for fuzzy implications, and yield a kind of classification of the available tools. They can allow gradual knowledge to be used in the context of deduction rules.1.

Figure 5:
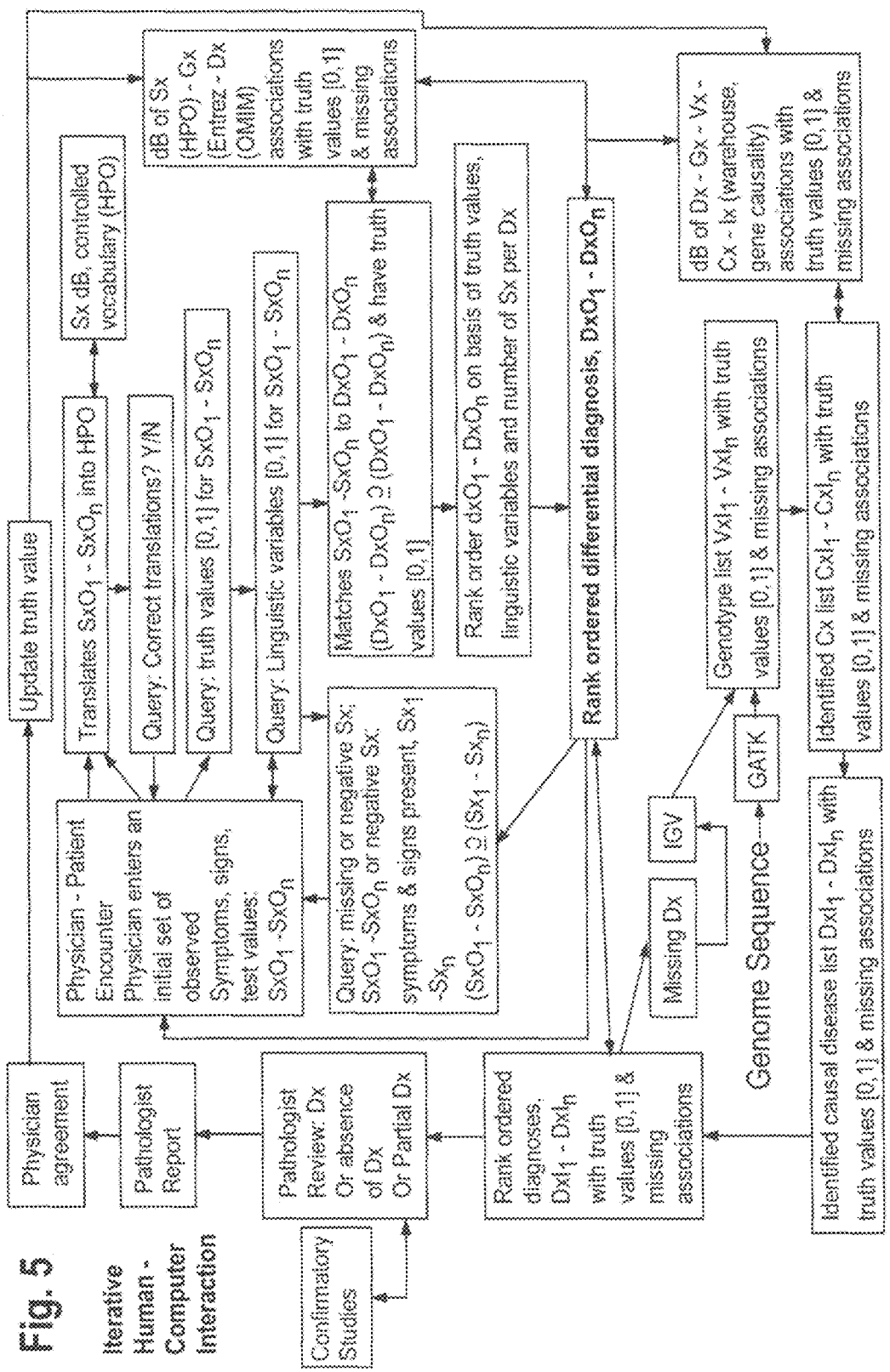
FIG. 5 is an illustration of a system for the disease diagnosis of a patient of the present invention.

Referring to FIG. 5, the physician enters an initial clinical feature or set of clinical features that is present in that patient (Sx) being one or more of the following: symptoms, clinical signs or laboratory test values observed in the patient with a suspected genetic disease, observed at that time, or previously observed in that patient (yellow box). As noted above, these can be qualitative or quantitative values and can have modifiers (or hedges) with regard to duration, severity, likelihood of being true, etc. The physician enters at least one such clinical feature (Sx) observed at that time or reported to have occurred by the patient or other data sources (SxO, Sx observed) into the system. Sx are regarded as true values. SxO are a representation of Sx that have some likelihood of being true.

Since a goal of genome testing is earliest diagnosis of genetic diseases, or elimination of differential diagnoses, or guidance with regard to prognosis or drug response, or other treatment response, in order to maximize the ability to change the disease course, SxO can be a small subset of the Sx of the full-blown disease. Thus, at the time of patient evaluation, the full blown disease features can not yet be discernable. SxO can also be coincidental findings that are not associated with the disease. SxO can also have been mis-ascertained or mis-identified and with no relationship to Sx. In contrast, database entries for the clinical features of a full-blown genetic disease can cause a misdirected differential diagnosis if trying to "fit" the smaller subset of observed symptoms (SxO) to that of the full-blown clinical picture (featuring all possible Sx). For such reasons, as detailed below, there is a need for databases of clinical features that are weighted, for example, according to those that are present at early times of disease, when genetic tests are likely to be ordered. Weighting should also include discrimination of Sx that are always present in that disease from those that are not always present. There is also a need, as detailed below, for programs that are self-learning based on accumulated patient Sx for which definitive (or molecular) Dx have been obtained previously in order to thereby make novel Sx-Dx associations or to update truth values.

The physician can enter SxO values by typing them or by selection from menus or by more intuitive methods, such as verbally or clicking on pictures of regions of the body to drill down to the feature desired. Such hierarchical arrangements of Sx, as exemplified, for example, by HPO and SNOMED-CT, are necessary since Sx databases remain incomplete and unable to classify every possible Sx. Thus, there is a need to accommodate approximations of SxO. Entry is directly or indirectly into an electronic interface on a program or tablet or other interface with a computer. Alternatively paper or other version of the clinical features can be entered subsequently remotely from the patient-physician encounter. An advantage of a human-computer interface-based clinical feature entry is the ability to enter values remotely from the site at which genetic testing or analysis or interpretation is performed. Another advantage is that the interaction can be dynamic. The components of the human-computer interface can be deployed locally and the data transmitted to the testing center. The interface could be in a different part of the country or in another country. Such a system enables physicians in remote locations to obtain differential diagnoses dynamically based on known or probable Sx-Dx association, and request specific testing based on those suggested conditions. Such a system can allow generalist physicians to receive dynamic guidance allowing ordering of highly complex genetic or genomic or other tests at the time of ordering, for which the physician can have little experience. The quality of the differential diagnosis received and specific genetic tests ordered is proportional to the completeness and nuance of the clinical features entered by the physician. In order to proceed in submitting a test order, requisite data field(s) must be complete to ensure sufficient data entry. Such a system has the ability to educate or guide a physician in real time (dynamically) about genetic disorder presentations and/or Sx-Sx and/or Sx-Dx and/or Dx-Dx associations by providing a differential diagnosis or other lists or feedback or linkouts to other databases and information resources. In addition, particular, specific disease names can be queried, for example by a mouse click on the disease, in order to obtain a full list of known associated features or associated genes or hyperlinks to external sources of information regarding the disease, prognosis, complications, inheritance, incidence or treatments.

A human-computer interface translates the entered clinical value(s) (observed symptoms, $SxO_1$-$SxO_n$) into the corresponding term from standardized vocabulary, such as the Human Phenotype Ontology (HPO, http://www.human-phenotype-ontology.org/). The HPO, for example, contains over 10,000 standardized clinical terms with appropriate numeric values. Particular features can be queried, for example by a mouse click on the feature, in order to obtain a definition, means of ascertainment, associated features or associated diseases and examplars. The latter are particularly valuable in conditions such as skin rashes or dysmorphology terms, where distinctions can be subtle and non-evident to non-expert physicians and approximations can be necessary for data entry.

The program performs mapping(s) of the clinical value to a standardized feature term(s) automatically and with short latency in order to provide feedback to the physician in order to allow further physician feedback with regard to translation and accuracy and precision of the term associations. The physician is prompted with the translated term and is requested to enter a binary or qualitative response as to whether the translated term is acceptable. If not, the process is re-iterated with the program returning a nearest neighbor or parent term or next pathway or network member other term with some association to the original term.

Upon physician acceptance of a term, the program prompts the physician with short latency whether the term is definitely present or has a lesser likelihood of being present in the patient or other linguistic hedges. The physician can either reply in a binary or continuous manner, indicative of a [0,1] truth value. Clinical features, such as jaundice, when detected by scleral discoloration, can be highly subjective, and lower truth values can be entered. Likewise, the timing of a heart murmur or associated sounds such as splitting of valve closure, can be subjective. The program then prompts the physician with short latency for another linguistic variable [0,1] or linguistic hedge, which qualifies the severity or extent of the symptom or sign or test value. This can be particularly valuable with continuous clinical features, such as body temperature or white cell count, or clinical features that vary by age, such as height or weight or features that have different reference ranges in different populations. It is possible to provide automated nomograms for such variables to convert values to age-appropriate distributions or ranges, together with distance or deviations from averages. It is also possible to provide automated values for clinical indices that are derived from several clinical values, such as the Glasgow Coma Score or APACHE II or SOFA score, and attendant clinical descriptors. The program then maps each Sx to one or more diagnoses (Dx) by lookup of a database of Sx-Dx associations, such as Online Mendelian Inheritance in Man (OMIM; http://www.ncbi.nlm.nih.gov/omim) or derivative matrices, such as Phenomizer. OMIM contains Sx-Dx-gene (Gx) associations for over 12,000 genes. These associations have been mapped using standard vocabularies, for example, http://www.human-phenotype-ontology.org/contao/index.php/downloads.html. Sx-Dx associations can be one-to-one, one-to-many, or many-to-one.

As noted above, the absence of a particular Sx does not obviate a Dx, and the list of Dx is the superset of the Dx associated with each Sx, for the point of deriving a differential diagnosis list. For purposes of interpretation, the sum of the number, or sum of the truth values, or sum of the linguistic variables, or some other means of integrating and weighting the various features, or a combination thereof, can be used to prioritize Dx within a list. In addition, some Sx are pathognomonic of particular Dx, and can be ranked or weighted as higher or of greater discriminatory power than others. However, such weightings can be misleading, since clinical heterogeneity of some disorders is poorly defined. Hence the logic for adopting a superset of Dx and for updating associations based on experience.

The OMIM associations or other Sx-Dx associations have variable truth values [0,1] and such matrices have missing associations, reflecting lacking knowledge of the full spectrum of attendant Sx. The program attaches to each Dx a rank [0,1], based on the truth value of the Sx-Gx-Dx association, weighting based on linguistic variables for each Sx, and the number of Sx for each Dx. The program displays the resultant ranked differential diagnosis to the physician. Where a Dx is missing an observed Sx that the program ranks as most relevant (for example, matches only one Sx, or is missing an Sx with a truth value approximating 1), the program will automatically query the physician whether that Sx is present. Where the physician feels that a Dx is missing from the differential Dx list, he/she can add that Dx to the list of differential Dx, further eliciting queries to explore the rationale for such entries. Such entries will be analyzed by the program as detailed above and the process is continued iteratively until the physician completes the interaction. Negative Sx (truth values approximating 0) can also nominated by the program for query of the physician, where the program ranks such the absence of a Sx as highly pertinent for differential Dx, as in the case of pathognomonic Sx. Likewise, the physician can enter negative values for particular Sx that are not present. This is particularly useful where the physician has a knowledge of differential Dx and is aware of the utility of missing Sx.

Subsequently, a genome or partial genome sequence is obtained from a patient sample. Variants and variant genotypes (Vx) are imputed or calculated by the program from the nucleotide sequence using comparisons with reference genome sequences, such as combinations of alignment algorithms and variant detection method, such the GATK or iSAAC or another program, generating a patient-specific set of identified variants and variant genotypes (VxI, variant and whether present on one or both strands), $VxI_1$-$VxI_n$ with truth values [0,1] and missing associations. In the case of GATK, truth values are calculated by Bayesian inference. In the case of copy number variants, the genotype is continuous with discrete numeric values and requires a separate field for description. For a genome sequence, the list of variants identified in a given patient (VxI) can be greater than 4 million. VxI are a subset of all genomic variants present in that patient (false negatives). VxI include variants that are not present in that patient's genome (false positives). VxI also contain Vx that have wrong genotypes. Causality of these variants for a particular disease (Cx) is imputed according to a rule set, such as described[7], and comparisons with a database of Genes (Gx)-Vx-Cx-Ix-Dx (for example, the Children's Mercy "warehouse", gene causality) associations with truth values [0,1] and missing associations are performed, where, for example, the Vx is a variant of uncertain significance (VUS). Ix represents the inheritance pattern of each Dx with truth values [0,1] and missing associations, and is used to associate the VxI with causality for a given Dx. Cx can be assisted by various interpretive tools, such as SIFT, Polyphen, BLOSUM, or PhyloP, which provide accessory data, or truth value alterations, regarding causality. Such interpretations can be performed automatically. Consequent truth values can be calculated according to different weightings of the cumulative evidence of causality. Large numbers of interpretive tools can be employed, and nomograms for their combined use can be derived[7]. A set of identified (as opposed to observed) causal diseases $DxI_1$-$DxI_n$ is generated, with truth values [0,1] and missing associations (blue box). These DxI can be rank ordered or prioritized by the program for likelihood of being the definitive Dx, as previously described, with the accumulated truth values, linguistic variables and number of relevant Sx, or combinations thereof. Such ranking can also be performed manually using, for example, VIKING. Incomplete Dx (DxI), represented, for example, by partial causative genotypes, will also be selected by the program where most relevant to the observed Dx (DxO), for further analysis. In such cases, the operator (or interpreter, such as a medical geneticist or clinical geneticist or molecular pathologist, "pathologist") will be queried by the program to inspect the relevant region with the Integrated Genomics Viewer (IGV) or UCSC browser, or similar viewer of sequence alignment data to ascertain whether the variant or genotype that has been missed or miscalled by the GATK or other method of variant identification in sequence information. Manual entry of Cx or Vx genotype corrections is provided. Manual reordering or reinterpretation or reweighting of Cx, Vx or Dx can be performed by the pathologist or other interpreter (pathologist).

Following such iterative steps, the pathologist completes his/her review of the DxI list and associated weightings, for final interpretation. Where indicated, follow up or confirmatory studies can be ordered. Literature references can be hyperlinked to each Cx, providing an ability to review literature evidence for causality. The pathologist can then issue or sign out the program report, together with human interpretation notes, and this is provided back to the ordering physician. This can alternatively be automated by the program. If the pathologist is not immediately available for review, the rank ordered diagnoses can be reported as a provisional report, together with truth values. Where the report is electronic, such a system has the ability to teach a physician or patient about genetic disorder presentations by providing a differential diagnosis list. The Dx can be queried, for example by a mouse click on the disease, in order to obtain a full list of associated features or hyperlinks to external sources of information regarding the disease, prognosis, complications, inheritance, incidence, treatments, support groups, or other information, such as referrals to particular physicians for additional therapeutic or prognostic or other evaluations. Such a system can also be used for subsequent physician-patient encounters to add Sx or to weight Sx differently with time. Such subsequent entries can alter the Dx set weightings, providing such information to the pathologist or physician. Such a system can also be self-updating as truth values for data are updated, and can provide such additional consequences for Dx to the pathologist or physician.

Upon ascertainment of a definitive diagnosis, the database are updated with new truth values and associations for Sx, Dx, Gx, Vx, Cx, and Ix, providing a learning capacity from patient results. As noted above, such new associations and resultant reweighting of cumulative truth values, are particularly important where disease evolution occurs temporally and in cases of clinical or genetic heterogeneity. The cumulative frequency of Vx (allele frequency) is also particularly important in distinguishing Cx truth values, since many Cx listed in available databases, such as HGMD, are false positives. Thus, a Vx with high allele frequency (for example greater than 1%) in a given population, can indicate that the Vx-Cx association is false.

Each step of the process can use a logical model, such as probabilistic Bayesian inference or fuzzy logic, trained by a training (or self-learning) set, and then tested and updated with patient data. One embodiment of the system is a self-learning module that is a component of a knowledge base that is operable to automatically adjust the ranking or ordering of the associations based on the clinical and observed symptoms of the patient. A module is described as self-learning because it teaches and strengthens the associations (between the clinical features, diagnoses, genes, and gene variants) that are in the knowledge base. These strengthened associations are then used to reprioritize the diagnoses list.

The initial embodiment of these methods is the Center for Pediatric Genomic Medicine (CPGM) pipeline containing SSAGA, RUNES, Variant Warehouse and VIKING. SSAGA, RUNES and Variant Warehouse have already been disclosed hereinabove, with application to approximately 500 Dx and approximately 250 Sx. By incorporation of, for example, HPO terms and Phenomizer associations, SSAGA can be extended as described above.

Figure 6:
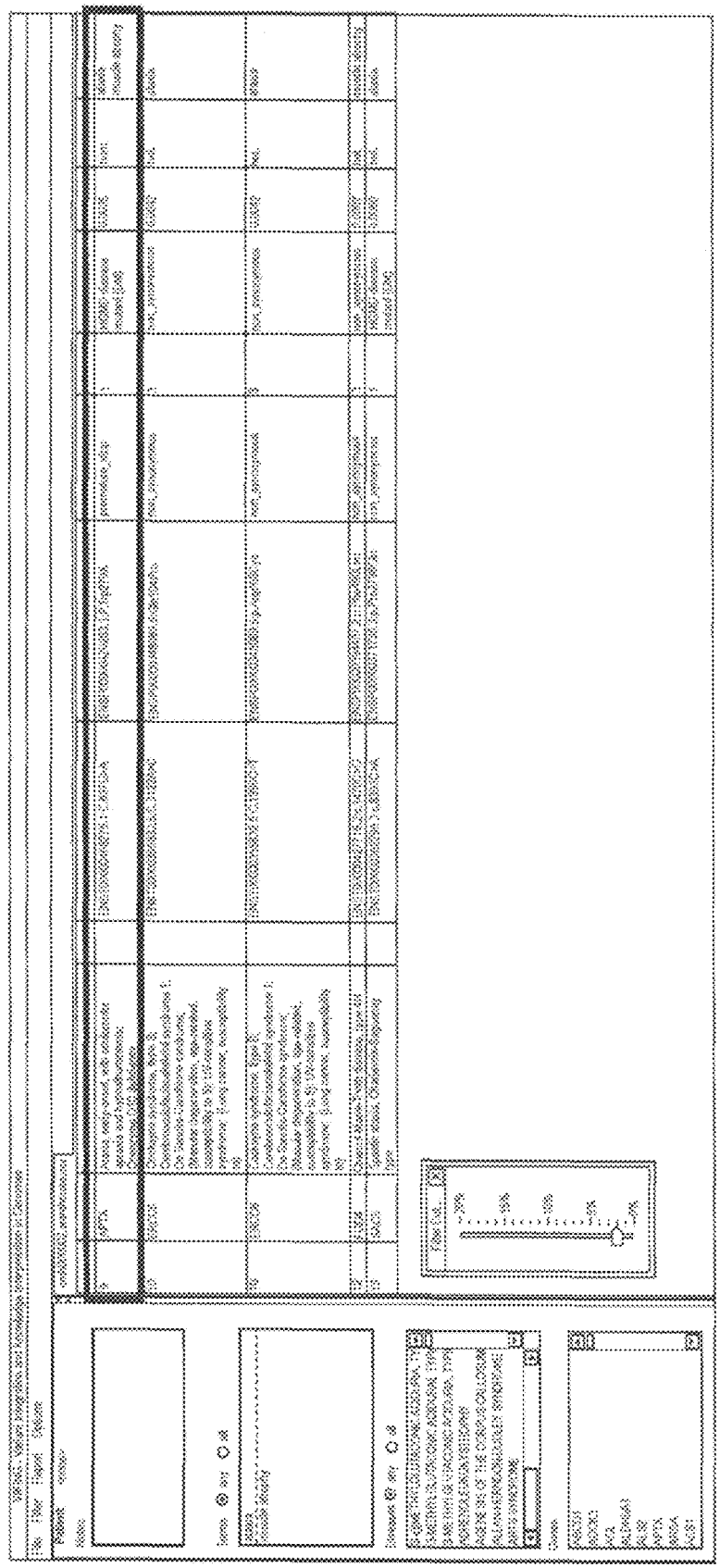
FIG. 6 is an illustration of the system of the present invention of FIG. 5 where the system is displaying SSAGA symptoms, diseases and genes on the left and a filter ranked variant list shows only mutation in genes from the SSAGA list.
Figure 7:
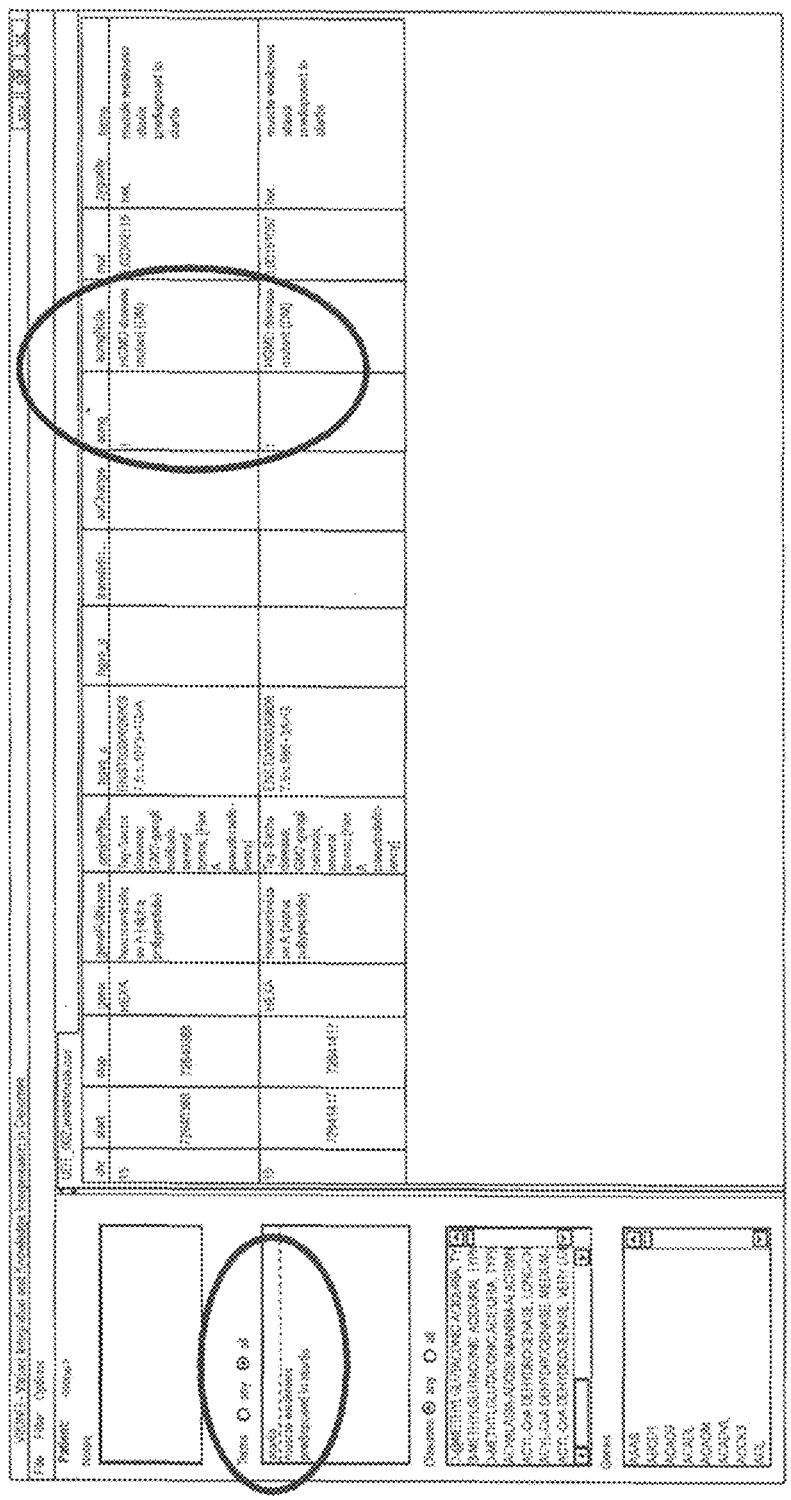
FIG. 7 is an illustration of the system of the present invention of FIG. 5.
Figure 8:
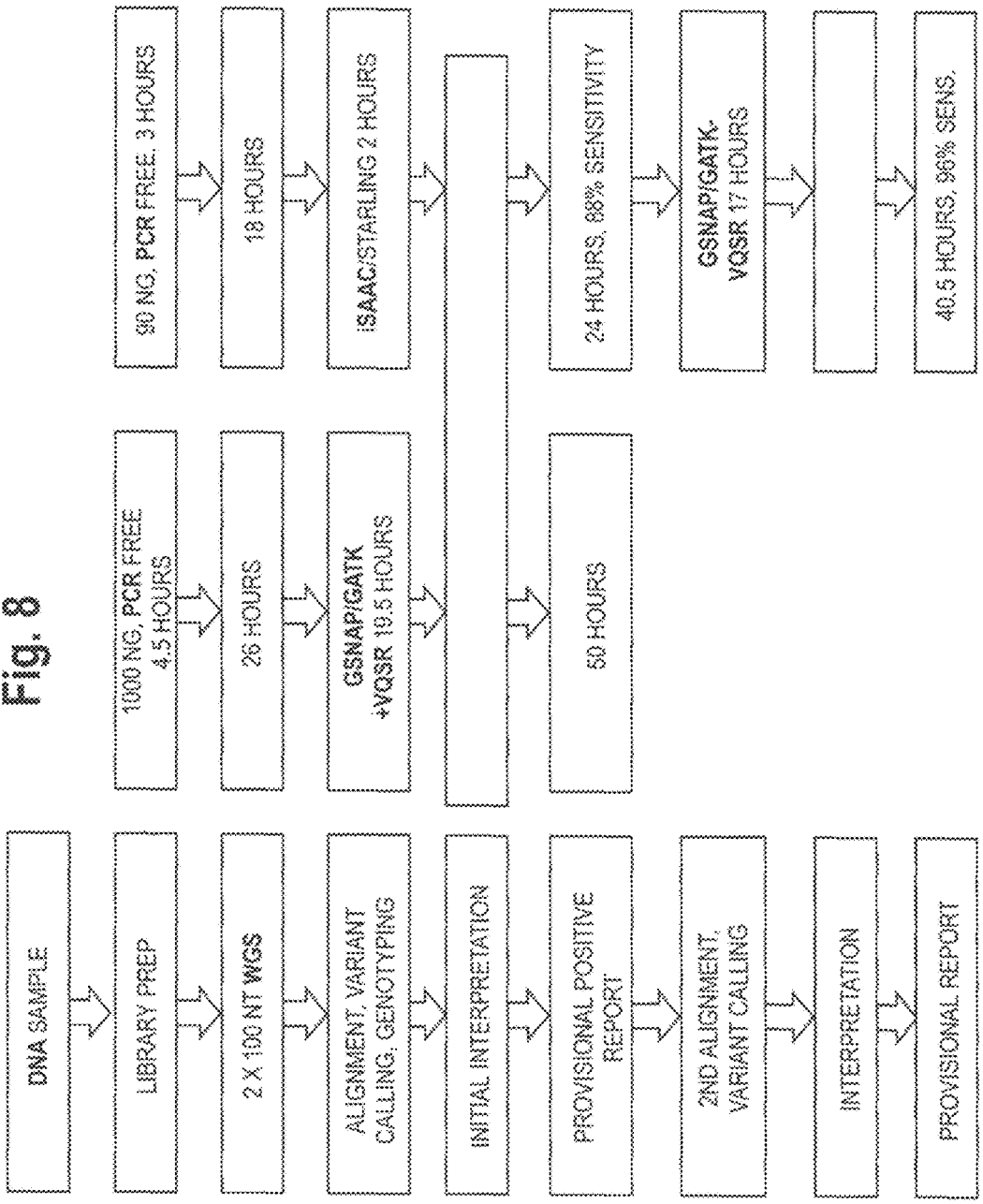
FIG. 8 is an illustration of the system of the present invention comparing a fifty hour and twenty-four hour process.

Referring to FIGS. 6 and 7, VIKING (Variant Integration and Knowledge Interpretation in Genomes) is a software tool for interpreting a patient's DNA sequencing results by integrating raw sequencing results, variant characterization results and patient symptoms. Sequencing results are presented as a list of nucleotide variants, or places where the patient's genome sequence differs from that of the human reference genome. These variants are characterized by the RUNES pipeline, which attempts to determine the significance of each variant through comparison to known databases and other in silico predictions. Patient symptoms are loaded from SSAGA along with the SSAGA predicted diseases and genes that are indicated by the symptoms. FIG. 6 shows the SSAGA symptoms, diseases and genes on the left and a filtered ranked variant list showing only mutation in genes from the SSAGA list. Variants are also filtered based on certain criteria.

VIKING then uses the information from SSAGA and RUNES to sort and filter the list of variants detected in sequencing so that only variants in genes indicated by the patient symptoms are displayed and further so that genes are ordered by the number of SSAGA terms associated to them. This allows a researcher to quickly get a list of the most relevant nucleotide variants for the patients' symptoms.

VIKING offers several additional features to assist in the interpretation of sequencing results including filtering results by gene, disease or term, filtering by minor allele frequency so that only rare variants are displayed, filtering by genes that have a compound heterozygote variant or a homozygous variant and the ability to display all RUNES annotations for each variant.

The present invention provides a method for rapid, precise, comprehensive, rapid genome, clinical feature, disease integration and interpretation in individual patients. It provides methods for genome interpretation and disease ascertainment that are comprehensive and nuanced than possible manually. It allows partial triage of genome interpretation, allowing a pathologist to have much of the interpretive effort to be automated. It allows partial triage of clinical feature integration and determination of a set of differential diagnoses. Thus, it can be employed for thousands of analyses. It has a supervised self-learning capacity, which improves the quality of the underpinning databases on the basis of observed associations. It has error correction capabilities for data entry and data analysis that are not possible manually. It is facile for physician use and is designed for rapid physician entries that are intuitive for clients and that provide immediate feedback regarding differential diagnoses and goodness of fit with clinical presentations.

In addition, the method of the present invention is extensible to a clinical decision support system (CDSS) where the software and algorithms go beyond yielding a diagnosis and additional provide individualized and genome-directed (and other feature-aware) treatment suggestions. An example is pharmacogenomics and genomic-based pharmacodynamics.

The system of the present invention can also be used for the molecular diagnosis of known (previously described) disease-causing mutations that involve large nucleotide inversions, large deletions, insertions, large triplet repeat expansions, gene conversions and complex rearrangements.

One embodiment of the present invention combines the software system outlined here and third generation DNA sequencing technologies to solve the problem of a general method for molecular diagnosis of previously described disease-causing mutations that involve large nucleotide inversions, large deletions, insertions, large triplet repeat expansions, gene conversions and complex rearrangements that are clinically important and currently undetectable by next-generation sequencing, as described more fully in the previous section.

The present invention uses use of SSAGA to define particular "on target" disease genes and to nominate specific "on target" mutations that involve previously described large nucleotide inversions, large deletions, insertions, large triplet repeat expansions, gene conversions and complex rearrangements. The clinical terms of a disease in an individually affected patient are entered by a physician, nurse, genetic counselor, or a patient into a modified form of SSAGA. As disclosed herein, SSAGA maps clinical features to diseases to genes. For genetic diseases with mutations that involve large nucleotide inversions, large deletions, insertions, large triplet repeat expansions, gene conversions and complex rearrangements, SSAGA additionally maps the disease genes to previously described mutations that involve large nucleotide inversions, large deletions, insertions, large triplet repeat expansions, gene conversions and complex rearrangements, as defined, for example, by type and nucleotide coordinates. SSAGA maps the clinical features to the superset of potentially causative diseases and disease genes. SSAGA also allows the potentially causative diseases to be rank ordered for interpretive assistance, as previously disclosed.

In addition, SSAGA maps the on target disease genes to known mutations that involve large nucleotide inversions, large deletions, insertions, large triplet repeat expansions, gene conversions and complex rearrangements that are medically relevant for molecular diagnosis. In any given patient, this is an extremely small subset of all genomic large nucleotide inversions, large deletions, insertions, large triplet repeat expansions, gene conversions and complex rearrangements. It is also a tiny subset of all large nucleotide inversions, large deletions, insertions, large triplet repeat expansions, gene conversions and complex rearrangements that have been associated with genetic diseases. In a typical patient, there can be none or a few large nucleotide inversions, large deletions, insertions, large triplet repeat expansions, gene conversions and complex rearrangements to be nominated. Genomic DNA is sequenced to provide very long DNA sequences (e.g. Pacific Biosciences SMRT sequencing or another long-read DNA sequencing technology). These sequences are aligned to the referenced human genome.

The disease genes that map to the clinical features are analyzed automatically or semi-automatically to determine the presence or absence of the very small number of the known mutations that involve large nucleotide inversions, large deletions, insertions, large triplet repeat expansions, gene conversions and complex rearrangements that are "on target" in that patient. This can either use an existing read mapping and variant detection method, such as GSNAP and the GATK, or a novel method that examines only particular large events.

The individual interpreting the data uses VIKING (as described herein) and a genome browser to identify the mutations. Importantly, this is done in addition to the previously disclosed methods for diagnosis of genetic diseases that are caused by nucleotide mutations, allowing the interpreter to examine both the hypotheses of "on target" nucleotide mutations and mutations that are large nucleotide inversions, large deletions, insertions, large triplet repeat expansions, gene conversions and complex rearrangements simultaneously.

Alternatively, in another embodiment of the system of the present invention, prior to aligning the sequences to the reference human genome, the disease genes are enriched by using an enrichment kit, such as, the TaGSCAN enrichment kit components or exome enrichment. In contrast to typical exome or TaGSCAN enrichment protocols, however, the genomic DNA is not fragmented prior to enrichment, providing enrichment of whole contiguous gene segments.

This aspect of system of the present invention fills a critical gap in the molecular diagnosis of genetic diseases in a very simple, rapid and generalize manner that can be automated, namely large nucleotide inversions, large deletions, insertions, large triplet repeat expansions, gene conversions and complex rearrangements. In certain cases these are critically important for molecular diagnosis. The system only examines "on target" mutations in individual patients, as previously disclosed. It does not require high sequence fidelity (i.e. >90%) since it is searching for long-range (5 kilobases or greater) unambiguous alignments and large genomic events and not for individual nucleotide variants. The system is able to search for all known mutations that involve large nucleotide inversions, large deletions, insertions, large triplet repeat expansions, gene conversions and complex rearrangements in genes that map to the clinical features in a given patient simultaneously. Specifically, it will work well for common mutations that involve large nucleotide inversions, large deletions, insertions, large triplet repeat expansions, gene conversions and complex rearrangements, such as the examples listed in the background section herein above.

The use of third generation DNA sequencing technologies, or a combination of second and third generation sequencing technologies, or second generation sequencing technologies with haplotype estimation (either by assembly or imputation) would allow comprehensive genomic analysis for most genetic diseases to include examination of large nucleotide inversions, large deletions, insertions, large triplet repeat expansions, gene conversions and complex rearrangements that are clinically important and currently undetectable by next-generation sequencing. An alternative approach is to supplement a comprehensive genome sequencing technology with whole transcriptome (RNA) sequencing. RNA sequencing allows the quantity of expression of each gene to be determined. Thus, RNA sequencing can allow indirect detection of the effects of large nucleotide inversions, large deletions, insertions, large triplet repeat expansions, gene conversions and complex rearrangements that are clinically important and currently undetectable by next-generation sequencing by examination of the effect on transcription of that gene or genes. Furthermore, RNA sequencing, when performed together with DNA sequencing, allows examination of allelic expression bias[5]. Allelic expression bias is exquisitely sensitive for detection of the effects of genomic variations that act in cis. Allelic expression bias can only be performed at expressed genomic locations that contain a heterozygous variant. Thus, at a heterozygous site, the proportion of expression from each allele (or chromosome) should be 50%. Deviations from 50% indicated that the variant, or a linked variant, are changing the expression of that locus. Thus, RNA sequencing with calculation of allelic expression bias can allow indirect detection of the effects of large nucleotide inversions, large deletions, insertions, large triplet repeat expansions, gene conversions and complex rearrangements that are clinically important and currently undetectable by next-generation sequencing by examination of the effect on transcription of that gene or genes on maternally and paternally derived chromosomes.

The 3,896 known monogenic diseases are frequent causes of neonatal morbidity and mortality. Conventional diagnostic testing by gene sequencing is available for only some of these, and is too slow to have clinical utility in acutely ill newborns. As such, an immense unmet need exists for rapid, comprehensive genetic disease diagnosis in newborns. Recently we described a proof-of-concept for newborn diagnosis by 50-hour whole genome sequencing (WGS). However, causal variants in monogenic diseases are very rare and often novel, and thereby often removed by standard variant calling pipelines. Here, a 24-hour (single physician shift) is described with differential diagnosis of genetic disorders by WGS with increased sensitivity for rare and novel variants. The quality and quantity of whole genome sequences from 24-hour WGS was at least as good as 50-hour WGS. A sensitivity for variant genotypes of 96% was obtained by use of two variant detection pipelines and altered variant detection parameters. In both trio and single-ton whole genome sequences, the number of true positive variants was substantially improved, with modest increases in false positive variant calls. 24-hour whole genome sequencing with the use of two variant calling pipelines is suggested as the current gold standard for use in emergency diagnosis of genetic disorders.

Figure 9:
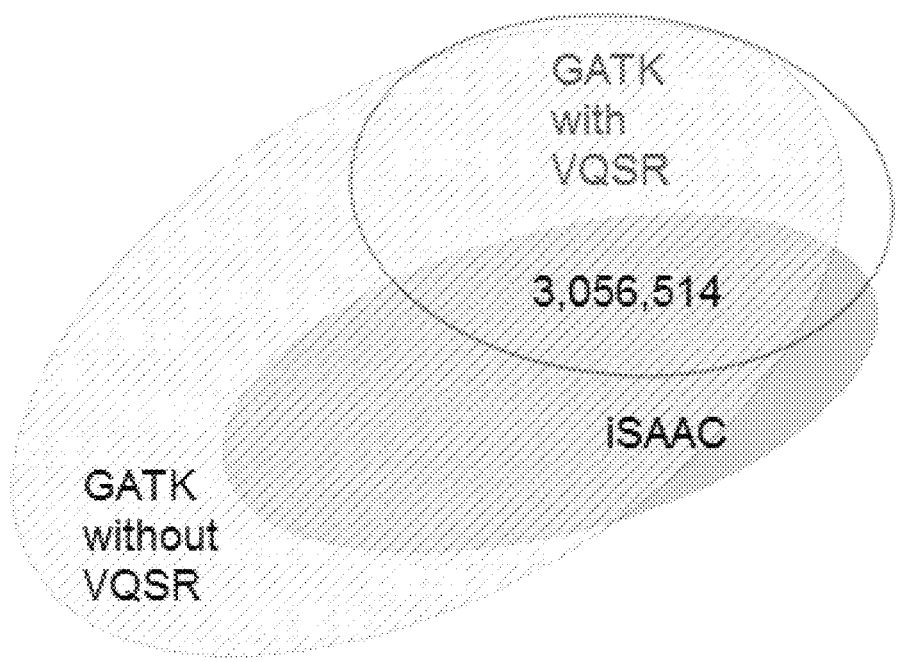
FIG. 9 is a venn diagram showing the results of three tests and how the sensitivity is increased based on running three separate tests.
Figure 10:
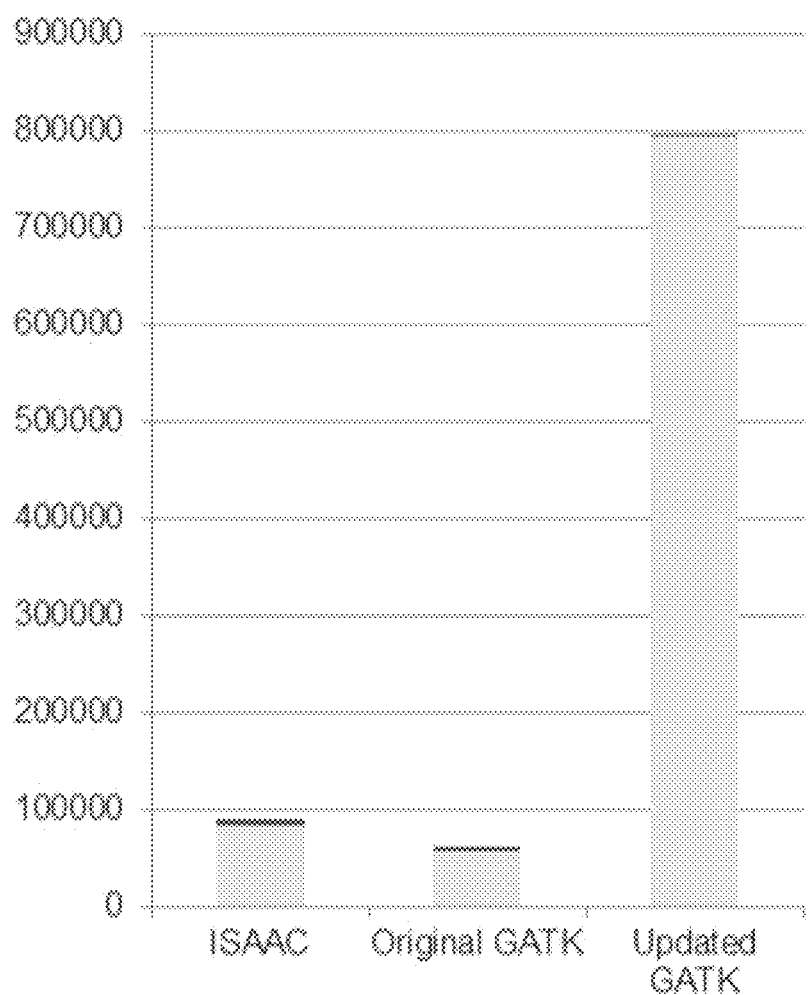
FIG. 10 is an illustration of the results of an analysis of unique variants called in whole genome sequences of sample UDT_173 (HiSeq 2500 2×100 nt rapid-run mode, 26 hour run time). Genotype differences between methods are shown in darker shading.

Shown below in Table 3 are the results comparing the number of nucleotide variants called by ISAAC with starling, GSNAP with GATK, both with and without VQSR in whole genome sequences of sample UDT_173 (HiSeq 2500 2×100 nt rapid-run mode, 26 hour run time). Also shown in FIG. 9 is a graphic representation of the results and how the sensitivity is increased based on running three separate tests. The system analyzes the collected individual phenotypic information of the individual with one, two or three different databases of mapped causative genes for genetic diseases and associated phenotypes which results in three separate and distinct phenotype-associated gene data sets. These separate data sets are then combined to use for analysis.

TABLE 3

| Variant Caller | Variants Called | Unique Variant genotypes (%) | Shared by all |
| --- | --- | --- | --- |
| iSAAC + starling | 3,693,136 | 83,754 (2.3) | 82.8% |
| GSNAP + GATK with VQSR | 3,659,456 | 57,244 (1.6) | 83.5% |
| GSNAP + GATK without VQSR | 4,917,216 | 794,026 (16.1) | 62.2% |
| Combined iSAAC/starling and GSNAP/GATK without VQSR | 5,000,970 | 0 (0) | n.a. |

As shown below in Table 4 are the results of the comparison of sensitivity and specificity of 18 and 26 hour HiSeq 2500 runs with two alignment algorithms and two sets of GATK parameters in whole genome sequences (HiSeq 2500 2×100 nt rapid-run mode). The UDT_173 genotype "truth set" was derived from hybridization to the Omni4 SNP array. The NA12878 "truth set" was from ftp://ftp-trace.ncbi.nih.gov/giab/ftp/data/NA12878/variant_calls/NIST.

TABLE 4

| Sample | Run Time | Aligner | Total Genotypes | Reference genotypes | GATK with VQSR | | GATK Without VQSR | |
| --- | --- | --- | --- | --- | --- | --- | --- | --- |
| | | | | | % Sens. | % Spec. | % Sens. | % Spec. |
| UDT_173 | 26 | GSNAP | 2,366,994 | 71.63% | 94.34 | 97.66 | 95.82 | 97.50 |
| UDT_173 | 18 | GSNAP | | 74.81% | 83.76 | 97.85 | 95.78 | 97.61 |
| UDT_173 | 26 | BWA | | 73.21% | 89.06 | 97.73 | 92.79 | 97.57 |
| UDT_173 | 18 | BWA | | 72.76% | 90.58 | 97.62 | 92.83 | 97.51 |
| NA12878 | 18 | GSNAP | 2,336,705,924 | 99.88% | 87.37 | 99.99 | 92.82 | 99.99 |

Comparison of sensitivity and specificity of variant genotypes in whole genome sequences (18 and 26 hour 2×100 nt HiSeq 2500 runs) with two methods of alignment and variant detection and the combination of both methods.

TABLE 5

| Sample | Run Time | Aligner | VQSR | Total Genotypes | % Reference Genotypes | Sensitivity | Specificity | Increase in Sensitivity |
| --- | --- | --- | --- | --- | --- | --- | --- | --- |
| NA12878 | 18 | Both | No | 2,336,705,924 | 99.86% | 95.99% | 99.99% | 8.62% |
| NA12878 | 18 | GSNAP | No | | 99.87% | 92.82% | 99.99% | |

TABLE 5-continued

| Sample | Run Time | Aligner | VQSR | Total Genotypes | % Reference Genotypes | Sensitivity | Specificity | Increase in Sensitivity |
|---|---|---|---|---|---|---|---|---|
| NA12878 | 18 | iSAAC | | | 99.88% | 87.68% | 99.99% | |
| UDT_173 | 26 | Both | No | 2,366,994 | 71.07% | 96.17% | 97.47% | 1.83% |
| UDT_173 | 26 | iSAAC | | | 71.85% | 93.61% | 98.21% | |
| UDT_173 | 26 | GSNAP | No | | 71.18% | 95.82% | 97.56% | |
| UDT_173 | 18 | Both | No | | 71.08% | 96.15% | 97.49% | 12.49% |
| UDT_173 | 18 | iSAAC | | | 71.21% | 93.53% | 98.18% | |
| UDT_173 | 18 | GSNAP | No | | 71.19% | 95.78% | 97.61% | |

As shown in Table 6 below, Comparison of concordant and discordant variants called by two different GATK parameter sets in four sets of trio genomes. The trios were: CMH184 (proband), CMH186, CMH 202; CMH185 (proband), CMH186, CMH20; CMH531 (proband), CMH532, CMH533; and CMH569 (proband), CMH570, CMH571.

TABLE 6

| Variant Segregation | Assumption | GATK with VQSR | | | | GATK without VQSR | | | | Increase in Genic Variants | Increase in Total Variants |
|---|---|---|---|---|---|---|---|---|---|---|---|
| | | Genic Variants | % Genic Variants | Total Variants | % Total Variants | Genic Variants | % Genic Variants | Total Variants | % Total Variants | | |
| Concordant in trio | True Positive | 8,435,149 | 88.34% | 20,235,824 | 87.62% | 9,166,333 | 88.92% | 20,186,631 | 88.79% | 7.66% | −0.21% |
| Both parents hom; child het | False Negative | 8,316 | 0.09% | 21,951 | 0.10% | 12,003 | 0.12% | 25,210 | 0.11% | 0.04% | 0.01% |
| Called in parent, not in child | False Negative | 349,166 | 3.66% | 909,092 | 3.94% | 310,458 | 3.01% | 739,444 | 3.25% | −0.41% | −0.73% |
| In child, not in parent | | 75,935 | 0.80% | 205,189 | 0.89% | 69,556 | 0.67% | 163,682 | 0.72% | −0.07% | −0.18% |
| Indeterminate | | 328,104 | 3.44% | 804,630 | 3.48% | 350,687 | 3.40% | 821,259 | 3.61% | 0.24% | 0.07% |
| "de novo" in child | False Positive | 351,340 | 3.68% | 917,490 | 3.97% | 399,908 | 3.88% | 799,884 | 3.52% | 0.51% | −0.51% |
| Total | | 9,548,010 | 100% | 23,094,176 | 100% | 10,308,945 | 100% | 22,736,110 | 100% | 7.97% | −1.55% |

From the foregoing it will be seen that this invention is one well adapted to attain all ends and objects hereinabove set forth together with the other advantages which are obvious and which are inherent to the structure.

It will be understood that certain features and subcombinations are of utility and can be employed without reference to other features and subcombinations. This is contemplated by and is within the scope of the claims.

Since many possible embodiments can be made of the invention without departing from the scope thereof, it is to be understood that all matter herein set forth or shown in the accompanying drawings is to be interpreted as illustrative, and not in a limiting sense.

What is claimed is:

1. A non-transitory computer-readable medium for phenotype assisted genome analysis and genetic disease diagnosis of an individual having computer-executable instructions that when executed causes one or more processors to perform the steps of:
    (a) mapping a database of causative genes for genetic diseases and a database of associated phenotypes resulting in a first database of mapped causative genes for genetic diseases and associated phenotypes;
    (b) comparing a plurality of collected individual phenotypic information of said individual with said first database of mapped causative genes for genetic diseases and associated phenotypes resulting in a first phenotype-associated gene data sets;
    (c) comparing said first phenotype-associated gene data sets with a database of individualized genomic variations identified in said individual by sequencing a genome, an exome or a part of a genome of said individual;
    (d) creating a prioritized list of phenotype-associated variations based on said comparisons; and
    (e) comparing said phenotype-associated variations of said individual with a database of genetic diseases to produce a prioritized list of probable diseases.

2. The medium of claim 1 wherein said phenotype-associated gene data sets is prioritized based on the application of Boolean operator(s) between mapped terms in said phenotype-associated gene data sets prior to the comparison function of step (c).

3. The medium of claim 1 wherein said collected phenotypic information includes one of symptoms, clinical signs, laboratory test values, blood samples, clinical term qualifiers, age of onset of these, sex, relevant family history, or specific genes of interest.

4. The computer-readable medium of claim 1 wherein said database of causative genes for genetic diseases results from mapping a database of having at least 400 genes and a genetic disease database having at least 400 genetic diseases.

5. The computer-readable medium of claim 2 wherein said gene database contains genetic variants identified in one or more first degree relatives of the individual.

6. The computer-readable medium of claim 1 where when executed performs in less than fifty hours.

7. The computer-readable medium of claim 1 where when executed performs in less than twenty-four hours.

8. The computer-readable medium of claim 1, wherein said phenotype-associated gene data sets is dynamically and automatically updated when said plurality of collected individual phenotypic information is updated.

9. The computer-readable medium of claim 1, wherein said phenotype-associated variations are updated based on the presence or absence a phenotype in one or more first degree relatives of said individual.

10. The computer-readable medium of claim 1, wherein said phenotype-associated variations are updated based on the presence or absence of a genetic variant in one or more first degree relatives of said individual.

11. The computer-readable medium of claim 1, further comprising the step of comparing a plurality of collected individual phenotypic information of said individual with a second database of mapped causative genes for genetic diseases and associated phenotypes resulting in a second phenotype-associated gene data sets, wherein said second phenotype-associated gene data sets is combined with said first phenotype-associated gene data sets and steps (c)-(e) are completed using said combined first phenotype-associated gene data sets.

12. The computer-readable medium of claim 1, further comprising the step of comparing a plurality of collected individual phenotypic information of said individual with a third database of mapped causative genes for genetic diseases and associated phenotypes resulting in a third phenotype-associated gene data sets, wherein said third phenotype-associated gene data sets is combined with said first phenotype-associated gene data sets and said second phenotype-associated gene data sets and steps (c)-(e) are completed using said combined first phenotype-associated gene data sets.

13. The computer-readable medium of claim 1, further comprising the steps of:
(i) storing at least one clinical feature of said individual entered by an end-user;
(ii) assigning a truth value to said at least one clinical feature based on the probability of the presence of said at least one clinical feature;
(iii) mapping said clinical feature(s) to at least one disease by accessing an associated database containing a plurality of data sets, wherein said data sets are made up of associates between one or more of clinical features and diseases, diseases and genes, genes and genetic variants, genetic variants and disease causality, or genes and mutations;
(iv) assigning a truth value to said at least one disease based on the probability of the presence of said at least one disease in said individual resulting in a weighted list of said at least one disease;
(v) comparing said data superset of relevant diseases and genes to said phenotype-associated variations; and
(vi) using said weighted list of said at least one disease to weight said phenotype-associated variations to provide a disease diagnosis.

14. The method of claim 13 wherein said associations in said associated database are adjusted based on updates with a known diagnosis and known clinical features, genes and gene variants in individual patients.

15. The method of claim 13 wherein said associations are adjusted using a self-learning module.

16. The method of claim 13 wherein said at least one clinical feature is a symptom, an observed symptom, a clinical sign, or a result from a laboratory test.

17. The method of claim 13 wherein said clinical feature is from a standardized vocabulary.

18. The method of claim 13 wherein said truth value of said clinical feature requires entering at least one vocabulary hedge, wherein said hedge is one of severity, longevity, or frequency of said clinical feature in said patient.

19. The method of claim 13 wherein said end-user is one of a physician, a genetic counselor, or a patient.

20. The method of claim 19 further comprising the step of prompting said patient end-user to enter said at least one clinical feature based on at least one question posed to said patient end-user.

21. The method of claim 13 further comprising the step of weighting said genetic variants based on the likelihood of altering the function of at least on gene.

22. The method of claim 13 further comprising the step of weighting said genetic variants based on a concordance of a plurality of variants with a pattern of inheritance of said disease.

23. The method of claim 13 wherein said diagnosis corresponds to a gene containing said genetic variants having the highest weight.

24. The method of claim 13 further comprising the step of updating said associations in said knowledge base based on a relationship between said clinical features, said weighted genetic variants, and said diagnosis of a given patient.

25. The method of claim 13 wherein said mutations involve at least one of nucleotide substitutions, small insertions, small deletions, large nucleotide inversions, large deletions, large insertions, large triplet repeat expansions, gene conversions, or complex rearrangements.

26. A non-transitory computer-readable medium having computer-executable instructions that when executed causes one or more processors to perform:
(a) translating at least one clinical feature of a patient that is entered by an end-user into a standardized vocabulary term;
(b) assigning a weighted value to said term based on the probability of the presence of said term and the severity of said term in said patient;
(c) mapping said term with at least one diagnosis by accessing a knowledge base containing a plurality of data sets, wherein said data sets are made up of associations between one or more of (i) clinical features and diagnoses, (ii) diagnoses and genes, (iii) genes and gene variants, (iv) diagnoses and gene variants, or (v) genes and mutations;
(d) assigning a truth value to each said mapped term and diagnosis based on said associated data sets and said weighted value;
(e) providing a list of results of a plurality of diagnoses prioritized based on said truth values;
(f) adjusting said associations in said knowledge base based on a known diagnosis and known clinical features, genes and gene variants;
(g) using the said associations to assist in the definition of genomic regions of interest for examination for causal genetic variations;

(h) identification of genetic variations in said regions in that individual by methods such as genome, exome or a part of a genome sequencing; and (i) using methods to rank order or weight said regions for likelihood of causality to guide interpretation of detected genetic variations for causality.

27. The method of claim 26 wherein said associations in said knowledge base are adjusted based on updates with a known diagnosis and known clinical features, genes and gene variants in individual patients.

28. The medium of claim 26 wherein said at least one clinical feature is a symptom, an observed symptom, a clinical sign, or a result from a laboratory test.

29. The medium of claim 26 wherein said laboratory test is a blood test or a genetic test.

30. The medium of claim 26 wherein said end-user is one of a physician, a genetic counselor, or a patient.

31. The medium of claim 30 further comprising prompting said patient end-user to enter said at least one clinical feature based on at least one question posed to said patient end-user.

32. The medium of claim 31 further comprising providing said term to said end-user to confirm or dismiss the accuracy of the translation of said term.

33. The medium of claim 26 further comprising a self-learning module operable to adjust said associations maintained in said knowledge base.

34. The medium of claim 26 further comprising querying said end-user to determine if a clinical feature of a high prioritized diagnosis is present in said patient if said clinical feature was not initially entered by said end-user and adjusting said truth value of each said mapped term and diagnosis.

35. The medium of claim 26 further comprising reprioritizing said results list based on said adjusted truth values.

36. The medium of claim 26 further comprising creating a data superset of relevant genetic disease diagnoses based on said weighted value.

37. The medium of claim 26 wherein said mutations involve at least one of nucleotide substitutions, small insertions, small deletions, large nucleotide inversions, large deletions, large insertions, large triplet repeat expansions, gene conversions, or complex rearrangements.

38. A system for phenotype assisted genome analysis and genetic disease diagnosis of an individual comprising the steps of:

(a) mapping a database of causative genes for genetic diseases and a database of associated phenotypes resulting in a first database of mapped causative genes for genetic diseases and associated phenotypes;

(b) comparing a plurality of collected individual phenotypic information of said individual with said first database of mapped causative genes for genetic diseases and associated phenotypes resulting in a first phenotype-associated gene data sets;

(c) comparing said first phenotype-associated gene data sets with a database of individualized genomic variations identified in said individual by sequencing a genome, an exome or a part of a genome of said individual;

(d) creating a prioritized list of phenotype-associated variations based on said comparisons; and (e) comparing said phenotype-associated variations of said individual with a database of genetic diseases to produce a prioritized list of probable diseases.

39. The system of claim 38, further comprising the step of comparing a plurality of collected individual phenotypic information of said individual with a second database of mapped causative genes for genetic diseases and associated phenotypes resulting in a second phenotype-associated gene data sets, wherein said second phenotype-associated gene data sets is combined with said first phenotype-associated gene data sets and steps (c)-(e) are completed using said combined first phenotype-associated gene data sets.

40. The system of claim 39, further comprising the steps of:

(i) storing at least one clinical feature of said individual entered by an end-user;

(ii) assigning a truth value to said at least one clinical feature based on the probability of the presence of said at least one clinical feature;

(iii) mapping said clinical feature(s) to at least one disease by accessing an associated database containing a plurality of data sets, wherein said data sets are made up of associates between one or more of clinical features and diseases, diseases and genes, genes and genetic variants, genetic variants and disease causality, or genes and mutations;

(iv) assigning a truth value to said at least one disease based on the probability of the presence of said at least one disease in said individual resulting in a weighted list of said at least one disease;

(v) comparing said data superset of relevant diseases and genes to said phenotype-associated variations; and (vi) using said weighted list of said at least one disease to weight said phenotype-associated variations to provide a disease diagnosis.

* * * * *